United States Patent [19]
McElroy et al.

[11] Patent Number: 5,326,760
[45] Date of Patent: Jul. 5, 1994

[54] AMINOBUTANOIC ACID COMPOUNDS HAVING METALLOPROTEASE INHIBITING PROPERTIES

[75] Inventors: Andrew B. McElroy, Durham; Peter J. Brown, Chapel Hill; David H. Drewry, Durham; James M. Salovich, Cary; Frank J. Schoenen, Efland, all of N.C.

[73] Assignee: Glaxo, Inc., Research Triangle Park, N.C.

[21] Appl. No.: 31,439

[22] Filed: Mar. 15, 1993

Related U.S. Application Data

[63] Continuation-in-part of Ser. No. 905,934, Jun. 29, 1992, abandoned.

[51] Int. Cl.$^5$ .................. A61K 31/395; A61K 31/40; C07D 209/48
[52] U.S. Cl. .................. 514/235.2; 514/255; 514/323; 514/339; 514/417; 544/144; 544/373; 546/200; 546/272; 548/477
[58] Field of Search ............ 514/339, 417, 235.2, 514/255, 323; 546/272, 200; 548/477; 544/144, 373

[56] References Cited

U.S. PATENT DOCUMENTS 4,511,504  4/1985  McCullagh et al. ............ 514/339

FOREIGN PATENT DOCUMENTS

| | | |
|---|---|---|
| 53158/90 | 3/1989 | Australia . |
| 767777 | 2/1971 | Belgium . |
| 0276436A1 | 1/1986 | European Pat. Off. . |
| 0236872A2 | 10/1986 | European Pat. Off. . |
| 0320118A2 | 6/1987 | European Pat. Off. . |
| 0369391A2 | 7/1988 | European Pat. Off. . |
| 0489577A1 | 1/1991 | European Pat. Off. . |
| 0489579A1 | 3/1991 | European Pat. Off. . |
| 0520573A1 | 11/1992 | European Pat. Off. . |
| WO91/02716 | 1/1989 | PCT Int'l Appl. . |
| WO91/15506 | 4/1990 | PCT Int'l Appl. . |
| WO91/15507 | 5/1990 | PCT Int'l Appl. . |
| WO92/09565 | 2/1991 | PCT Int'l Appl. . |
| WO92/21360 | 8/1992 | PCT Int'l Appl. . |

OTHER PUBLICATIONS

L. A. Liotta et al., "Metastatic potential correlates with enzymatic degradation of basement membrane collagen:," *Nature*, 284, 67–68 (1980).

Chantry, et al., "metalloendoprotease Cleavage of 18.2- and 14.1-Kilodalton Basic Proteins Dissociating from Rodent Myelin Membranes Generates 10.0- and 5.9-Kilodalton C-Terminal Fragments", *J. Neurochem.* 50, No. 3, 688–694 (1988).

Gravallese, et al., "In Situ Hybridization Studies of Stromelysim and Collagen Messenger RNA Expression in Rheumatoid Synovium", *Arthritis and Rheumatism*, 34, No. 9, 1076–1084 (1991).

Wooley, et al., "Collagenase at Sites of Cartilage Erosion in the Rheumatoid Joint", *Arthritis and Rheumatism*, 20 No. 6, 1231–1239 (1977).

*Primary Examiner*—Johann Richter
*Attorney, Agent, or Firm*—Gardiner F. H. Smith

[57] ABSTRACT

Aminobutanoic acids of the following formula (I):

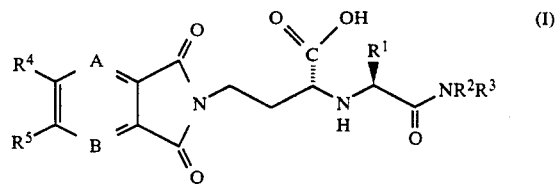

where $R^1$–$R^5$ are a variety of substituents, novel intermediates, a pharmaceutical composition for treating inflammatory diseases, demyelinating diseases, and tumor metastasis, methods for such treatment and processes for preparing compounds of formula (I).

20 Claims, No Drawings

AMINOBUTANOIC ACID COMPOUNDS HAVING METALLOPROTEASE INHIBITING PROPERTIES

This application is a continuation-in-part of U.S. Ser. No. 07/905,934 filed Jun. 29, 1992 now abandoned.

BACKGROUND OF THE INVENTION

The matrix metalloprotease family of zinc endoproteinases includes interstitial (type 1) and neutrophil collagenase (MMP1 and MMP8), the stromelysins (also known as proteoglycanases or transins), fibroblast and polymorphonuclear leucocyte gelatinases (also known as collagen-IV-ases) and 'pump-1' (putative metalloprotease 1, uterine metalloprotease). Accelerated breakdown of connective tissues by metalloprotease catalyzed resorption of extracellular matrix is a feature of many pathological conditions. Matrix metalloproteases are involved in connective tissue degradation of several inflammatory conditions where the breakdown of articular cartilage and bone leads to stiffness and immobility. Aberrant regulation of these enzymes has been implicated in pathologies such as rheumatoid arthritis. See *Arthritis and Rheumatism*, 20, 1231–1239 (1977). Interstitial collagenase and stromelysin have been found at elevated levels in the joints of many patients suffering from rheumatoid arthritis as shown by immunolocalization of collagenase at sites of erosion. See *Arthritis and Rheumatism*, 34, 1076–1105 (1991).

Matrix metalloproteases have also been implicated in the initiation of tumor metastisis/angiogenesis, and in the pathogenesis of demyelating diseases of the nervous system. See *Nature*, 284, 67–68, (1980), and *J. Neurochem.*, 50, 688–694 (1988). Additionally, matrix metalloproteases may be involved in conditions such as arthropathy, dermatological conditions, bone resorption, osteopenias such as osteoporosis, hyperparathyroidism, cholesteatoma, osteoarthritis, periodontitis, gingivitis, dystrophic epidermolysis bullosa, corneal ulceration, multiple sclerosis, optic neuritis, neuromyelitis optica, diffuse and transitional sclerosis, and acute disseminated encephalomyelitis and demyelinating peripheral neuropathies including acute inflammatory demyelinating polyradiculoneuropathies [Landry-Guillain-Barre-Strohl syndrome for motor defects and analogous syndromes for sensory and autonomic (pandysautonomia) deficits].

The compounds of the present invention act as inhibitors of matrix metalloproteases and are therefore useful in treating or preventing conditions which involve tissue breakdown including rheumatoid arthritis and various diseases in which matrix metalloprotease activity is important. A number of small peptide-like compounds which inhibit collagenase are taught in U.S. Pat. No. 4,511,504. Aminobutanoic acid tripeptide inhibitors of metalloproteases are taught in EP 0 520 573 A1, published Jun. 23, 1992. Thiol based derivatives and hydroxamic acid based derivitives are taught in International Application WO 91/02716 published Mar. 7, 1991. Phosphonic acid derivatives are taught in International Application WO 91/15507 published Sep. 17, 1991. European Application EP 0276 436 A1 published Aug. 3, 1988 teaches phosphinic acid derivatives as does European Application EP 0 236 872 A2 published Sep. 16, 1987.

SUMMARY OF THE INVENTION

Aminobutanoic acids useful as inhibitors of metalloproteases of the following formula (I):

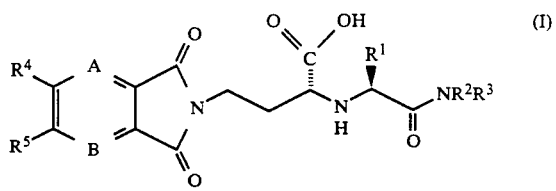

wherein:
A and B are independently N or CR where R is hydrogen, halogen, $C_{1-4}$alkyl or $C_{1-4}$alkoxy;
$R^1$ is $C_{3-6}$alkyl or $C_{1-4}$alkylthio$C_{1-4}$alkyl;
$R^2$ is hydrogen, $C_{1-4}$alkyl or hydroxy$C_{1-4}$alkyl;
$R^4$ is hydrogen, hydroxy, $C_{1-6}$alkyl, $C_{1-6}$alkoxy or halogen;
$R^3$, $R^5$, $NR^2R^3$ together and $R^4R^5$ together are a variety of substituents.

DETAILED DESCRIPTION OF THE INVENTION

The invention relates to novel chemical compounds and pharmaceutical compositions thereof. In particular, the subject chemical compounds are aminobutanoic acids of the formula (I):

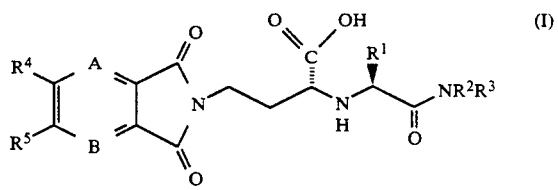

wherein:
A and B are independently N or CR where R is hydrogen, halogen, $C_{1-4}$alkyl, $C_{1-4}$alkoxy, e.g. methoxy, ethoxy, propoxy or butoxy;
$R^1$ is $C_{3-6}$alkyl or $C_{1-4}$alkylthio$C_{1-4}$alkyl;
$R^2$ is hydrogen, $C_{1-4}$alkyl or hydroxy$C_{1-4}$alkyl, e.g. hydroxyethyl;
$R^3$ is $C_{1-4}$alkyl, $C_{1-4}$alkoxy, $C_{1-4}$alkylamino, e.g. methylamino, ethylamino or propylamino, tris(hydroxymethyl)methyl, aryl, substituted aryl, arylsulfonyl, (substituted aryl)sulfonyl, benzylsulfonyl, heteroarylsulfonyl, (substituted heteroaryl)sulfonyl, heteroarylcarbonyl, (substituted heteroaryl)carbonyl or —$(CH_2)_n$CHR$^6$R$^7$ where
n is the integer 0, 1, 2, 3 or 4;
$R^6$ is hydrogen, $C_{1-4}$alkyl, $C_{1-4}$alkoxy, $C_{1-4}$alkylamino;
$R^7$ is hydroxy, mono- or di-($C_{1-4}$alkyl)amino, aryl, substituted aryl, heteroaryl, substituted heteroaryl, a saturated 5, 6, or 7 membered ring optionally interrupted by 1, 2, 3, or 4 N, S, or O heteroatoms, sulfonyl or carbonyl, with the proviso that any two O or S atoms are not bonded to each other, e.g. piperazinyl, tetrahydropyranyl, piperidinyl, morpholino, pyrrolidinyl, S,S-dioxotetrahydrothiophenyl or furanyl, such saturated ring optionally mono-, di-, tri-, or tetrasubstituted independently with $C_{1-4}$alkyl, hydroxy, oxo, nitro, hydroxy$C_{1-4}$alkyl, aryl, substituted aryl, aminocarbonyl or acetylamino substituents;

or CHR$^6$R$^7$ together form a saturated 5 to 13 membered ring optionally interrupted by 1, 2, 3, or 4 N, S, or O heteroatoms, sulfonyl or carbonyl, with the proviso that any two O or S atoms are not bonded to each other, e.g. diazacyclotridecane, such saturated ring optionally mono-, di-, or tri, or tetrasubstituted independently with C$_{1-4}$alkyl, hydroxy, oxo, nitro, hydroxyC$_{1-4}$alkyl, aryl, substituted aryl, aminocarbonyl or acetylamino substituents, a saturated 6, 7 or 8 membered bicyclic ring optionally interrupted by 1, 2, 3, or 4 N, S, or O heteroatoms, with the proviso that any two O or S atoms are not bonded to each other, e.g. azabicyclooctane, a 9 or 10 membered bicyclic ring which is partially aromatic, e.g. tetrahydronaphthalene, such bicyclic ring optionally mono-, di-, or trisubstituted independently with C$_{1-4}$alkyl, halogen, amino, hydroxy, (C$_{1-2}$alkylsulfonyl)amino, nitro, aminosulfonyl, carboxy, COO(C$_{1-4}$alkyl), trifluoromethyl, mono- or disubstituted (C$_{1-2}$alkyl)amino or trifluoromethylsulfonylamino substituents, a 9 or 10 membered heterobicyclic ring which is partially aromatic, interrupted by 1, 2, 3, or 4 N, S, O heteroatoms, carbonyl or sulfonyl, with the proviso that any two O or S atoms are not bonded to each other, such heterobicyclic ring optionally mono-, di-, or trisubstituted independently with C$_{1-4}$alkyl, halogen, amino, hydroxy, (C$_{1-2}$alkylsulfonyl)amino, nitro, aminosulfonyl, carboxy, COO(C$_{1-4}$alkyl), trifluoromethyl, mono- or disubstituted (C$_{1-2}$alkyl)amino or trifluoromethylsulfonylamino substituents;

or NR$^2$R$^3$ together form a saturated 5, 6, or 7 membered ring optionally interrupted by 1, 2, 3, or 4 N, S, or O heteroatoms, carbonyl or sulfonyl, with the proviso that any two O or S atoms are not bonded to each other, such saturated ring optionally mono-, di-, or trisubstituted independently with C$_{1-4}$alkyl, hydroxy, nitro, aryl, substituted aryl, 2, 3-dihydroxypropyl, heteroaryl, substituted heteroaryl, -CH$_2$COO(C$_{1-4}$alkyl), COO(C$_{1-4}$alkyl), amino, carboxy, acetylamino, oxo, aminosulfonyl, aminocarbonyl, trifluoromethyl, trifluoromethylsulfonylamino, mono- or di(C$_{1-4}$alkyl)amino, halogen or (C$_{1-4}$alkylsulfonyl)amino substituents, a 9 or 10 membered bicyclic ring which is partially aromatic, such bicyclic ring optionally mono-, di-, or trisubstituted independently with C$_{1-4}$alkyl, halogen, amino, hydroxy, (C$_{1-2}$alkylsulfonyl)amino, nitro, aminosulfonyl, carboxy, COO(C$_{1-4}$alkyl), trifluoromethyl, mono- or disubstituted (C$_{1-2}$alkyl)amino or trifluoromethylsulfonylamino substituents, an 9 or 10 membered heterobicyclic ring which is partially aromatic, such heterobicyclic ring interrupted by 1, 2, 3, or 4 N heteroatoms, e.g. purine, such heterobicyclic ring optionally mono-, di-, or trisubstituted independently with oxo, aryl, substituted aryl, heteroaryl, substituted heteroaryl, C$_{1-4}$alkyl, halogen, amino, hydroxy, acetylamino, (C$_{1-4}$alkylsulfonyl)amino, nitro, aminosulfonyl, aminocarbonyl, carboxy, COO(C$_{1-4}$alkyl), trifluoromethyl, mono- or disubstituted (C$_{1-4}$alkyl)amino, 2,3-dihydroxypropyl or trifluoromethylsulfonylamino substituents;

R$^4$ is hydrogen, hydroxy, C$_{1-6}$alkyl, C$_{1-6}$alkoxy or halogen;

R$^5$ is hydrogen, C$_{1-6}$alkyl, amino, aminoC$_{1-4}$alkyl, mono-or di-(C$_{1-4}$alkyl)amino, mono- or di-(C$_{1-4}$alkyl)aminoC$_{1-4}$alkyl, acetylamino, aryl, substituted aryl, (aryl)sulfonylamino, nitro, (C$_{1-4}$alkyl)sulfonylamino, hydroxy, C$_{1-6}$alkoxy, halogen, morpholino, piperazinyl, piperidinyl, (aryl)C$_{1-4}$alkoxy, (substituted aryl)C$_{1-4}$alkoxy, aryloxy, (substituted aryl)oxy, (aryl)C$_{1-4}$alkyl, (substituted aryl)C$_{1-4}$alkyl, heteroaryl, substituted heteroaryl, (heteroaryl)C$_{1-4}$alkyl, (substituted heteroaryl)C$_{1-4}$alkyl, (heteroaryl)C$_{1-4}$alkoxy, (substituted heteroaryl)C$_{1-4}$alkoxy, heteroaryloxy or (substituted heteroaryl)oxy;

or R$^4$R$^5$ together form an aryl, substituted aryl or a saturated 5 or 6 membered ring optionally interrupted by 1, 2, or 3 N, S, or O heteroatoms, with the proviso that any two O or S atoms are not bonded to each other, such saturated ring optionally mono-, di-, or trisubstituted independently with from C$_{1-4}$alkyl, oxo, nitro or aminosulfonyl substituents;

C$_{1-4}$alkyl in more detail includes methyl, ethyl, propyl, isopropyl, butyl, isobutyl or tert-butyl;

halogen in more detail includes fluorine, chlorine, bromine or iodine;

aryl in more detail includes phenyl or napthal;

substituted aryl in more detail includes aryl mono-, di-, or trisubstituted independently with C$_{1-4}$alkyl, halogen, amino, hydroxy, acetylamino, (C$_{1-4}$alkylsulfonyl)amino, nitro, aminosulfonyl, aminocarbonyl, carboxy, COO(C$_{1-4}$alkyl), trifluoromethyl, mono- or disubstituted (C$_{1-4}$alkyl)amino, aryl, 2,3-dihydroxypropyl or trifluoromethylsulfonylamino substituents;

heteroaryl in more detail includes a 5 or 6 membered aromatic ring optionally interrupted by 1, 2, 3 or 4 N, S, or O heteroatoms, with the proviso that any two O or S atoms are not bonded to each other, e.g. pyridine, pyrimidine, pyrrole, pyrazole, imidazole, thiazole, triazole, tetrazole, furan, pyran or thiophene;

substituted heteroaryl in more detail includes heteroaryl mono-, di-, or trisubstituted independently with C$_{1-4}$alkyl, halogen, amino, hydroxy, acetylamino, (C$_{1-4}$alkylsulfonyl)amino, nitro, aminosulfonyl, aminocarbonyl, carboxy, COO(C$_{1-4}$alkyl), trifluoromethyl, mono- or disubstituted (C$_{1-4}$alkyl)amino, aryl, 2,3-dihydroxypropyl, or trifluoromethylsulfonylamino substituents.

Particular groups of compounds of the formula (I) are the following:

1. A and B are independently N or CR where
   R is hydrogen, halogen, C$_{1-3}$alkyl or C$_{1-3}$alkoxy;
   R$^1$ is C$_{3-6}$alkyl;
   R$^2$ is hydrogen, methyl, ethyl or hydroxyC$_{1-3}$alkyl;
   R$^3$ is C$_{1-3}$alkyl, C$_{1-4}$ alkoxy, C$_{1-3}$alkylamino, tris(hydroxymethyl)methyl, aryl, such aryl optionally mono-, di-, or trisubstituted independently with amino, aminosulfonyl or trifluoromethylsulfonylamino substituents, phenylsulfonyl, benzylsulfonyl, pyridinylsulfonyl, pyridinylcarbonyl, or —(CH$_2$)$_n$CHR$^6$R$^7$ where
   n is the integer 0, 1, 2 or 3;
   R$^6$ is hydrogen or C$_{1-3}$alkyl;
   R$^7$ is mono- or disubstituted C$_{1-3}$alkylamino, aryl, such aryl such aryl optionally mono-, di-, or trisubstituted independently with C$_{1-3}$alkyl, halogen, amino, hydroxy, (C$_{1-2}$alkylsulfonyl)amino, nitro, aminosulfonyl, carboxy, COO(C1-4alkyl), trifluoromethyl, mono- or disubstituted (C$_{1-2}$alkyl)amino, or trifluoromethylsulfonylamino substituents, heteroaryl, such heteroaryl optionally mono-, di-, or trisubstituted independently with C$_{1-3}$alkyl, amino or hydroxy substituents, a saturated 5, 6, or 7 membered ring optionally interrupted by 1 or 2 N, S, or O heteroatoms, sulfonyl or carbonyl, with the proviso that any two O or S atoms are not bonded to each other, such saturated ring optionally mono-, di-, tri-or tetrasubstituted independently with C$_{1-3}$alkyl, hydroxy, hydroxyC$_{1-3}$alkyl, aminocarbonyl, acetylamino, oxo, nitro or phenyl substituents;

or CHR$^6$R$^7$ together form a saturated 5, 6, 8, 10, or 13 membered ring optionally interrupted by one to two N, S, O heteroatoms, or sulfonyl, with the proviso that any two O or S atoms are not bonded to each other, such saturated ring optionally mono-, di-, tri- or tetrasubstituted independently with C$_{1-3}$alkyl, hydroxy, hydroxyC$_{1-3}$alkyl, oxo, aminocarbonyl or acetylamino substituents, saturated 6, 7 or 8 membered bicyclic ring optionally interrupted by 1 to 2N heteroatoms, 9 or 10 membered bicyclic ring which is partially aromatic, such bicyclic ring optionally mono-, di, or trisubstituted independently with C$_{1-3}$alkyl, halogen, amino, hydroxy, (C$_{1-2}$alkylsulfonyl)amino, nitro, aminosulfonyl, carboxy, COO(C1-4alkyl), trifluoromethyl, mono- or disubstituted (C$_{1-2}$alkyl)amino or trifluoromethylsulfonylamino substituents;

or NR$^2$R$^3$ together form a saturated 5 or 6 membered ring optionally interrupted by one N, S, or O heteroatom, or sulfonyl, such saturated ring optionally mono-, di-, or trisubstituted independently with C$_{1-3}$alkyl, oxo, phenyl, 2,3-dihydroxypropyl, pyridinyl, ethoxycarbonyl or ethoxycarbonylmethyl substituents, 10 membered bicyclic ring which is partially aromatic;

R$^4$ is hydrogen C$_{1-3}$alkyl, C$_{1-3}$alkoxy, halogen or hydroxy;

R$^5$ is amino, nitro, (C$_{1-3}$alkylsulfonyl)amino, hydrogen, C$_{1-3}$alkyl, hydroxy, methoxy, propoxy, benzoxy, bromine, phenyl or (phenyl)sulfonylamino;

or R$^4$R$^5$ together form a benzene ring or a saturated 5 or 6 membered ring optionally interrupted by 1N heteroatom, such saturated ring optionally bearing 1 or 2 oxo substituents.

2. R$^1$ is isobutyl.

3. R$^7$ is phenyl optionally mono-, di-, or trisubstituted independently with C$_{1-3}$alkyl, halogen, amino, hydroxy, (C$_{1-2}$alkylsulfonyl)amino, nitro, aminosulfonyl, carboxy, COO(C1-4alkyl), trifluoromethyl, mono- or disubstituted (C$_{1-2}$alkyl)amino or trifluoromethylsulfonylamino substituents.

4. R$^7$ is a 5 or 6 membered heteroaryl ring interrupted by 1, 2, 3, or 4 N, or one O heteroatom, such heteroaryl optionally mono- or disubstituted independently with C$_{1-3}$alkyl, amino or hydroxy substituents.

5. CHR$^6$R$^7$ together form a 9 or 10 membered bicyclic ring which is partially aromatic, such bicyclic ring optionally mono-, di, or trisubstituted independently with C$_{1-3}$alkyl, halogen, amino, hydroxy, (C$_{1-2}$alkylsulfonyl)amino, nitro, aminosulfonyl, carboxy, COO(C1--4alkyl), trifluoromethyl, mono- or disubstituted (C$_{1-2}$alkyl)amino or trifluoromethylsulfonylamino substituents, a 9 or 10 membered heterobicyclic ring which is partially aromatic, such heterobicyclic ring optionally interrupted by 1 to 2N, S, O heteroatoms, carbonyl, or sulfonyl, such heterobicyclic ring optionally mono-, di-, or trisubstituted independently with C$_{1-3}$alkyl, halogen, amino, hydroxy, (C$_{1-2}$alkylsulfonyl)amino, nitro, aminosulfonyl, carboxy, COO(C1-4alkyl), trifluoromethyl, mono- or disubstituted (C$_{1-2}$alkyl)amino or trifluoromethylsulfonylamino substituents.

(6)

R$^1$ is isobutyl;
R$^2$ is hydrogen;
n is 0;
R$^6$ is hydrogen or methyl;
R$^7$ is phenyl optionally mono- or disubstituted independently with fluoro, carboxy, COO(C1-4alkyl) or aminosulfonyl substituents;
R$^4$R$^5$ together form a benzene ring.

(7)

R$^1$ is isobutyl;
R$^2$ is hydrogen;
n is 0;
R$^6$ is hydrogen or methyl;
R$^7$ is monofluorophenyl or difluorophenyl;
R$^4$R$^5$ together form a benzene ring.

(8)

R$^1$ is isobutyl;
R$^2$ is hydrogen;
R$^2$R$^3$ together form a 6 membered saturated ring optionally interrupted by one N heteroatom, such ring optionally mono- or disubstituted independently with methyl, ethoxycarbonyl, ethoxycarbonylmethyl, 2,3-dihydroxypropyl or pyridinyl substituents;
R$^4$R$^5$ together form a benzene ring.

(9)

R$^1$ is isobutyl;
R$^2$ is hydrogen;
n is 1;
R$^6$ is hydrogen;
R$^7$ is tetrazole optionally mono- or disubstituted independently with C$_{1-3}$alkyl substituents;
R$^4$R$^5$ together form a benzene ring.

(10)

R$^1$ is isobutyl;
R$^2$ is hydrogen or methyl;
n is 0 or 1;
R$^6$ is hydrogen;
R$^7$ is phenyl;
R$^4$R$^5$ together form a benzene ring.

(11)

R$^1$ is isobutyl;
R$^2$ is hydrogen;
n is 0;
R$^6$R$^7$ together form a 13 membered saturated ring interrupted by 1 or 2N heteroatoms, such ring optionally mono-, di-, or trisubstituted independently with oxo or methyl substituents;
R$^4$R$^5$ together form a benzene ring.

(12)

R$^1$ is isobutyl;
R$^2$ is hydrogen;
n is 0;
R$^6$ is hydrogen;
R$^7$ is phenyl;
R$^4$ is hydrogen;
R$^5$ is hydrogen or C$_{1-6}$ alkoxy.

(13)

R$^1$ is isobutyl;
R$^2$ is methyl;
n is 0;
R$^6$ is hydrogen;
R$^7$ is phenyl;
R$^4$R$^5$ together form a benzene ring.

Also part of the present invention are intermediates used in the various processes of the invention. Examples include intermediates of formula (II):

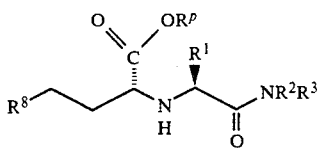

wherein:
$R^1$ is isobutyl;
$R^2$ is hydrogen;
$R^3$ is $-(CH_2)_n CHR^6 R^7$ where
n represents the integer 0, 1, 2, 3, 4, or 5;
$R^6$ represents hydrogen;
$R^7$ is aryl e.g. benzene, napthalene, anthracene, or phenathrene, such aryl optionally substituted with 1, 2, or 3 substituents independently selected from aminosulfonyl, nitro, $C_{1-3}$alkyl, phenyl, 2,3-dihydroxypropyl, amino, carboxy, COO(C1-4alkyl), acetylamino, aminocarbonyl, hydroxy, trifluoromethyl, trifluoromethylsulfonylamino, halogen, ($C_{1-3}$alkylsulfonyl)amino, or mono- or di($C_{1-4}$alkyl)amino, a heteroaryl ring, e.g. a 5, 6, or 7 member ring interrupted by 1, 3, or 4 N, S, or O heteroatoms, such heteroaryl optionally bearing 1, 2, 3, or 4 substituents independently selected from $C_{1-4}$alkyl, halogen, amino, hydroxy, acetylamino, ($C_{1-3}$alkylsulfonyl)amino, nitro, aminosulfonyl, aminocarbonyl, carboxy, COO(C1-4alkyl), trifluoromethyl, mono- or di($C_{1-4}$alkyl)amino, or trifluoromethylsulfonylamino;
$R^8$ is hydroxyl, (1,1-dimethylethyl)-dimethylsilyloxy, halogen, or $OSO_2R^9$ where
$R^9$ is $C_{1-3}$alkyl, e.g. methyl, ethyl or propyl, haloalkyl, e.g. trifluoromethyl, aryl, e.g. phenyl or tosyl;
$R^p$ is a protecting group such as methyl, ethyl, propyl, 1,1-dimethylethyl, or like ester, which is removed following the reaction.

The compounds of formula (I) may be prepared by methods known in the art of organic synthesis, an example being shown in Scheme 1:

Scheme 1

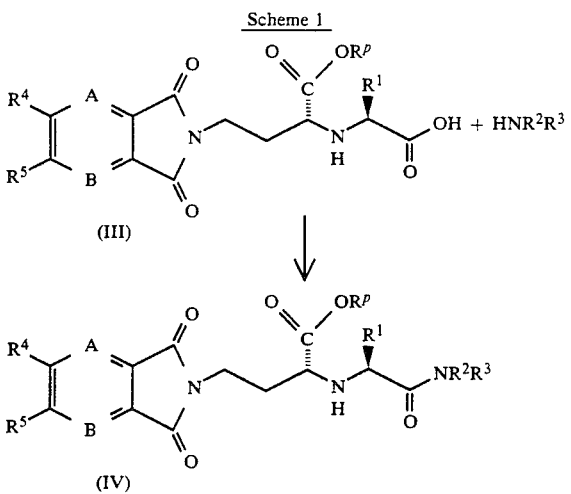

wherein:
$R^1$, $R^2$, $R^3$, $R^4$, and $R^5$ are defined for formula (I). $R^p$ is any of several protecting groups including, but not limited to, a readily cleavable ester such as the methyl, ethyl, tert-butyl or like ester, which is removed following the reaction. For detailed examples of the use and removal of these carboxy protecting groups see T. W. Greene, Protective Groups in Organic Synthesis, John Wiley & Sons, 1981, p.218-323. The condensation reaction may be carried out in a manner which is known per se in peptide chemistry; for example the condensation may be carried out according to an activated ester method, particularly using 1-hydroxybenzotriazole in the presence of a condensation agent such as N,N'-dicyclohexylcarbodiimide and in a suitable solvent, e.g. dimethylformamide.

Another example of a method for preparing compounds of formula (I) is shown is Scheme 2:

Scheme 2

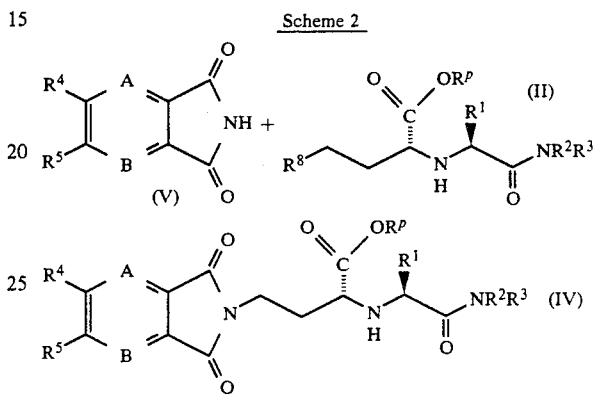

$R^1$, $R^2$, $R^3$, $R^4$, and $R^5$ are as defined for formula (I),
$R^8$ is hydroxyl, halogen, or $OSO_2R^9$ where
$R^9$ is $C_{1-3}$alkyl, haloalkyl, e.g. trifluoromethyl, aryl, or aryl substituted with methyl,
$R^p$ is as defined above including removal following the reaction. The displacement reaction may be carried out in a suitable solvent such as an ether, e.g. tetrahydrofuran, a nitrile, e.g. acetonitile, or an amide, e.g. dimethylformamide, at a temperature of 20° to 150° C. The reaction is effected in the presence of a base such as an organic base, e.g. triethylamine, or an inorganic base, e.g. sodium hydroxide.

When $R^8$ is hydroxyl the compound of formula (II) is treated with the cyclic imide of formula (V) in the presence of an activating system such as triphenylphosphine and diethylazodicarboxylate.

Another example of a method for preparing compounds of formula (I) is shown is Scheme 3:

Scheme 3

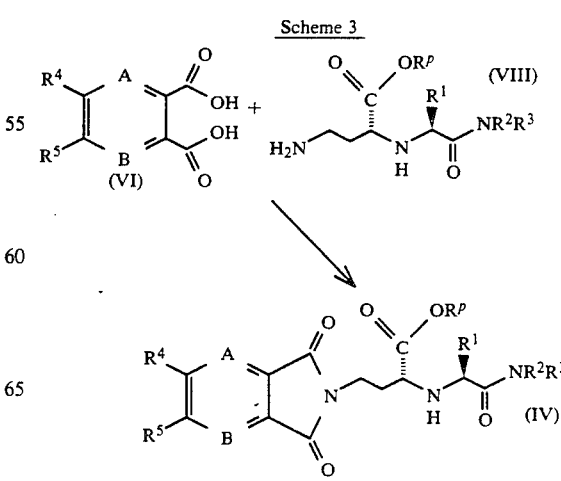

-continued
Scheme 3

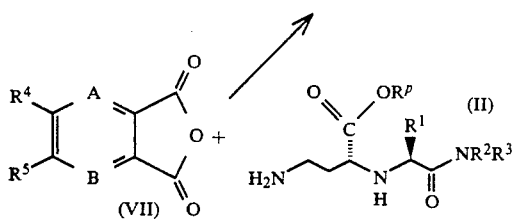

$R^1$, $R^2$, $R^3$, $R^4$, and $R^5$ are as defined for formula (I), $R^p$ is as defined above including removal following the reaction. The introduction of a cyclic imido group may be carried out in a manner known per se in organic chemistry. The compound of formula (VIII) may be reacted with the suitable activated aromatic bis-carboxylic acid of formula (VI) or the suitable activated aromatic bis-carboxylic acid anhydride derivative of formula (VII) in accordance with known methods. Other suitable activated aromatic bis-carboxylic acid derivatives include mixed anhydrides, chlorides, esters, thioesters, etc. Alternatively, activation of the aromatic bis-carboxylic acid may be effected in situ using methods known in peptide chemistry.

Another example of a method for preparing compounds of formula (I) is shown in Scheme 4:

Scheme 4

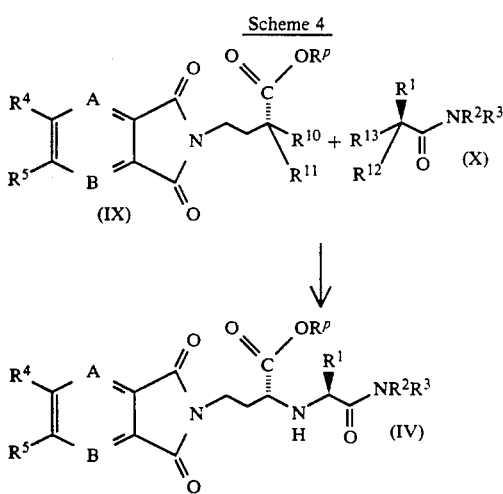

$R^1$, $R^2$, $R^3$, $R^4$, and $R^5$ are as defined for formula (I), $R^p$ is as defined above including removal following the reaction. $R^{10}R^{11}$ together form an oxo group, or $R^{10}$ is hydrogen and $R^{11}$ is hydroxyl, halogen, or $OSO_2R^9$ where $R^9$ is as defined above when $R^{12}$ is hydrogen and $R^{13}$ is $NH_2$ or alternatively $R^{10}$ is hydrogen and $R^{11}$ is $NH_2$ when $R^{12}$ and $R^{13}$ together form an oxo group or $R^{12}$ is hydrogen and $R^{13}$ is halogen, or $OSO_2R^9$ where $R^9$ is as defined above. The reaction is conducted under conventional conditions of amination or reductive amination as appropriate.

Another example of a method for preparing compounds of formula (I) is a process comprised of the deprotection a protected derivitive of a compound of formula (I). It will be appreciated that in the above Schemes 1 through 4 the removal of the protecting group $R^p$ is required as a step subsequent to the main process step. It will also be appreciated that other functional groups present in appropriate starting materials may need to be protected, and deprotection may thus be required as an intermediate or final step to yield the desired compound. Protection and deprotection of functional groups may be effected using conventional means. Thus, for example, amino groups may be protected by a group selected from aralkyl (e.g. benzyl), acyl, or sulfonyl, e.g. allylsulfonyl, phthalimide, or tosyl; subsequent removal of the protecting group being effected when desired by hydrolysis or hydrogenolysis as appropriate using standard conditions. Hydroxyl groups may be protected using any conventional hydroxyl protecting group, for example, as described in 'Protective Groups in Organic Synthesis', Ed. J. F. W. McOnie (Plenum Press, 1973). Examples of suitable hydroxyl protecting groups include groups selected from alkyl, e.g. methyl, tert-butyl, or methoxymethyl, aralkyl, e.g. benzyl, diphenylmethyl, or triphenylmethyl, heterocyclic groups such as tetrahydropyranyl, acyl. e.g. acetyl or benzoyl, and silyl groups such as trialkylsilyl, e.g. tert-butyldimethylsilyl. The hydroxyl protecting groups may be removed by conventional techniques. Thus, for example, alkyl, silyl, acyl, and heterocyclic groups may be removed by hydrolysis under acidic or basic conditions. Aralkyl groups such as triphenylmethyl may similarly be removed by hydrolysis under acidic conditions. Aralkyl groups such as benzyl may be cleaved by hydrogenolysis in the presence of a Noble metal catalyst such as palladium-on-charcoal. Silyl groups may also conveniently be removed using a source of fluoride ions such as tetra-n-butylammonium fluoride. Carboxyl protecting groups may conveniently be represented by appropriate hydroxyl protecting groups above with deprotection effected according to the methods described above.

Suitable pharmaceutically acceptable salts of the compounds of formula (I) include acid addition salts formed with organic or inorganic acids, e.g. hydrochlorides, hydrobromides, sulfates, alkyl- or arylsulfonates (methanesulfonates or p-toluenesulfonates), phosphates, acetates, citrates, succinates, lactates, tartrates, fumarates, and maleates; and inorganic base salts such as alkali metal salts e.g. sodium salts. The solvates may, for example, be hydrates.

Other salts which are not pharmaceutically acceptable may be useful in the preparation of compounds of formula (I) and these form a further aspect of the invention.

It is to be understood that the present invention encompasses the individual enantiomers of the compounds represented by formula (I) above as well as wholly or partially racemic mixtures thereof. The present invention also covers the individual enantiomers of the compounds represented by formula (I) above as mixtures with diastereoisomers thereof in which one or more of the two stereocenters is inverted.

Also part of the present invention are intermediates used in the various processes of the invention. Examples include intermediates of formulas (II), (III), (IV).

PHARMACOLOGY

The efficacy of compounds of the present invention as inhibitors of matrix metalloproteases can be evaluated and measured using pharmacological methods known in the art or as described in detail below based on similarly established methodologies.

1. Collagenase, and Stromelysin Inhibition Protocol

Inhibition of human fibroblast collagenase was determined using commercially available chromogenic substrate, Ac-Pro-Leu-Gly-thioesterLeu-Leu-Gly-OEt. Inhibition of human stromelysin was assayed with the fluorogenic peptide substrate, DNP-Pro-Lys-Pro-Gln-Gln-Phe-Lys-NMA, which is a modified form of substance P. Compounds were assessed for inhibitor potency by serial dilution in assay buffer (200 mM NaCl, 50 mM TRIS-HCl, 5 mM CaCl$_2$, 0.05% BRIJ, pH 7.6), addition of enzyme (2-5 nM), incubation for 10 minutes and initiation of the conversion of substrate. Percent inhibition was calculated at each inhibitor concentration and the data were plotted using standard curve fitting programs. IC$_{50}$ values were determined from these curves. Assays were run at low substrate concentration ($[S]<<K_m$) such that the calculated IC$_{50}$ values are equivalent to Ki within experimental error.

2. Gelatinase Inhibition Protocol

Inhibition of human 92 kDa gelatinase was determined using the fluorogenic substrate, DNP-Pro-Cha-Gly-C(Me)-His-Ala-Lys(e-NMA)-NH$_2$. Assays were run in black, 96 well microtiter plates at a total volume of 0.3 mL of buffer (50 mM TRIS-HCl, 200 mM NaCl, 5 mM CaCl, 0.05% Brij, pH 7.6) containing 0.1-0.3 nM enzyme. Inhibitors were titrated by serial dilution in consecutive wells. Assays were initiated with 10 uM substrate and the product formation was measured at EX/450 nM after 40 minutes. The percent inhibition was calculated at each concentration and IC$_{50}$ values were determined using standard curve fitting programs.

3. Metastases Model

The capacity of compounds of formula (I) to prevent experimental metastases was assessed in mice using the B16/F10 melanoma model according to the method described by T. Kanemoto et al., *Proc. Natl. Acad. Sci.*, USA, 87, 2279-2283 (1990).

4. Adjuvant Arthritis Model

The capacity of compounds of formula (I) to prevent adjuvant arthritis was tested in a rat adjuvant arthritis model according to the method described by J. N. Taurog et al, *J. Exp. Med.*, 162, 962-978 (1985).

5. Pharmaceutical Formulations and Doses

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a physiologically acceptable salt or solvate thereof together with one or more pharmaceutically acceptable carriers or excipients. The carrier(s) or excipient(s) must be acceptable in the sense of being compatable with the other ingredients of the formulation and not deleterious to the recipient thereof. According to another aspect of the invention, there is provided a process for the preparation of a pharmaceutical formulation comprising admixing a compound of formula (I) or a pharmaceutically acceptable salt or solvate thereof with one of more pharmaceutically acceptable carriers or excipients.

Compounds of formula (I) and physiologically acceptable salts and solvates thereof may be formulated for administration by any route, and the appropriate route will depend on the disease being treated. Suitable pharmaceutical formulations include those for oral, rectal, nasal, topical, (including buccal and sublingual), vaginal or parental (including intramuscular, subcutaneous, intravenous, and directly into the affected joint) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets, or tablets each containing a predetermined amount of the active ingredient; as a powder or granules; as a solution, a suspension or as an emulsion. The active ingredient may also be presented as a bolus, electuary, or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups, or elixirs, or may be presented as a dry product for constitution with water of other suitable vehicle before use. Such liquid preparations may contain conventional additives such as suspending agents, non-aqueous vehicles (which may include edible oils), or preservatives.

The compounds according to the invention may also be formulated for parental administration (e.g. by injection, for example bolus injection or continuous infusion) and may be presented in unit dose form in ampules, pre-filled syringes, small volume in fusion or in multi-dose containers with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form, obtained by aseptic isolation of sterile solid or by lyophilization from solution, for constitution with a suitable vehicle, e.g. sterile, pyrogen free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, suspending agents, thickening agents, or coloring agents. Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier. For topical administration to the eye, the compounds according to the invention may be made up in a solution or suspension in a suitable sterile aqueous or non-aqueous vehicle. Additives such as buffers (e.g. sodium metabisulphite or disodium edeate) and thickening agents such as hypromellose may also be included.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams, or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one or more dispersing agents, solubilizing agents, or suspending agents. Liquid sprays are conveniently delivered from pressurized packs.

For administration by inhalation the compounds according to the invention are conveniently delivered from an insufflator, nebulizer or a pressurized pack or other convenient means of delivering the aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin of blister packs from which the powder may be administered with the aid of an inhalator or insufflator.

When desired the above described formulations adapted to give sustained release of the active ingredient may be employed.

The pharmaceutical compositions according to the invention may also contain other active ingredients such as antimicrobial agents, or preservatives.

The compounds of the invention may also be used in combination with other therapeutic agents for example antiinfective agents such as bactericidal or fugicidal agents, antiinflammatory agents or anticancer agents.

The invention thus provides, in a further aspect, a combination comprising a compound of formula (I) or a physiologically acceptable derivative thereof together with another therapeutically active agent, in particular a bactericidal or fugicidal agent, an antiinflammatory agent or an anticancer agent.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. Suitable therapeutic agents for use in such combinations include tetracyclin and appropriate non-steroid and steroid antiinflammatory drugs and anticancer agents. The individual components of such combinations may be administered either sequentially or simultaneously in separate or combined pharmaceutical formulations. Appropriate doses of known therapeutic agents will be readily appreciated by those skilled in the art.

The amount of a compound of the invention required for use in treatment will of course vary not only with the particular compound selected but also with the route of administration, the nature of the condition being treated and the age and condition of the patient and will be ultimately at the discretion of the attendant physician or veterinarian. In general, however, a suitable dose will be in the range of from about 0.1 to 300 mg/kg of bodyweight per day, particularly from about 1 to 100 mg/kg of bodyweight per day. An appropriate dosage unit involved in oral administration may generally contain from about 1 to 250 mg, preferably from about 25 to 250 mg, of a compound of formula (I). The dosage employed for the topical administration will, of course, depend on the size of the area being treated. For the eyes each dose will be typically in the range of from 10 to 100 mg of the compound of formula (I).

For use in the treatment of rheumatoid arthritis the compounds of the invention can be administered by any of the aforementioned routes, particularly by the oral route or by injection. The daily dosage for a 70 kg mammal will be in the range of about 10 mg to 5 g of a compound of formula (I).

EXAMPLES

The following examples illustrate aspects of this invention but should not be construed as limitations thereto. As used herein the symbols and conventions used in these examples are consistant with those used in the contemporary scientific literature, for example, the Journal of the American Chemical Society. Specifically, the following abbreviation may be used in the examples and throughout the specification: g (grams); mg (milligrams); L (liters); mL (milliliters); psi (pounds per square inch); M (molar); mM (millimolar); i.v. (intravenous); Hz (Hertz); mol (moles); MeOH (methanol); DMF (N,N,-dimethylformamide); DMSO (dimethylsulfoxide); TFA (trifluoroacetic acid); THF (tetrahydrofuran); RT (room temperature); EtOAc (ethyl acetate); min (minutes); h (hours); M.p. (melting point); TLC (thin layer chromatography). Unless otherwise indicated, all temperatures are expressed in ° C. (degrees Centigrade). All references to ether are to diethyl ether. All reactions conducted at room temperature unless otherwise noted. Examples 41 and 42; 62 and 63; and 64 and 65 represent pairs of stereoisomers which were separated on the basis of R and S configurations but were not identified therein. Determination of the R and S isomers could be approached by stereoselective chemical methods, see "Advanced Organic Chemistry", Carey and Sundberg, third edition, Plenum Press, 1990, 596, or by analytical methods such as X-Ray chrystallography.

EXAMPLE A

4-Methyl-D-aspartate hydrochloride 210 mL methanol was slowly stirred and cooled to −10° C. and 31 mL thionyl chloride was added dropwise over 45 min. 40 g of D-Aspartic acid was added over 5 min and the reaction stirred for 3 h while warming to 21° C. 600 mL diethyl ether was added slowly and the mixture cooled to −10° C. The resulting solid was filtered, washed with 200 mL diethyl ether and dried in vacuo to afford the title compound as a white solid 33.4 g.

$[\alpha]D$ 15.7° (c=0.7; MeOH)

Analysis Found: C, 32.88; H, 5.40; N, 7.63%; $C_5H_9NO_4 \cdot HCl$ requires: C, 32.71; H, 5.49; N, 7.63%.

EXAMPLE B

N-[(Phenylmethoxy)carbonyl]-D-aspartic acid, 1-(1,1-dimethylethyl)-4-methyl ester 32 g of 4-Methyl-D-aspartate hydrochloride, prepared as described in Example A, was dissolved in a mixture of 250 mL water and 250 mL dioxane, and 92.4 g sodium carbonate was added slowly with stirring. 25 mL benzylchloroformate was added and the mixture stirred for 15 h at 23° C. 250 mL ethyl acetate was added and the mixture was acidified to pH2 with concentrated HCl. The organic phase was separated and the aqueous phase was extracted with 2×150 mL ethyl acetate. The combined organic layers were washed with brine, dried (MgSO$_4$) and evaporated. The residue was dissolved in 800 mL methylene chloride and treated with concentrated H$_2$SO$_4$. 200 mL isobutylene was condensed into the stirred mixture and the solution was left to stand for 15 h. The mixture was neutralized with sodium bicarbonate and the organic phase was washed with water and brine, dried (Na$_2$SO$_4$) and evaporated. The resulting oil was purified by silica chromatography using cyclohexane:ethyl acetate (4:1) as eluent to give the title compound as a clear oil; 31.8 g.

$[\alpha]D+14.04°$ (C+1.14; MeOH)

Analysis Found: C, 60.13; H, 7.06; N, 4.19%; C$_{17}$H$_{23}$NO$_6$ requires C, 60.52; H, 6.87; N, 4.15%.

EXAMPLE C

N-[(Phenylmethoxy)carbonyl]-D-aspartic acid, 1,1-dimethylethyl ester 31.3 g of N-[(phenylmethoxy)carbonyl]-D-aspartic acid, 1-(1,1-dimethylethyl)-4-methyl ester, prepared as described in Example B, in 120 mL methanol was treated with 120 mL 1N NaOH and the resulting yellow solution stirred at 21° C. for 2 h. The reaction mixture was concentrated in vacuo to about 30 mL and partitioned between 250 mL water and 250 mL ether. The aqueous layer was washed with 250 mL ether and layered with 250 mL additional ether. The mixture was stirred vigorously and acidified to pH2 with concentrated HCl. The organic layer was separated and the aqueous layer extracted with 250 mL ether. The combined extracts were washed with brine, dried (Na$_2$SO$_4$) and evaporated to give the title compound as a yellow oil; 29.4 g.

$[\alpha]D+11.6°$ (c=0.86; MeOH)

Analysis Found: C, 58.30; H, 6.63; N, 4.36; H20, 1.0%; C$_{16}$H$_{21}$NO$_6$.2H20 requires: C, 58.78; H, 6.60; N 4.28; H20, 1.1%.

EXAMPLE D

N-[(Phenylmethoxy)carbonyl]-D-homoserine, 1,1-dimethylethyl ester 29.23 g of N-[(phenylmethoxy)carbonyl]-D-aspartic acid, 1,1-dimethylethyl ester, prepared as in Example C, in 120 mL dry tetrahydrofuran at −10° C. was treated with 10 mL N-methylmorpholine. The mixture was stirred for 3 min and 8.7 mL ethylchloroformate was added dropwise. The mixture was warmed to 23° C. over 15 min and filtered. The filtrate was added dropwise over 30 min to a vigorously stirred mixture of 7.7 g sodium borohydride in 60 mL water at 3° C. The cooling bath was removed, the mixture stirred at 21° C. for 3 h, then cooled to 0° C. and acidified to pH2 with concentrated HCl. The mixture was extracted with 3×200 mL ethyl acetate and the combined organic extracts were washed with brine, dried (Na$_2$SO$_4$) and evaporated to furnish a clear oil. Purification by silica chromatography using methylene chloride-acetone (9:1) as eluent gave the title compound as a clear oil; 21.6 g.

$[\alpha]D+30.4°$ (c=1.81; MeOH)

Analysis Found: C, 62.12; H, 7.49; N, 4.53%; C$_{16}$H$_{23}$NO$_5$ requires: C, 61.75: H, 7.71; N, 4.52%

EXAMPLE E

N-[(Phenylmethoxy)carbonyl]-O-[1,1-dimethylethyl)-dimethylsilyl]-D-homoserine, 1,1-dimethylethyl ester 26 g of N-[(phenylmethoxy)carbonyl]-D-homoserine, 1,1-dimethylethyl ester, prepared as in Example D, in 300 mL dry dimethylformamide was treated with 5.72 g imidazole and then 12.7 g t-butyldimethylsilyl chloride and the mixture stirred at 21° C. for 18 h. The mixture was poured into 1000 mL of a mixture of 1:1 ethyl acetate-2N HCl and the organic phase was separated and washed with 2×300 mL 2N HCl. The combined aqueous phases were extracted with 2×250 mL ethyl acetate and the combined organic layers were washed with brine, dried (Na$_2$SO$_4$) and evaporated to give a clear oil. Purification by silica chromatography using 4:1 cyclohexane-ethyl acetate as eluent furnished gave the title compound as a clear oil; 20.93 g.

$[\alpha]D+28.26°$ (c=0.92; MeOH)

Analysis Found: C, 62.25; H, 9.08; N, 3.30%; C$_{22}$H$_{37}$NO$_5$Si requires: C, 62.37; H, 8.80; N, 3.31%.

EXAMPLE F

O-[(1,1-Dimethylethyl)dimethylsilyl]-D-homoserine, 1,1-dimethylethyl ester 26.2 g of N-[(phenylmethoxy)carbonyl]-O-[1,1-dimethylethyl)dimethylsilyl]-D-homoserine, 1,1-dimethylethyl ester, prepared as in Example E, in 200 mL ethanol was shaken with 2.7 g of 10% palladium on carbon in a hydrogen atmosphere (50%) at 21° C. for 3 h. The catalyst was removed by filtration through celite, and the solvent was evaporated to give the title compound as a clear oil; 17.3 g.

$[\alpha]^D-10.74°$ (c=1.21; MeOH)

EXAMPLE G 2-(R)-Hydroxy-4-methylpentanoic acid, phenylmethyl ester

A solution of 26.2 g D-leucine in 300 mL 1N sulphuric acid was cooled to 0° C. and treated dropwise with a solution of 25.5 g NaNO$_2$ in 50 mL water over 0.5 h. The mixture was stirred for 3 h at 0° C., allowed to warm up to 23° C. for 2 h and extracted with 3×100 mL ether. The combined organic layers were washed with 100 mL brine, dried (MgSO$_4$) and evaporated to afford a white solid. This was dissolved in 200 mL methanol and treated with a solution of 6.5 g sodium hydroxide in 35 mL water. After 5 min the organic solvent was evaporated and the resulting aqueous solution was lyophilized overnight. The resulting solid was slurried in 400 mL DMF and treated with 20 mL benzylbromide. The mixture was stirred at 23° C. for 18 h and the solvent removed by evaporation. The residue was treated with 200 mL 2N HCl and extracted with 3×150 mL ethyl acetate. The combined organic layers were washed with aqueous sodium bicarbonate, water, dried(MgSO$_4$) and evaporated to give the title compound as a light golden oil; 32.6 g.

$[\alpha]^D+15.2°$ (c=1.3; CHCl$_3$)

Analysis Found: C, 69.88; H, 8.43%; C$_{13}$H$_{18}$O$_3$ requires: C, 70.24; H, 8.16%.

EXAMPLE H

N-[(R)-1-[(1,1-Dimethylethoxy)carbonyl]-3-[[(1,1-dimethylethyl)dimethylsilyl]oxy]propyl]-L-leucine, phenylmethyl ester 7.4 g of 2-(R)-hydroxy-4-methylpentanoic acid, phenylmethyl ester, prepared as in Example G, in 100 mL dry methylene chloride was added to a 0° C. solution of 9.4 g trifluoromethanesulfonic anhydride in 100 mL dry methylene chloride. 7.14 g of 1,8,-Bis(dimethylamino)-naphthalene was added and the resulting orange mixture stirred at 0° C. for 30 min. A solution of 9.65 g of O-[(1,1-Dimethylethyl)dimethylsilyl]-D-homoserine, 1,1-dimethylethyl ester, prepared as in Example F, in 90 mL dry dioxane was added dropwise along with 7.14 g of 1,8,-Bis(dimethylamino)naphthalene and the mixture stirred at 21° C. for 15 h. The mixture was filtered and the filtrate was diluted with 300 mL ethyl acetate, washed with 2×200 mL water, 250 mL brine, dried (Na2SO4) and evaporated to give a brown oil. Purification by silica chromatography using 9:1 cyclohexane-ether as eluent gave the title compound as a yellow oil; 11.92 g.

[α]D −8.1° (c=0.99;CHCl3)
Analysis Found: C, 65.47; H, 9.78; N, 2.78%; $C_{27}H_{47}NO_5Si$ requires: C, 65.70: H, 9.60; N, 2.80%.

EXAMPLE I

N-(R)-1-[(1,1-Dimethylethoxy)carbonyl]-3-[[(1,1-dimethylethyl)dimethylsilyl]oxy]propyl]-L-leucine 1.11 g of N-[(R)-1-[(1,1-dimethylethoxy)carbonyl]-3-[[(1,1-dimethylethyl)dimethylsilyl]oxy]propyl-L-leucine, phenylmethyl ester, prepared as in Example H, in 25 mL ethanol was treated with 120 mg of 10% palladium on carbon and the mixture shaken in a hydrogen atmosphere (40 psi) for 2 h. The catalyst was removed by filtration through celite and the solvent was evaporated to give the title compound as a yellow oil; 950 mg.

EXAMPLE J

N-[(R)-1-[(1,1-Dimethylethoxy)carbonyl]-3-hydroxypropyl]-L-leucine, phenylmethyl ester 5 g of N-[(R)-1-[(1,1-dimethylethoxy)carbonyl]-3-[[(1,1-dimethylethyl)dimethylsilyl]oxy]propyl-L-leucine, phenylmethyl ester, prepared as in Example H, in 100 mL acetic acid and 15 mL water was heated at 45° C. for 4 h. The solvents were evaporated and the residue dissolved in 100 mL ethyl acetate and washed with aqueous bicarbonate solution. The organic layer was dried (MgSO4) and evaporated. The residue was purified by silica chromatography using 10% ethyl acetate-hexane as eluent to give the title compound as an amber oil; 2.5 g.

1H-NMR (CDCl3) δ 7.35 (m, 5H), 5.12 (AB system, 2H), 3.79 (t, J=5.2 Hz, 2H), 3.35 (m, 2H), 2.00–1.50 (m, 7H). 1.44 (s, 9H), 0.89 (d, J=6.6 Hz, 6H).

EXAMPLE K

N-[(R)-1-[(1,1-Dimethylethoxy)carbonyl]-3-(1,3-dihydro-1,3-dioxo-2H-benz[f]isoindol-2-yl)propyl]-L-leucine, phenylmethyl ester 2.5 g of N-[(R)-1-[(1,1-dimethylethoxy)carbonyl]-3-hydroxypropyl]-L-leucine, phenylmethyl ester, prepared as in Example J, 1.85 g triphenylphosphine, and 1.4 g 1,3-dihydro-1,3-dioxo-2H-Benz[f]isoindole in 100 mL dry tetrahydrofuran was cooled to 0° C. and treated with 1.1 mL diethylazidodicarboxylate. The resulting mixture was allowed to warm up to 23° C. over 24 h and the solvent removed by evaporation. The residue was purified by silica chromatography using methylene chloride as eluent to give a light yellow solid. Trituration with 20 mL methanol and filtration gave the title compound as a white solid which crystallized from methanol; 1.9 g.

M.p. 136°–7° C.

1H-NMR (CDCl3) δ 8.32 (s, 2H), 8.04 (m, 2H), 7.69 (m, 2H), 7.33 (m, 5H), 5.10 (AB system, Jab=12.4 Hz, 2H), 3.87 (m, 2H), 3.38 (t, J=7.0 Hz, 1H), 3.22 (dd, J=5.1 Hz, J=6.3 Hz, 1H), 2,25 (br s, 1H), 2.10–1.70 (m, 5H), 1.47 (s, 9H), 0.90 (d, J=6.6 Hz, 6H).

Analysis Found: C, 70.79; H, 6.87; N, 4.98%; $C_{33}H_{38}N_2O_6$ requires: C, 70.95; H, 6.86; N, 5.01%.

EXAMPLE L

N-[(R)-1-[(1,1-Dimethylethoxy)carbonyl]-3-(1,3-dihydro-1,3-dioxo-2H-benz[f]isoindol-2-yl)propyl]-L-leucine 1.9 g of N-[(R)-1-[(1,1-dimethylethoxy)carbonyl]-3-(1,3-dihydro-1,3-1,3-dioxo-2H-benz[f]isoindol-2-yl)propyl]-L-leucine, phenylmethyl ester, prepared as in Example K, in 50 mL ethyl acetate was shaken with 500 mg of 10% palladium on carbon in a hydrogen atmosphere (50 psi) for 24 h. The catalyst was removed by filtration through celite and the solvent evaporated. The residue was purified by silica chromatography using 50% ethyl acetate-hexane as eluent to give the title compound as a cream solid which was crystallized from ethyl acetate-hexane; 1.5 g.

M.p. 168°–9° C. 1H-NMR (CDCl3) δ 8.34 (s, 2H), 8.05 (m, 2H), 7.70 (m, 2H), 3.87 (m, 2H), 3.31 (m, 2H), 2.20–1.60 (m, 5H), 1.46(s, 9H), 0.95 (d, J=6.6 Hz, 6H).

Analysis Found: C, 66.58; H, 6.90; N, 5.98%; $C_{26}H_{32}N_2O_5$ requires: C, 66.65; H, 6.88; N, 5.98%.

EXAMPLE M 2-(R)-[[3-methyl-1-(S)-[(benzylamino)carbonyl]butyl]amino]-4-[((1,1-dimethylethyl)dimethylsilyl)oxy]-butanoic acid-1,1-dimethylethyl ester 11.4 g of N-[(R)-1-[(1,1-dimethylethoxy)carbonyl]-3-[[(1,1-dimethylethyl)dimethylsilyl]oxy]propyl-L-leucine, prepared as in Example I, 3.64 g benzylamine, and 4.59 g hydroxybenzotriazole in 150 mL DMF was sparged with nitrogen for 10 min. 7.02 g of d icyclohexylcarbodiimide in 50 mL DMF was added dropwise at 0° C. The mixture was stirred for 15 h at 23° C., filtered, and the solvents were removed by evaporation. The residue was purified by silica chromatography using 80% hexane-ethyl acetate as eluent to give the title compound as a brown oil; 8.8 g.

1H-NMR (CDCl3): δ 7.30 (m, 5H), 4.46(m, 2H), 3.72 (m, 2H), 3.30 (m, 1H), 3.20 (m, 1H), 1.60–1.92 (m, 5H), 1.38 (s, 9H), 0.89 (dd, 6H), 0.88 (s, 9H), 0.04 (s, 6H).

EXAMPLE N 2-(R)-[[3-methyl-1-(S)-[(benzylamino)carbonyl]butyl]amino]-4-(hydroxy)-butanoic acid-1,1-dimethylethyl ester 8.8 g of 2-(R)-[[3-methyl-1-(S)-[(benzylamino)carbonyl]butyl]amino]-4-[((1,1-dimethylethyl)dimethylsilyl)oxy]-butanoic acid-1,1-dimethylethyl ester, prepared as in Example M, in 300 mL acetic acid was stirred for 24 h at 45° C. and the solvent was removed by evaporation. The residue was dissolved in 300 mL ethyl acetate, washed with 3×100 mL sodium bicarbonate, dried (MgSO4), filtered, and the solvents were removed by evaporation. The residue was purified by silica chromatography using methylene chloride:acetone (2:1) as eluent to give the title compound; 5.9 g.

1H-NMR (CDCl3): δ 7.31 (m, 5H), 4.41 (m, 2H), 3.75 (t, 2H), 3.32 (t, 1H), 3.23 (m, 1H), 1.86 (M, 2H), 1.50–1.88 (m, 3H), 1.41 (s, 9H), 0.91 (dd, 6H).

EXAMPLE O 2-(R)-[[3-methyl-1-(S)-[((pyridin-3-yl-methyl)amino)-carbonyl]butyl]amino]-4-[((1,1-dimethylethyl)dimethylsilyl)oxy]-butanoic acid-1,1-dimethylethyl ester 0.598 g hydroxybenzotriazole was added to 1.41 g of N-[(R)-1-[(1,1-dimethylethoxy)carbonyl]-3-[[(1,1-dimethylsilyl]oxy]propyl]-L-leucine, prepared as in Example I, in 37 mL DMF, followed by 0.478 g of aminomethylpyridine, then 0.913 g dicyc lohexylcarbodiimide, at 0° C. The mixture was stirred at 23° C. for 72 h, filtered, and the solvent was removed by evaporation. The residue was purified by silica chromatography using methylene chloride:acetone (4:1) to give the title compound; 1.18 g.

[α]D −12.00° (c=0.400; MeOH)
MS (FAB) MH+ =494

EXAMPLE P 2-(R)-[[3-methyl-1-(S)-[((pyridin-3-yl-methyl)amino)-carbonyl]butyl]amino]-4-(hydroxy)-butanoic acid-1,1-dimethylethyl ester 1.18 g of 2-(R)-[[3-methyl-1-(S)-[((pyridin-3-yl-methyl)amino)carbonyl]butyl]amino]-4-[((1,1-dimethylethyl)dimethylsilyl)oxy]-butanoic acid-1,1-dimethylethyl ester, prepared as in Example O, was added to 48 mL of acetic acid:water (9:1) and the mixture was heated to 45° C. and stirred 16 h. The solvents were removed by evaporation and the residue was dissolved in ethyl acetate, washed with saturated sodium bicarbonate, dried (MgSO4). The solvent was removed by evaporation and the residue was purified by silica chromatography using acetone:methylene chloride (1:1) as eluents to give the title compound; 0.513 g.

[α]D −5.47° (c=1.060; CHCl3)
MS (FAB) MH+ =380.

Specific Compounds

Specific examples of compounds of the present invention are those of the formula (I), prepared according to the procedure described in Scheme 1 wherein a compound of the formula (III) is prepared as in Example L, where
R1 is isobutyl;
R4R5 together form benzene;
Rp is 1,1-dimethylethyl.

EXAMPLE 1

4-(1,3-Dihydro-1,3-dioxo-2H-benz[f]isoindol-2-yl)-2-(R)-[[3-methyl-1-(S)-[[(2-morpholin-4-ylethyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(2-morpholin-4-ylethyl)amino]carbonyl]butyl]amino]-butanoicacid-1,1-dimethylethyl ester 200 mg of N-[(R)-1-[(1,1-dimethylethoxy)carbonyl]-3-(1,3-dihydro-1,3-dioxo-2H-benz[f]isoindol-2-yl)propyl]-L-leucine, prepared as in Example L, was added to a stirred mixture of 0.044 mL 2-Morpholin-4-ylethylamine, 0.174 mL diisopropylethylamine, and 1 mL DMF at 0° C. 1.1 mL of 0.45M hydroxybenzotriazol-benzotriazoltetramethyluronium hexafluorophosphate in DMF was added. The mixture was warmed to 20° C. with stirring for 18 h, diluted with 30 mL ethyl acetate, washed two times with 20 mL of 10% sodium carbonate, washed with 20 mL brine, and dried with sodium sulfate. The solvents were removed by evaporation to give the title compound as an oil; 240 mg.

(b) 4-(1,3-Dihydro-1,3-dioxo-2H-benz[f]isoindol-2-yl)-2-(R)-[[3-methyl-1-(S)-[[(2-morpholin-4-ylethyl)amino]carbonyl]butyl]amino]-butanoic acid 240 mg of 4-(1,3-dihydro-1,3-dioxo-2H-benz[f]isoindol-2-yl)-2-[[3-methyl-1-[[(2-morpholin-4-yl-ethyl)amino]carbonyl]butyl]amino]-butanoic acid-1,1-dimethylethyl ester from part (A), was dissolved in TFA:H2O (9:1) and allowed to stand for 20 h. The solvents were removed by evaporation, and the resulting oil was purified by reverse phase H.P.L.C. The solvents were removed by lyopholization to give the title compound as a white solid; 145 mg.

High Resolution MS; m/e Found: 525.2686
1H-NMR (CD3OD) δ 8.31 (2H, s), 8.08 (2H, m), 7.66 (2H, m), 4.00–3.70 (8H, m), 3.67 (1H, t,), 3.56 (1H, dd), 3.25–3.15 (8H, m), 2.20 (2H, m), 1.80 (1H, m), 1.66 (1H, m), 1.50 (1H, m), 0.90 (6H, t).

EXAMPLE 2

4-(1,3-Dihydro-1,3-dioxo-2H-benz[f]isoindol-2-yl)-2-(R)-[[3-methyl-1-(S)-[[methylamino]carbonyl]butyl]amino]-butanoic acid (a) 4-(1,3-Dihydro-1,3-dioxo-2H-benz[f]isoindol-2-yl)-2-(R)-[[3-methyl-1-(S)-[[methylamino]carbonyl]butyl]amino]-butanoic acid-1,1-dimethylethyl ester 300 mg of N-[(R)-1-[(1,1-dimethylethoxy)carbonyl]-3-(1,3-dihydro-1,3-dioxo-2H-benz[f]isoindol-2-yl)propyl]-L-leucine, prepared as in Example L, was added to 120 mg of hydroxybenzotriazol.H2O, 150 mg of dicyclohexylcarbodiimide, 600 mg methylamine-hydrochoride, and 30 mL dichloromethane. 0.5 ; mL triethylamine was added and the mixture was stirred for 18 h. The mixture was filtered through celite and the solvent was removed by evaporation. The resulting residue was purified by silica chromatography using hexane:ethyl acetate:dichloromethane (2:1:1) as eluent to give the title compound as a white solid; 320 mg.

(b) 4-(1,3-Dihydro-1,3-dioxo-2H-benz[f]isoindol-2-yl)-2-(R)-[[3-methyl-1-(S)-[[methylamino]carbonyl]butyl]amino]-butanoic acid Prepared as described for Example 1, Part (b) by hydrolysis of the product of Part (a) above to give the title compound as a white powder; 190 mg.

MS; MH+ =426
1H-NMR (CD3OD) δ 8.11 (2H, s), 7.86 (2H, m), 7.45 (2H, m), 3.65 (3H, m), 3.52 (1H, m), 2.00 (2H, m), 1.6–1.2 (3H, m), 0.69 (6H, m).

EXAMPLE 3

4-(1,3-Dihydro-1,3-dioxo-2H-benz[f]isoindol-2-yl)-2-(R)-[[3-methyl-1-(S)-[[(1H-imidazol-2-ylmethyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(1H-imidazol-2-ylmethy)amino]carbonyl]butyl]amino]-butanoic acid-1,1-dimethylethyl ester 50 mg of N-[(R)-1-[(1,1-dimethylethoxy)carbonyl]-3-(1,3-dihydro-1,3-dioxo-2H-benz[f]isoindol-2-yl)propyl]-L-leucine, prepared as in Example L, was added to 40 mg N-hydroxysuccinimide in 5 mL DMF. To the mixture was added 27 mg of (1H-Imidazo-2-ylmethyl)amine followed by 1 mL triethylamine. The mixture was stirred for 18 h, filtered through celite, and the solvents were removed by evaporation. The resulting residue was purified by reverse phase H.P.L.C. to afford the title compound as a white solid; 44 mg.

(b)  4-(1,3-Dihydro-1,3-dioxo-2H-benz[f]isoindol-2-yl)-2-(R)-[[3-methyl-1-(S)-[[(1H-imidazol-2-ylmethyl)amino]carbonyl]butyl]amino]-butanoic acid Prepared as described for Example 1, Part (b) by hydrolysis of the product of Part (A) above to afford the title compound as a white powder; 16.7 mg.

High Resolution MS; m/e Found: 492.2260

$^1$H-NMR (CD$_3$OD) δ 8.20 (2H, m), 8.00 (2H, m), 7.60 (2H, m), 7.40 (2H, m), 3.80 (4H, m), 2.20 (2H, m), 1.80–1.60 (3H, m), 0.90 (6H, d).

EXAMPLE 4

4-(1,3-Dihydro-1,3-dioxo-2H-benz[f]isoindol-2-yl)-2-(R)-[[3-methyl-1-(S)-[[(1H-tetrazol-5-ylmethyl)amino]carbonyl]butyl]amino]-butanoic acid (a)  4-(1,3-Dihydro-1,3-dioxo-2H-benz[f]isoindol-2-yl)-2-(R)-[[3-methyl-1-(S)-[[(1H-tetrazol-5-ylmethyl)amino]carbonyl]butyl]amino]-butanoic acid-1,1-dimethylethyl ester 50 mg of N-[(R)-1-[(1,1-dimethylethoxy)carbonyl]-3-(1,3-dihydro-1,3-dioxo-2H-benz[f]isoindol-2-yl)propyl]-L-leucine, prepared as in Example L, was added to of 40 mg N-hydroxysuccinamide in 5 mL DMF. 150 mg of dicyclohexylcarbodiimide was added and the mixture was stirred for 1 h. 43 mg of (1H-Tetrazol-5-ylmethyl)amine dihydrochloride was added followed by 1 mL triethylamine. The mixture was stirred for 18 h, filtered through celite, and the solvents removed by evaporation. The resulting residue was purified by reverse phase H.P.L.C. to give the title compound as a white solid; 18 mg.

(b)  4-(1,3-Dihydro-1,3-dioxo-2H-benz[f]isoindol-2-yl)-2-(R)-[[3-methyl-1-(S)-[[(1H-tetrazol-5-ylmethyl)amino]carbonyl]butyl]amino]-butanoic acid Prepared as described for Example 1, Part (b) by hydrolysis of the product of Part (a) above to give the title compound as a white powder; 3.2 mg.

MS; MH$^+$ =494

$^1$H-NMR (DMSO-d6) δ 8.30 (2H, br s), 8.10 (2H, br s), 7.60 (2H, br s), 4.60 (1H, m), 3.90–3.80 (3H, m), 3.60 (2H, m), 2.20 (2H, m), 1.80–1.60 (4H, m), 0.90 (6H, br).

EXAMPLE 5

4-(1,3-Dihydro-1,3-dioxo-2H-benz[f]isoindol-2-yl)-2-(R)-[[3-methyl-1-(S)-[[[2-(phenyl)ethyl]amino]carbonyl]butyl]amino]-butanoic acid (a)  4-(1,3-Dihydro-1,3-dioxo-2H-benz[f]isoindol-2-yl)-2-(R)-[[3-methyl-1-(S)-[[[2-(phenyl)ethyl]amino]carbonyl]butyl]amino]-butanoic acid-1,1-dimethylethyl ester ester 100 mg of N-[(R)-1-[(1,1-dimethylethoxy)carbonyl]-3-(1,3-dihydro-1,3-dioxo-2H-benz[f]isoindol-2-yl)propyl]-L-leucine, prepared as in Example L, was added to 2.5 mL of DMF. 39.2 mg of hydroxybenzotriazol.H2O was added to the mixture followed by 0.032 mL phenylethylanine. The mixture was cooled to 0° C. 52.8 mg dicyclohexylcarbodiimide was added and the mixture was stirred for 24 h. The solvents were removed by evaporation and the resultant residue was diluted with ethyl acetate. The mixture was washed with a saturated solution of sodium bicarbonate and the organic layer was separated, dried (MgSO$_4$) and filtered. The solvent was removed by evaporation to afford the title compound; 120 mg.

(b)  4-(1,3-Dihydro-1,3-dioxo-2H-benz[f]isoindol-2-yl)-2-(R)-[[3-methyl-1-(S)-[[[2-(phenyl)ethyl]amino]carbonyl]butyl]amino]-butanoic acid Prepared as described for Example 1, Part (b) by hydrolysis of the product of Part (a) above to give the title compound as a colorless solid; 53 mg. MS; MH$^+$ =516.2502

$^1$H-NMR (CD$_3$OD) δ 8.40(2H,S), 8.10–8.20 (2H,m), 7.70–7.80 (2H,m), 7.10–7.30 (5H,m), 3.80–4.00 (2H,m), 3.50–2.70 (3H,m), 3.40–3.50 (1H,m), 2.80–2.90 (2H,m), 2.10–2.30 (2H,m), 1.80–1.10 (5H,m), 0.80 (6H,d, J=6 Hz).

EXAMPLE 6

4-(1,3-Dihydro-1,3-dioxo-2H-benz[f]isoindol-2-yl)-2-(R)-[[3-methyl-1-(S)-[[(pyridin-3-ylmethyl)amino]carbonyl]butyl]amino]-butanoic acid (a)  4-(1,3-Dihydro-1,3-dioxo-2H-benz[f]isoindol-2-yl)-2-(R)-[[3-methyl-1-(S)-[[(pyridin-3-ylmethyl)amino]carbonyl]butyl]amino]-butanoic acid-1,1-dimethylethyl ester 100 mg of N-[(R)-1-[(1,1-dimethylethoxy)carbonyl]-3-(1,3-dihydro-1,3-dioxo-2H-benz[f]isoindol-2-yl)propyl]-L-leucine, prepared as in Example L, was added to 2.5 mL of DMF. 39.2 mg of hydroxybenzotriazol.H$_2$O was added to the mixture followed by 0.026 mL of (pyridin-3-ylmethyl)amine. The mixture was cooled to 0° C. and 52.8 mg dicyclohexylcarbodiimide was added. The mixture was warmed to 23° C. and stirred for 24 h. The solvents were removed by evaporation and the resultant residue was diluted with ethyl acetate. The mixture was extracted with a saturated solution of sodium bicarbonate and the organic layer was separated, dried (MgSO$_4$), and filtered. The solvent was removed by evaporation to afford the title compound; 139 mg.

(b)  4-(1,3-Dihydro-1,3-dioxo-2H-benz[f]isoindol-2-yl)-2-(R)-[[3-methyl-1-(S)-[[(pyridin-3-ylmethyl)amino]carbonyl]butyl]amino]-butanoic acid Prepared as described for Example 1, Part (b) by hydrolysis of the product of Part (a) above to give the title compound as a colorless solid; 97 mg. MS; MH$^+$ =503.2295

$^1$H-NMR (CD$_3$OD) δ 8.75 (1H, S broad), 8.63 (1H,m) 8.40 (2H,S), 8.30 (1H,m), 8.15 (2H,m), 7.70–7.90 (3H,m), 4.6 (2H, ABq), 3.90–4.00 (2H,m), 3.80–3.90 (2H,m), 1.60–1.85 (4H,m), 0.95 (6H, apparent t, J=6 Hz).

EXAMPLE 7

4-(1,3-Dihydro-1,3-dioxo-2H-benz[f]isoindol-2-yl)-2-(R)-[[3-methyl-1-(S)-[[(2-methyl-2H-tetrazol-5-ylmethyl)amino]carbonyl]butyl]amino]-butanoic acid (a)  4-(1,3-Dihydro-1,3-dioxo-2H-benz[f]isoindol-2-yl)-2-(R)-[[3-methyl-1-(S)-[[(2H-tetrazol-5-ylmethyl)amino]carbonyl]butyl]amino]-butanoic acid-1,1-dimethylethyl ester 100 mg of N-[(R)-1-[(1,1-dimethylethoxy)carbonyl]-3-(1,3-dihydro-1,3-dioxo-2H-benz[f]isoindol-2-yl)propyl]-L-leucine, prepared as in Example L, was added to 2 mL DMF. 39.2 mg of hydroxybenzotriazol.H$_2$O was added to the mixture, followed by 28.2 mL of N-methyl-4-morpholine and 38.3 mg of (2-methyl-2H-tetrazo-5-ylmethyl)amine The mixture was cooled to 0° C. and 52.8 mg of dicyclohexylcarbodiimide was added. The mixture was allowed to warm to 23° C. and was stirred for 24 h. The solvents were removed by evaporation and the resultant residue was diluted with ethyl acetate. The mixture was extracted with a saturated solution of sodium bicarbonate and the organic layer was separated, dried (MgSO$_4$), and filtered. The solvent was removed by evaporation to afford the title compound; 120 mg.

(b) 4-(1,3-Dihydro-1,3-dioxo-2H-benz[f]isoindol-2-yl)-2-(R)-[[3-methyl-1-(S)-[[(2-methyl-2H-tetrazol-5-ylmethyl)amino]carbonyl]butyl]amino]-butanoic acid Prepared as described for Example 1, Part (b) by hydrolysis of the product of Part (b) above to give the title compound as a colorless solid; 50 mg.

MS; MH+ =508.2307

$^1$H-NMR (CD$_3$OD) δ 8.25 (2H, s), 8.00–8.10 (2H, m), 7.60–7.65 (2H, m), 4.55 (2H, s), 4.20 (3H, s), 3.70–3.90 (4H, m), 2.10–2.30 (2H, m), 1.50–1.80 (3H, m) 0.85 (6H, apparent t, J=6 Hz).

EXAMPLE 8

4-(1,3-Dihydro-1,3-dioxo-2H-benz[f]isoindol-2-yl)-2-(R)-[[3-methyl-1-(S)-[[(4-hydroxy-2-methyl-pyrimidin-5-ylmethyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(4-hydroxy-2-methyl-pyrimidin-5-ylmethyl)amino]carbonyl]butyl]amino]-butanoic acid-1,1-dimethylethyl ester Prepared as described for Example 7, Part (a), using 5-aminomethyl-2-methyl-pyridin-4-ol as HNR$^2$R$^3$ to give the title compound as a yellow oil; 80 mg.

(b) 4-(1,3-Dihydro-1,3-dioxo-2H-benz[f]isoindol-2-yl)-2-(R)-[[3-methyl-1-(S)-[[(4-hydroxy-2-methyl-pyrimidin-5-ylmethyl)amino]carbonyl]butyl]amino]-butanoic acid Prepared as described for Example 1, Part (b) by hydrolysis of the product of Part (a) above to give the title compound as a colorless solid; 8 mg.

MS; MH+ =534

$^1$H-NMR (CD$_3$OD) δ 8.30 (2H,s), 8.00–8.10 (2H, m), 7.80 (1H, s), 7.60–7.70 (2H, m), 4.10 (2H, ABq), 3.90–4.00 (1H, m), 3.70–3.80 (3H, m), 2.40 (3H, s), 2.10–2.20 (2H, m), 1.60–1.80 (1H, m), 1.40–1.60 (2H, m), 0.70–0.90 (6H, m).

EXAMPLE 9

4-(1,3-Dihydro-1,3-dioxo-2H-benz[f]isoindol-2-yl)-2-(R)-[[3-methyl-1-(S)-[[[2-(2-pyridin-3-yl)ethyl]amino]carbonyl]butyl]amino]-butanoic acid (a) 4-(1,3-Dihydro-1,3-dioxo-2H-benz[f]isoindol-2-yl)-2-(R)-[[3-methyl-(S)-1-[[[2-(2-pyridin-3-yl)ethyl]amino]carbonyl]butyl]amino]-butanoic acid-1,1-dimethylethyl ester Prepared as described for Example 7, Part (a), using 2-pyridin-3-ylethylamine as HNR$^2$R$^3$ to afford the title compound as a tan oil; 100 mg.

(b) 4-(1,3-Dihydro-1,3-dioxo-2H-benz[f]isoindol-2-yl)-2-(R)-[[3-methyl-1-(S)-[[[2-(2-pyridin-3-yl)ethyl]amino]carbonyl]butyl]amino]-butanoic acid Prepared as described for Example 1, Part (b) by hydrolysis of the product of Part (a) above to give the title compound as a colorless solid; 37 mg. MS; MH+ =517 $^1$H-NMR (CD$_3$OD) δ 8.55 (1H, M), 8.28 (2H, s), 8.10–8.20 (1H, m), 8.00–8.10 (2H, m) 7.55–7.70 (4H, m), 3.70–3.90 (3H, m) 3.50–3.70 (2H, m), 3.40–3.50 (1H, m), 3.00–3.10 (2H, m) 2.10–2.20 (2H, m), 1.50–1.70 (2H, m), 1.30–1.50 (1H, m), 0.80 (6H, d, J=6.0 Hz).

EXAMPLE 10

4-(1,3-Dihydro-1,3-dioxo-2H-benz[f]isoindol-2-yl)-2-(R)-[[3-methyl-1-(S)-[[1-(1H-tetrazol-5-yl)ethyl]amino]-carbonyl]butyl]amino]-butanoic acid (a) 4-(1,3-Dihydro-1,3-dioxo-2H-benz[f]isoindol-2-yl)-2-(R)-[[3-methyl-1-(S)-[[1-(1H-tetrazol-5-yl)ethyl]amino]carbonyl]butyl]amino]-butanoic acid-1,1-dimethylethyl ester 100 mg of N-[(R)-1-[(1,1-dimethylethoxy)carbonyl]-3-(1,3-dihydro-1,3-dioxo-2H-benz[f]isoindol-2-yl)propyl]-L-leucine, prepared as in Example L, was added to 1 mL DMF. 39 mg of hydroxybenzotriazol.H$_2$O was added followed by 29 mg of 1-(1H-tetrazol-5-yl)ethyl)amine and 53 mg of dicyclohexylcarbodiimide. The mixture was stirred for 24 h, diluted with dichloromethane, and the solvents were removed by evaporation to give a tan solid. The solid was dissolved in 5 mL acetonitrile, and filtered. The solvents were partially removed by evaporation. The resulting mixture of 2 mL was purified by reverse phase H.P.L.C. to afford the title compound as a white solid; 103 mg.

(b) 4-(1,3-Dihydro-1,3-dioxo-2H-benz[f]isoindol-2-yl)-2-(R)-[[3-methyl-1-(S)-[[1-(1H-tetrazol-5-yl)ethyl]amino]carbonyl]butyl]amino]-butanoic acid Prepared as described for Example 1, Part (b) by hydrolysis of the product of Part (a) above to give the title compound as a white powder; 50 mg.

MS; MH+ =508

$^1$H-NMR (CD$_3$OD) δ 8.25 (2H, s), 8.00–8.10 (2H, m), 7.59–7.69 (2H, m), 5.23–5.33 (1H, m), 3.60–3.90 (7H, m), 2.10–2.22 (2H, m), 1.40–1.80 (3H, m), 0.64–0.95 (6H, m).

EXAMPLE 11

4-(1,3-Dihydro-1,3-dioxo-2H-benz[f]isoindol-2-yl)-2-(R)-[[3-methyl-1-(S)-[[(5-amino-4H-[1,2,4]-triazol-3-ylmethyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(5-amino-4H-[1,2,4]-triazol-3-ylmethyl)amino]carbonyl]butyl]amino]-butanoic acid-1,1-dimethylethyl ester Prepared as described for Example 7, Part (a) using (5-amino-4H-[1,2,4]-triazol-3-ylmethyl)amine as HNR$^2$R$^3$ to give the title compound as a tan solid; 181 mg.

(b) 4-(1,3-Dihydro-1,3-dioxo-2H-benz[f]isoindol-2-yl)-2-(R)-[[3-methyl-1-(S)-[[(5-amino-4H-[1,2,4]-triazol-3-ylmethyl)amino]carbonyl]butyl]amino]-butanoic acid Prepared as described for Example 1, Part (b) by hydrolysis of the product of Part (a) above to give the title compound as a white solid; 33 mg.

MS; MH+ =508

$^1$H-NMR (CD$_3$OD) δ 8.20–8.40 (2H, m), 795–8.10 (2H, m), 7.50–7.70 (2H, m), 4.20–4.650 (2H, m), 3.60–4.00 (4H, m), 2.10–2.40 (2H, m), 1.40–1.80 (3H, m), 0.60–1.00 (6H, m).

EXAMPLE 12

4-(1,3-Dihydro-1,3-dioxo-2H-benz[f]isoindol-2-yl)-2-(R)-[[3-methyl-1-(S)-[[[1-(6-oxo-1,6-dihydro-pyridazin-3-yl)ethyl]amino]carbonyl]butyl]amino]-butanoic acid (a) 4-(1,3-Dihydro-1,3-dioxo-2H-benz[f]isoindol-2-yl)-2-(R)-[[3-methyl-(S)-1-[[[1-(6-oxo-1,6-dihydropyridazin-3-yl)ethyl]amino]carbonyl]butyl]amino]-butanoic acid-1,1-dimethylethyl ester Prepared as described for Example 7, Part (a) using 6-(1-aminoethyl)-3-(2H)-pyridazinone as HNR²R³ to afford the title compound as a tan solid; 183 mg.

(b) 4-(1,3-Dihydro-1,3-dioxo-2H-benz[f]isoindol-2-yl)-2-(R)-[[3-methyl-1-(S)-[[[1-(6-oxo-1,6-dihydropyridazin-3-yl)ethyl]amino]carbonyl]butyl]amino]-butanoic acid Prepared as described for Example 1, Part (b) by hydrolysis of the product of Part (a) above to give the title compound as a white powder; 54 mg. MS; MH+ = 534

¹H-NMR (CD₃OD) δ 8.30 (2H, s), 8.02–8.07 (2H, m), 7.61–7.67 (2H, m), 7.44 (1H, d, J=9 Hz), 7.33 (1H, d, J=9 Hz), 6.81–6.88 (2H, m), 4.93 (1H, m), 3.70–3.93 (4H, m), 2.10–2.25 (2H, m), 1.45–1.80 (3H, m), 1.30–1.40 (3H, m), 0.75–0.95 (6H, m).

EXAMPLE 13

4-(1,3-Dihydro-1,3-dioxo-2H-benz[f]isoindol-2-yl)-2-(R)-[[3-methyl-1-(S)-[[(phenyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(phenyl)amino]carbonyl]butyl]amino]-butanoic acid-1,1-dimethylethyl ester Prepared as described for Example 10, Part (a) using phenylamine as HNR²R³ to afford the title compound as a white solid; 69 mg.

(b) 4-(1,3-Dihydro-1,3-dioxo-2H-benz[f]isoindol-2-yl)-2-(R)-[[3-methyl-1-(S)-[[(phenyl)amino]carbonyl]butyl]amino]-butanoic acid Prepared as described for Example 1, Part (b) by hydrolysis of the product of Part (a) above to give the title compound as a white solid; 56 mg.

MS; MH+ = 488

¹H-NMR (CD₃OD) δ 8.20 (2H, s), 7.98–8.03 (2H, m), 7.61–7.67 (2H, m), 7.36 (2H, d, J=9 Hz), 7.06 (2H, t, J=8,8 Hz), 6.88–6.94 (1H, m), 3.83–3.95 (4H, m), 2.17–2.26 (2H, m), 1.57–1.83 (3H, m), 0.90 (3H, d, J=6 Hz), 0.87 (3H, d, J=6 Hz).

EXAMPLE 14

4-(1,3-Dihydro-1,3-dioxo-2H-benz[f]isoindol-2-yl)-2-(R)-[[3-methyl-1-(S)-[[(benzyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(benzyl)amino]carbonyl]butyl]amino]-butanoic acid-1,1-dimethylethyl ester Prepared as described for Example 6, Part (a) using benzylamine as HNR²R³ to give the title compound as a tan oil; 60 mg.

(b) 4-(1,3-Dihydro-1,3-dioxo-2H-benz[f]isoindol-2-yl)-2-(R)-[[3-methyl-1-(S)-[[(benzyl)amino]carbonyl]butyl]amino]-butanoic acid Prepared as described for Example 1, Part (b) by hydrolysis of the product of Part (a) above to give the title compound as a colorless solid; 28 mg.

MS; MH+ = 502

¹H-NMR (CDCl₃) δ 8.10 (2H, s broad), 7.90–8.00 (2H, m), 7.60–7.70 (2H, m) 7.20–7.30 (5H, m), 7.10–7.20 (1H, m), 4.40 (2H, d), 4.10–4.20 (1H, m), 3.80–4.00 (2H, m), 3.60–3.70 (1H, m), 3.40–3.50 (1H, m), 2.30–2.40 (2H, m), 1.00–1.40 (3H, m), 0.90–1.00 (6H, m).

EXAMPLE 15

4-(1,3-Dihydro-1,3-dioxo-2H-benz[f]isoindol-2-yl)-2-(R)-[[3-methyl-1-(S)-[[(pyridin-4-ylmethyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(pyridin-4-ylmethyl)amino]carbonyl]butyl]amino]-butanoic acid-1,1-dimethylethyl ester Prepared as described for Example 10, Part (a) using (pyridin-4-ylmethyl)amine as HNR²R³ to afford the title compound as a white solid; 32 mg.

(b) 4-(1,3-Dihydro-1,3-dioxo-2H-benz[f]isoindol-2-yl)-2-(R)-[[3-methyl-1-(S)-[[(pyridin-4-ylmethyl)amino]carbonyl]butyl]amino]-butanoic acid Prepared as described for Example 1, Part (b) by hydrolysis of the product of Part (a) above to give the title compound as a white solid; 17 mg.

MS; MH+ = 503

¹H-NMR (CD₃OD) δ8.58 (2H, d, J=6 Hz), 8.29 (2H, s), 8.04–8.07 (2H, m), 7.70 (2H, d, J=6 Hz), 7.63–7.66 (2H, m) 4.55–4.73 (2H, m), 3.75–3.86 (4H, m), 2.15–2.19 (2H, m), 1.59–1.64 (3H, m), 6.88 (3H, d, J=6 Hz), 0.87 (3H, d, J=6 Hz).

EXAMPLE 16

4-(1,3-Dihydro-1,3-dioxo-2H-benz[f]isoindol-2-yl)-2-(R)-[[3-methyl-1-(S)-[[[2-(1H-imidazol-4-yl)ethyl]amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[[2-(1H-imidazol-4-yl)ethyl]amino]carbonyl]butyl]amino]-butanoic acid-1,1-dimethylethyl ester Prepared as described for Example 10, Part (a) using 2-(1H-imidazole-4-ylethyl)amine as HNR²R³ to give the title compound as a white solid; 74 mg.

(b) 4-(1,3-Dihydro-1,3-dioxo-2H-benz[f]isoindol-2-yl)-2-(R)-[[3-methyl-1-(S)-[[[2-(1H-imidazol-4-yl)ethyl]amino]carbonyl]butyl]amino]-butanoic acid Prepared as described for Example 1, Part (b) by hydrolysis of the product of Part (a) above to give the title compound as a white solid; 43 mg.

MS; MH+ = 506

¹H-NMR (CD₃OD) δ 8.67 (1H, s), 8.29 (2H, s), 8.01–8.05 (2H, m), 7.62–7.66 (2H, m), 7.25 (1H, s), 3.72–3.92 (2H, M), 3.65–3.69 (1H, M), 3.46–3.58 (2H, M), 3.29–3.38 (1H, M), 2.83–2.89 (2H, M), 2.12–2.18 (2H, M), 1.52–1.67 (2H, M), 1.39–1.46 (1H, M), 0.82 (6H, d, J=6 Hz).

EXAMPLE 17

4-(1,3-Dihydro-1,3-dioxo-2H-benz[f]isoindol-2-yl)-2-(R)-[[3-methyl-1-(S)-[[(pyridin-2-ylmethyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(pyridin-2-ylmethyl)amino]carbonyl]butyl]amino]-butanoic acid-1,1-dimethylethyl ester Prepared as described for Example 10, Part (a) using (pyridin-2-ylmethyl)amine as HNR²R³ to afford the title compound as a white solid; 150 mg.

(b) 4-(1,3-Dihydro-1,3-dioxo-2H-benz[f]isoindol-2-yl)-2-(R)-[[3-methyl-1-(S)-[[(pyridin-2-ylmethyl)amino]carbonyl]butyl]amino]-butanoic acid Prepared as described for Example 1, Part (b) by hydrolysis of the product of Part (a) above to give the title compound as a white solid; 71 mg.

MS; MH+ = 503

$^1$H-NMR (CD$_3$OD) δ 8.41–8.44 (1H, m), 8.28 (2H, s), 8.02–8.05 (2H, m), 7.83–7.87 (1H, m), 7.61–7.64 (2H, m), 7.42 (1H, d, J=8 Hz), 7.30–7.35 (1H, m), 4.40 (2H, ABq, Jab=18 Hz), 3.97–3.99 (1H, m), 3.80–3.86 (3H, m), 2.20–2.22 (2H, m), 1.59–1.63 (3H, m), 0.87 (3H, d, J=6 Hz), 0.84 (3H, d, J=6 Hz).

EXAMPLE 18

4-(1,3-Dihydro-1,3-dioxo-2H-benz[f]isoindol-2-yl)-2-(R)-[[3-methyl-1-(S)-[[(4-sulfamoyl-phenyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(4-sulfamoyl-phenyl)amino]carbonyl]butyl]amino]-butanoic acid-1,1-dimethylethyl ester Prepared as described for Example 10, Part (a) using 4-aminobenzenesulfonamide as HNR$^2$R$^3$ to give the title compound as a white solid; 70 mg.

(b) 4-(1,3-Dihydro-1,3-dioxo-2H-benz[f]isoindol-2-yl)-2-(R)-[[3-methyl-1-(S)-[[(4-sulfamoyl-phenyl)amino]carbonyl]butyl]amino]-butanoic acid Prepared as described for Example 1, Part (b) by hydrolysis of the product of Part (a) above to give the title compound as a white solid; 32 mg.

MS; MH+ = 567

$^1$H-NMR (CD$_3$OD) δ 8.23 (2H, s), 8.00–8.04 (2H, m), 7.58–7.70 (6H, m), 3.78–3.91 (4H, m), 2.15–2.25 (2H, m), 1.58–1.79 (3H, m), 0.90 (3H, d, J=7 Hz), 0.86 (3H, d, J=7 Hz).

EXAMPLE 19

4-(1,3-Dihydro-1,3-dioxo-2H-benz[f]isoindol-2-yl)-2-(R)-[[3-methyl-1-(S)-[[(3-sulfamoyl-phenyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(3-sulfamoyl-phenyl)amino]carbonyl]butyl]amino]-butanoic acid-1,1-dimethylethyl ester Prepared as described for Example 10, Part (a) using 3-aminobenzenesulfonamide as HNR$^2$R$^3$ to give the title compound as a white solid; 116 mg.

(b) 4-(1,3-Dihydro-1,3-dioxo-2H-benz[f]isoindol-2-yl)-2-(R)-[[3-methyl-1-(S)-[[(3-sulfamoyl-phenyl)amino]carbonyl]butyl]amino]-butanoic acid Prepared as described for Example 1, Part (b) by hydrolysis of the product of Part (a) above to give the title compound as a white solid; 51 mg.

MS; MH+ = 567

$^1$H-NMR (CD$_3$OD) δ 8.21 (2H, s), 8.11 (1H, s), 7.99–8.02 (2H, m), 7.60–7.63 (2H, m), 7.49–7.53 (1H, m), 7.41–7.45 (1H, m), 7.16 (1H, t, J=8 Hz), 3.80–3.91 (4H, m), 2.17–2.22 (2H, m), 1.59–1.77 (3H, m), 0.89 (3H, d, J=6 Hz), 0.86 (3H, d, J=6 Hz).

EXAMPLE 20

4-(1,3-Dihydro-1,3-dioxo-2H-benz[f]isoindol-2-yl)-2-(R)-[[3-methyl-1-(S)-[[(4-dimethylamino-benzyl)amino]carbonyl]butyl]amino]butanoic acid (a) 4-(1,3-Dihydro-1,3-dioxo-2H-benz[f]isoindol-2-yl)-2-(R)-[[3-methyl-1-(S)-[[(4-dimethylaminobenzyl)amino]carbonyl]butyl]amino]-butanoic acid-1,1-dimethylethyl ester Prepared as described for Example 10, Part (a) using (4-aminomethylphenyl)-dimethyl-amine as HNR$^2$R$^3$ to afford the title compound as a light yellow solid; 137 mg.

(b) 4-(1,3-Dihydro-1,3-dioxo-2H-benz[f]isoindol-2-yl)-2-(R)-[[3-methyl-1-(S)-[[(4-dimethylaminobenzyl)amino]carbonyl]butyl]amino]-butanoic acid Prepared as described for Example 1, Part (b) by hydrolysis of the product of Part (A) above to give the title compound as a light yellow solid; 57 mg.

MS; [M+2Na]+ = 589

$^1$H-NMR (CD$_3$OD) δ 8.29 (2H, s), 8.03–8.06(2H, m), 7.62–7.65 (2H, m), 7.17 (2H, d, J=9 Hz), 6.94 (2H, d, J=9 Hz), 4.23 (2H, m), 3.71–3.86 (4H, m), 2.90 (6H, s), 2.11–2.18 (2H, m), 1.52–1.72 (3H, m), 0.84 (3H, d, J=6 Hz), 0.82 (3H, m).

EXAMPLE 21

4-(1,3-Dihydro-1,3-dioxo-2H-benz[f]isoindol-2-yl)-2-(R)-[[3-methyl-1-(S)-[[[1-(S)-phenyl-ethyl]amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[[1-(S)-phenyl-ethyl]amino]carbonyl]butyl]amino]-butanoic acid-1,1-dimethylethyl ester Prepared as described for Example 10, Part (a) using 1-(S)-phenylethylamine as HNR$^2$R$^3$ to give the title compound as a white solid; 42 mg.

(b) 4-(1,3-Dihydro-1,3-dioxo-2H-benz[f]isoindol-2-yl)-2-(R)-[[3-methyl-1-(S)-[[[1-(S)-phenyl-ethyl]amino]carbonyl]butyl]amino]-butanoic acid Prepared as described for Example 1, Part (b) by hydrolysis of the product of Part (a) above to give the title compound as a white solid; 20 mg.

MS; MH+ = 516

$^1$H-NMR (CD$_3$OD) δ 8.28 (2H, s), 8.02–8.07 (2H, m), 7.60–7.66 (2H, m), 7.12–7.26 (4H, m), 6.97–7.03 (1H, m), 4.90 (2H, ABq, Jab=6 Hz), 3.69–3.79 (3H, m), 3.56–3.65 (1H, m), 1.96–2.11 (2H, m), 1.55–1.75 (3H, m), 1.33 (3H, d, J=9 Hz), 0.90–0.91 (3H, d, J=6 Hz),)0.88 (3H, d, J=6 Hz).

EXAMPLE 22

4-(1,3-Dihydro-1,3-dioxo-2H-benz[f]isoindol-2-yl)-2-(R)-[[3-methyl-1-(S)-[[(1,1-dioxo-tetrahydro-thiophen-3-yl)amino]carbonyl]butyl]amino]butanoic acid (a) 4-(1,3-Dihydro-1,3-dioxo-2H-benz[f]isoindol-2-yl)-2-(R)-[[3-methyl-1-(S)-[[(1,1-dioxo-tetrahydro-thiophen-3-yl)amino]carbonyl]butyl]amino]-butanoic acid-1,1-dimethylethyl ester Prepared as described for Example 10, Part (a) using 1,1-dioxotetrahydro-thiophen-3-ylamine as HNR$^2$R$^3$ to afford the title compound as a white solid; 18 mg.

(b) 4-(1,3-Dihydro-1,3-dioxo-2H-benz[f]isoindol-2-(R)-[[3-methyl-1-(S)-[[(1,1-dioxo-tetrahydro-thiophen-3-yl)amino]carbonyl]butyl]amino]-butanoic acid Prepared as described for Example 1, Part (b) by hydrolysis of the product of Part (a) above to give the title compound as a white solid; 8 mg.

MS; MH+ = 530

$^1$H-NMR (CD$_3$OD) δ 8.31 (2H, m), 8.03–8.08 (2H, m), 7.61–7.66 (2H, m), 4.43–4.54 (1H, m), 3.72–3.90 (3H, m), 3.56–3.65 (1H, m), 3.20–3.43 (1H, m), 2.80–3.10 (3H, m), 2.05–2.15 (2H, m), 1.45–1.75 (3H, m), 0.75–0.95 (6H, m).

EXAMPLE 23

4-(1,3-Dihydro-1,3-dioxo-2H-benz[f]isoindol-2-yl)-2-(R)-[[3-methyl-1-(S)-[[(4-sulfamoyl-benzyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(4-sulfamoyl-benzyl)amino]carbonyl]butyl]amino]-butanoic acid-1,1-dimethylethyl ester 100 mg of N-[(R)-1-[(1,1-dimethylethoxy)carbonyl]-3-(1,3-dihydro-1,3-dioxo-2H-benz[f]isoindol-2-yl)propyl]-L-leucine, prepared as in Example L, was added to 0.8 mL DMF. 39 mg of hydroxybenzotriazol.-H$_2$O was added to the mixture followed by 57 mg of 4-aminoethylbenzenesulfonamide, 0.03 mL of N-methyl-4-morpholine, and 53 mg of dicyclohexylcarbodiimide. The mixture was stirred 72 h, and diluted with dichloromethane. The solvents were removed by evaporation and the resulting solid was purified by reverse phase H.P.L.C. The solvents were removed by lyopholization to give the title compound as a white solid; 104 mg.

(b) 4-(1,3-Dihydro-1,3-dioxo-2H-benz[f]isoindol-2-yl)-2-(R)-[[3-methyl-1-(S)-[[(4-sulfamoyl-benzyl)amino]carbonyl]butyl]amino]-butanoic acid Prepared as described for Example 1, Part (b) by hydrolysis of the product of Part (a) above to give the title compound as a white solid; 30 mg.

MS; MH+ = 581

$^1$H-NMR (CD$_3$OD) δ 8.32 (2H, s), 8.05–8.06 (2H, m), 7.76 (2H, d, J=6 Hz), 7.64–7.67 (2H, m), 7.37 (2H, d, J=6 Hz), 4.38 (2H, m), 3.73–3.86 (4H, m), 2.17–2.20 (2H, m), 1.57–1.58 (3H, m), 0.88 (3H, d, J=6 Hz), 0.85 (3H, d, J=6 Hz).

EXAMPLE 24

4-(1,3-Dihydro-1,3-dioxo-2H-benz[f]isoindol-2-yl)-2-(R)-[[3-methyl-1-(S)-[[[1-(R)-phenyl-ethyl]amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[[1-(R)-phenyl-ethyl]amino]carbonyl]butyl]amino]-butanoic acid-1,1-dimethylethyl ester Prepared as described for Example 10, Part (a) using 1-(R)-phenyl-ethylamine as HNR$^2$R$^3$ to give the title compound as a white solid; 42 mg.

(b) 4-(1,3-Dihydro-1,3-dioxo-2H-benz[f]isoindol-2-yl)-2-(R)-[[3-methyl-1-(S)-[[[1-(R)-phenyl-ethyl]amino]carbonyl]butyl]amino]-butanoic acid Prepared as described for Example 1, Part (b) by hydrolysis of the product of Part (a) above to give the title compound as a white solid.

MS; MH+ = 516

$^1$H-NMR (CD$_3$OD) δ 8.33 (2H, s), 8.07–8.10 (2H, m), 7.65–7.69 (2H, m), 7.10–7.25 (5H, m), 4.97–4.99 (2H, m), 3.72–3.95 (4H, m), 2.16–2.27 (2H, m), 1.46–1.71 (3H, m), 1.42 (3H, d, J=6 Hz), 0.83 (3H, d, J=6 Hz), 0.75 (3H, d, J=6 hz).

EXAMPLE 25

4-(1,3-Dihydro-1,3-dioxo-2H-benz[f]isoindol-2-yl)-2-(R)-[[3-methyl-1-(S)-[[(3-fluorobenzyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(3-fluorobenzyl)amino]carbonyl]butyl]amino]-butanoic acid-1,1-dimethylethyl ester Prepared as described for Example 10, Part (a) using (3-fluorobenzyl)amine HNR$^2$R$^3$ to afford the title compound as a white solid; 60 mg.

(b) 4-(1,3-Dihydro-1,3-dioxo-2H-benz[f]isoindol-2-yl)-2-(R)-[[3-methyl-1-(S)-[[(3-fluorobenzyl)amino]carbonyl]butyl]amino]-butanoic acid Prepared as described for Example 1, Part (b) by hydrolysis of the product of Part (a) above to give the title compound as a white solid; 33 mg.

MS; MH+ = 520

$^1$H-NMR (CD$_3$OD) δ 8.31 (2H, s), 8.05–8.11 (2H, m), 7.63–7.70 (2H, m), 7.18–7.26 (1H, m), 6.95–7.03 (2H, m), 6.83–6.92 (1H, m), 4.23 (2H, ABq, Jab=15 Hz), 3.69–3.92 (4H, m), 2.09–2.27 (2H, m), 1.48–178 (3H, m), 0.78–0.96 (6H, m).

EXAMPLE 26

4-(1,3-Dihydro-1,3-dioxo-2H-benz[f]isoindol-2-yl)-2-(R)-[[3-methyl-1-(S)-[[(furan-2-ylmethyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(furan-2-ylmethyl)amino]carbonyl]butyl]amino]-butanoic acid-1,1-dimethylethyl ester Prepared as described for Example 10, Part (a) using (furan-2-ylmethyl)amine as HNR$^2$R$^3$ to afford the title compound as a white solid; 101 mg.

(b) 4-(1,3-Dihydro-1,3-dioxo-2H-benz[f]isoindol-2-yl)-2-(R)-[[3-methyl-1-(S)-[[(furan-2-ylmethyl)amino]carbonyl]butyl]amino]-butanoic acid Prepared as described for Example 1, Part (b) by hydrolysis of the product of Part (a) above to give the title compound as a white solid; 33 mg.

MS; MH+ = 492

$^1$H-NMR (CD$_3$OD) δ 8.29 (2H, s), 8.03–8.07 (2H, m), 7.62–7.67 (2H, m), 7.30 (1H, m), 6.20 (1H, m), 6.17 (1H, m), 4.21 (2H, ABq, Jab=15,27 Hz), 3.72–3.91 (2H, m), 3.53–3.66 (2H, m), 2.03–2.18 (2H, m), 1.52–1.68 (3H, m), 0.78–0.93 (6H, m).

EXAMPLE 27

4-(1,3-Dihydro-1,3-dioxo-2H-benz[f]isoindol-2-yl)-2-(R)-[[3-methyl-1-(S)-[[(1-methyl-1H-tetrazol-5-ylmethyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(1-methyl-1H-tetrazol-5-ylmethyl)amino]carbonyl]butyl]amino]-butanoic acid-1,1-dimethylethyl ester Prepared as described for Example 1, Part (a) using (1-methyl-1H-tetrazol-5-ylmethyl)amine as HNR$^2$R$^3$ to afford the title compound as a solid; 235 mg.

(b) 4-(1,3-Dihydro-1,3-dioxo-2H-benz[f]isoindol-2-yl)-2-(R)-[[3-methyl-1-(S)-[[(1-methyl-1H-tetrazol-5-ylmethyl)amino]carbonyl]butyl]amino]-butanoic acid Prepared as described for Example 1, Part (b) by hydrolysis of the product of Part (a) above to give the title compound as a solid; 105 mg. MS; MH+ = 508

$^1$H-NMR (CD$_3$OD) δ 8.40 (2H, s), 8.16 (2H, m), 7.75 (2H, m), 4.70, (2H, m), 4.10 (3H, s), 3.8–4.0 (4H, m)., 2.26 (2H, broad q), 1.6–1.85 (3H, m), 0.95 (6H, m).

EXAMPLE 28

4-(1,3-Dihydro-1,3-dioxo-2H-benz[f]isoindol-2-yl)-2-(R)-[[3-methyl-1-(S)-[[(1,2,3,4-tetrahydro-naphthalen-1-yl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(1,2,3,4-tetrahydro-naphthalen-1-yl)amino]carbonyl]butyl]amino]-butanoic acid-1,1-dimethylethyl ester Prepared as described in Example 1, Part (a) using 1,2,3,4-tetrahydronaphthalen-1-ylamine as $HNR^2R^3$ to give the title compound as an oil; 300 mg.

(b) 4-(1,3-Dihydro-1,3-dioxo-2H-benz[f]isoindol-2-yl)-2-(R)-[[3-methyl-1-(S)-[[(1,2,3,4-tetrahydro-naphthalen-1-yl)amino]carbonyl]butyl]amino]-butanoic acid Prepared as described for Example 1, Part (b) by hydrolysis of the product of Part (a) above to give the title compound.

MS; $MH^+ = 542$ $^1$H-NMR (CD$_3$OD) δ 8.43 (2H, s), 8.19 (2H, m), 7.79 (2H, m), 7.07–7.37 (4H, m), 5.07–5.2 (1H, m), 3.82–4.12 (4H, m), 2.80 (2H, m), 2.33 (2H, m), 1.67–2.10 (7H, m), 1.05 (6H, m).

EXAMPLE 29

4-(1,3-Dihydro-1,3-dioxo-2H-benz[f]isoindol-2-yl)-2-(R)-[[3-methyl-1-(S)-[[(2,4-difluoro-benzyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(2,4-difluorobenzyl)amino]carbonyl]butyl]amino]-butanoic acid-1,1-dimethylethyl ester Prepared as described for Example 10, Part (a) using 2,4-difluorobenzylamine as $HNR^2R^3$ to afford the title compound as a white solid; 258 mg.

(b) 4-(1,3-Dihydro-1,3-dioxo-2H-benz[f]isoindol-2-yl)-2-(R)-[[3-methyl-1-(S)-[[(2,4-difluorobenzyl)amino]carbonyl]butyl]amino]-butanoic acid Prepared as described for Example 1, Part (b) by hydrolysis of the product of Part (a) above to give the title compound as a white solid; 170 mg.

MS; $MH^+ = 538$ $^1$H-NMR (CD$_3$OD) δ 8.32 (2H, s), 8.06–8.09 (2H, m), 7.64–7.69 (2H, m) 7.28–7.36 (1H, m), 6.79–7.36 (2H, m), 4.25 (2H, ABq, Jab=15,21 Hz), 3.78–3.92 (3H, m), 3.69–3.74 (1H, m), 2.09–2.23 (2H, m), 1.47–1.75 (3H, m), 0.85 (3H, d, J=6 Hz), 0.83 (3H, d, J=6 Hz).

EXAMPLE 30

4-(1,3-Dihydro-1,3-dioxo-2H-benz[f]isoindol-2-yl)-2-(R)-[[3-methyl-1-(S)-[[(3-nitrobenzyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(3-nitrobenzyl)amino]carbonyl]butyl]amino]-butanoic acid-1,1-dimethylethyl ester Prepared as described for Example 1, Part (a) using 3-nitrobenzylamine as $HNR^2R^3$ to give the title compound as a light yellow oil; 140 mg.

(b) 4-(1,3-Dihydro-1,3-dioxo-2H-benz[f]isoindol-2-yl)-2-(R)-[[3-methyl-1-(S)-[[(3-nitrobenzyl)amino]carbonyl]butyl]amino]-butanoic acid Prepared as described for Example 1, Part (b) by hydrolysis of the product of Part (a) above to give the title compound as a white solid; 97 mg.

MS; $MH^+ = 547$ $^1$H-NMR (CD$_3$OD) δ 8.30 (2H, s), 7.98–8.08 (4H, m), 7.60–7.67 3H, m), 7.46 (1H, t, J=6 Hz), 4.35 (2H, ABq, Jab=15, 18 Hz), 3.73–3.88 (4H, m), 2.12–2.20 (2H, m), 1.54–177 (3H, m), 0.88 (3H, d, J=6 Hz), 0.85 (3H, d, J=6 Hz).

EXAMPLE 31

4-(1,3-Dihydro-1,3-dioxo-2H-benz[f]isoindol-2-yl)-2-(R)-[[3-methyl-1-(S)-[[(4-nitrobenzyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(4-nitrobenzyl)amino]carbonyl]butyl]amino]-butanoic acid-1,1-dimethylethyl ester Prepared as described for Example 1, Part (a) using 4-Nitrobenzylamine as $HNR^2R^3$ to give the title compound as a light yellow oil; 141 mg.

(b) 4-(1,3-Dihydro-1,3-dioxo-2H-benz[f]isoindol-2-yl)-2-(R)-[[3-methyl-1-(S)-[[(4-nitrobenzyl)amino]carbonyl]butyl]amino]-butanoic acid Prepared as described for Example 1, Part (b) by hydrolysis of the product of Part (a) above to give the title compound as a white solid; 98 mg.

MS; $MH^+ = 547$ $^1$H-NMR (CD$_3$OD) δ 8.32 (2H, s), 8.06–8.11 (4H, m), 7.64–7.69 (2H, m), 7.41–7.47 (2H, m), 4.44 (2H, m), 3.72–3.90 (4H, m), 2.13–2.34 (2H, m), 1.52–1.78 (3H, m), 0.87–0.91 (6H, m).

EXAMPLE 32

4-(1,3-Dihydro-1,3-dioxo-2H-benz[f]isoindol-2-yl)-2-(R)-[[3-methyl-1-(S)-[[(4-methanesulfonylamino-benzyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(4-methanesulfonylaminobenzyl)amino]carbonyl]butyl]amino]-butanoic acid-1,1-dimethylethyl ester Prepared as described for Example 1, Part (a) using N-(4-aminomethylphenyl)-methanesulfonamide as $HNR^2R^3$ to afford the title compound as an oil; 400 mg.

(b) 4-(1,3-Dihydro-1,3-dioxo-2H-benz[f]isoindol-2-yl)-2-(R)-[[3-methyl-1-(S)-[[(4-methanesulfonylaminobenzyl)amino]carbonyl]butyl]amino]-butanoic acid Prepared as described for Example 1, Part (b) by hydrolysis of the product of Part (a) above to give the title compound as a white solid; 45 mg.

MS; $MH^+ = 595$ $^1$H-NMR (CD$_3$OD) δ 8.39 (2H, s), 8.14 (2H, m), 7.74 (2H, m), 7.29 (2H, d), 7.20 (2H, d), 4.33 and 4.40 (2H, ABq, J=15 Hz), 3.80–4.20 (4H, m), 2.91 (3H, s), 2.27 (2H, m), 1.55–1.92 (3H, m), 0.96 (6H, m).

EXAMPLE 33

4-(1,3-Dihydro-1,3-dioxo-2H-benz[f]isoindol-2-yl)-2-(R)-[[3-methyl-1-(S)-[[(3-methanesulfonylamino-benzyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(3-methanesulfonylaminobenzyl)amino]carbonyl]butyl]amino]-butanoic acid-1,1-dimethylethyl ester Prepared as described for Example 1, Part (a) using N-(3-aminomethylphenyl)-methanesulfonamide as $HNR^2R^3$ to afford the title compound as an oil; 350 mg.

(b) 4-(1,3-Dihydro-1,3-dioxo-2H-benz[f]isoindol-2-yl)-2-(R)-[[3-methyl-1-(S)-[[(3-methanesulfonylaminobenzyl)amino]carbonyl]butyl]amino]-butanoic acid Prepared as described for Example 1, Part (b) by hydrolysis of the product of Part (a) above to give the title compound as a white solid; 268 mg.

MS; MH+ =594 $^1$H-NMR (CD$_3$OD) δ 8.43 (2H, s), 8.16 (2H, m), 7.76 (2H, m), 7.26 (2H, m), 7.07 (2H, m), 4.46 and 4.33 (2H, ABq, J=15 Hz), 3.48–4.23 (4H, m), 2.30 (2H, m), 1.60–1.96 (3H, m), 0.97 (6H, m).

EXAMPLE 34

4-(1,3-Dihydro-1,3-dioxo-2H-benz[f]isoindol-2-yl)-2-(R)-[[3-methyl-1-(S)-[[(3,4-difluoro-benzyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(3,4-difluorobenzyl)amino]carbonyl]butyl]amino]-butanoic acid-1,1-dimethylethyl ester Prepared as described for Example 1, Part (a) using 3,4-difluorobenzylamine as HNR$^2$R$^3$ to give the title compound as a white solid; 302 mg.

(b) 4-(1,3-Dihydro-1,3-dioxo-2H-benz[f]isoindol-2-yl)-2-(R)-[[3-methyl-1-(S)-[[(3,4-difluorobenzyl)amino]carbonyl]butyl]amino]-butanoic acid Prepared as described for Example 1, Part (b) by hydrolysis of the product of Part (a) above to give the title compound as a white solid; 47 mg.

MS; MH+ =538
$^1$H-NMR (CD$_3$OD) δ

EXAMPLE 35

4-(1,3-Dihydro-1,3-dioxo-2H-benz[f]isoindol-2-yl)-2-(R)-[[3-methyl-1-(S)-[[(3-trifluoromethyl-benzyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(3-trifluoromethylbenzyl)amino]carbonyl]butyl]amino]-butanoic acid-1,1-dimethylethyl ester Prepared as described for Example 1, Part (a) using 3-trifluoromethylbenzylamine as HNR$^2$R$^3$ to afford the title compound as a white solid; 250 mg.

(b) 4-(1,3-Dihydro-1,3-dioxo-2H-benz[f]isoindol-2-yl)-2-(R)-[[3-methyl-1-(S)-[[(3-trifluoromethylbenzyl)amino]carbonyl]butyl]amino]-butanoic acid Prepared as described for Example 1, Part (b) by hydrolysis of the product of Part (a) above to give the title compound as a white solid; 177 mg.

MS; MH+ =570
$^1$H-NMR (CD$_3$OD) δ 8.39 (2H, s), 8.16 (2H, m), 7.75 (2H, m), 7.46–7.63 (4H, m), 4.57 and 4.38 (2H, ABq, J=15 Hz), 3.79–4.01 (2H, m), 3.61–3.77 (2H, m), 2.20 (2H, m), 1.57–1.83 (3H, m), 0.93 (6H, m).

EXAMPLE 36

4-[2-(S)-[1-(R)-Carboxy-3-(1,3-dioxo1,3-dihydro-benzo[f]isoindol-2-yl)propylamino]-4-methyl-pentanoylamino-methyl)-benzoic acid (a) 4-[2-(S)-[1-(R)-(1,1-dimethylethyl)Carbonyl-3-(1,3-dioxo1,3-dihydro-benzo[f]isoindol-2-yl)-propylamino]-4-methyl-pentanoylamino-methyl)-benzoic acid 100 mg of N-[(R)-1-[(1,1-dimethylethoxy)carbonyl]-3-(1,3-dihydro-1,3-dioxo-2H-benz[f]isoindol-2-yl)propyl]-L-leucine, prepared as in Example L, was added to a mixture of 0.174 mL of diisopropylethylamine, 1 mL DMF, and 1.1 mL of 0.45M hydroxybenzotriazol-benzotriazoltetramethyluronium hexafluorophosphate in DMF at 5° C. 75 mg of 4-(Aminomethyl)-benzoic acid was added and the mixture was stirred for 24 h. The solvents were removed by evaporation to give the title compound; 84 mg.

(b) 4-[2-(S)-[1-(R)-Carboxy-3-(1,3-dihydro-benzo[f]isoindol-2-yl)-propylamino[-4-methyl-pentanoylamino-methyl]-benzoic acid Prepared as described for Example 1, Part (b) by hydrolysis of the product of Part (a) above to give the title compound as a solid; 20 mg.

MS; MH+ =546
$^1$H-NMR (CD$_3$OD) δ 8.38 (2H, s), 8.14 (2H, m), 7.96 (2H, d, J=8 Hz), 7.74 (2H, m), 7.40 (2H, d, J=8 Hz), 4.51 and 4.44 (2, H, ABq, J=15 Hz), s), 8.16 (2H, m), 7.75 (2H, m), 4.70, (2H, m), 4.10

EXAMPLE 37

4-(1,3-Dihydro-1,3-dioxo-2H-benz[f]isoindol-2-yl)-2-(R)-[[3-methyl-1-(S)-[[(2-hydroxy-1.1-bis-hydroxymethyl-ethyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(2-hydroxy-1,1-bis-hydroxymethylethyl)amino]carbonyl]butyl]amino]-butanoic acid-1,1-dimethylethyl ester Prepared as described for Example 1, Part (a) using 2-amino-2-hydroxymethyl-propane-1,2-diol as HNR$^2$R$^3$ to afford the title compound as an oily sludge; 94 mg.

(b) 4-(1,3-Dihydro-1,3-dioxo-2H-benz[f]isoindol-2-yl)-2-(R)-[[3-methyl-1-(S)-[[(2-hydroxy-1,1-bis-hydroxymethylethyl)amino]carbonyl]butyl]amino]-butanoic acid Prepared as described for Example 1, Part (b) by hydrolysis of the product of Part (a) above to give the title compound as a white solid; 21 mg.

MS; MH+ =516
$^1$H-NMR (CD$_3$OD) δ 8.34 (2H, s), 8.06–8.11 (2H, m), 7.64–7.70 (2H, m), 3.8103.96 (4H, m), 3.68 (6H, d, J=6 Hz), 2.22–2.29 (2H, m), 1.57–1.79 (3H, m), 0.93 (3H, d, J=6 Hz), 0.91 (3H, d, J=6 Hz).

EXAMPLE 38

4-(1,3-Dihydro-1,3-dioxo-2H-benz[f]isoindol-2-yl)-2-(R)-[[3-methyl-1-(S)-[[(3,5-difluoro-benzyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(3,5-difluorobenzyl)amino]carbonyl]butyl]amino]-butanoic acid-1,1-dimethylethyl ester Prepared as described for Example 1, Part (a) using 3,5-difluorobenzylamine as HNR$^2$R$^3$ to give the title compound as a white solid; 300 mg.

(b) 4-(1,3-Dihydro-1,3-dioxo-2H-benz[f]isoindol-2-yl)-2-(R)-[[3-methyl-1-(S)-[[(3,5-difluorobenzyl)amino]carbonyl]butyl]amino]-butanoic acid Prepared as described for Example 1, Part (b) by hydrolysis of the product of Part (a) above to give the title compound as a white solid; 220 mg. MS; MH+ =538

$^1$H-NMR (CD$_3$OD) δ 8.31 (2H, s), 8.05–8.08 (2H, m), 7.64–7.67 (2H, m), 6.71–6.85 (3H, m), 4.24 (2H, ABq, Jab=12, 15 Hz), 3.80–3.88 (3H, m), 3.72–3.76 (1H, m), 2.17–2.20 (2H, m), 1.57–1.73 (3H, m), 0.88 (2H, d, J=6 Hz), 0.86 (2H, d, J=6 Hz).

EXAMPLE 39

4-(1,3-Dihydro-1,3-dioxo-2H-benz[f]isoindol-2-yl)-2-(R)-[[3-methyl-1-(S)-[[benzyl-methyl-amino]carbonyl]-butyl]amino]-butanoic acid (a) 4-(1,3-Dihydro-1,3-dioxo-2H-benz[f]isoindol-2-yl)-2-(R)-[[3-methyl-1-(S)-[[benzyl-methyl-amino]carbonyl]butyl]amino]-butanoic acid-1,1-dimethylethyl ester Prepared as described in Example 1, Part (a) using benzyl-methyl-amine as HNR$^2$R$^3$ to afford the title compound as a solid; 280 mg.

(b) 4-(1,3-Dihydro-1,3-dioxo-2H-benz[f]isoindol-2-yl)-2-(R)-[[3-methyl-1-(S)-[[benzyl-methyl-amino]carbonyl]butyl]amino]-butanoic acid Prepared as described for Example 1, Part (b) by hydrolysis of the product of Part (a) above to give the title compound as a white solid; 104 mg. MS; MH$^+$ = 516

$^1$H-NMR (CD$_3$OD) δ 8.33 minor and 8.35 major (2H, s), 8.12 (2H, m), 7.72 (2H, m), 7.15–7.38 (5H, m), 4.76–4.38 (3H, m), 3.77–4.05 (3H, m), 3.01 minor and 3.04 major (3H, s), 2.17 minor and 2.30 major (2H, m), 1.67–1.94 (3H, m), 0.86–0.97 minor and 1.00 major (6H, m).

EXAMPLE 40

4-(1,3-Dihydro-1,3-dioxo-2H-benz[f]isoindol-2-yl)-2-(R)-[[3-methyl-1-(S)-[[2-dimethylaminoethyl)-methyl-amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(2-dimethylaminoethyl)-methylamino]carbonyl]butyl]amino]-butanoic acid-1,1-dimethylethyl ester Prepared as described in Example 1, Part (a) using N,N,N'-trimethylethane-1,2-diamine as HNR$^2$R$^3$ to give the title compound as a solid; 260 mg.

(b) 4-(1,3-Dihydro-1,3-dioxo-2H-benz[f]isoindol-2-yl)-2-(R)-[[3-methyl-1-(S)-[[(2-dimethylaminoethyl)-methylamino]carbonyl]butyl]amino]-butanoic acid Prepared as described for Example 1, Part (b) by hydrolysis of the product of Part (a) above to give the title compound as a solid; 176 mg.

MS; MH$^+$ = 497

$^1$H-NMR (CD$_3$OD) δ 8.31 (2H, s), 8.10 (2H, m), 7.70 (2H, m), 4.47 (1H, m), 3.83–4.17 (4H, m), 3.29–3.66 (3H, m), 3.17 (3H, s), 2.97 (6H, s), 2.14 (2H, m), 1.67–1.97 (3H, m), 1.00 (6H, m).

EXAMPLE 41 and EXAMPLE 42

4-(1,3-Dihydro-1,3-dioxo-2H-benz[f]isoindol-2-yl)-2-(R)-[[3-methyl-1-(S)-[[(1-aza-bicyclo[2.2.2]oct-3-(R)-yl)amino]carbonyl]butyl]amino]-butanoic acid and 4-(1,3-Dihydro-1,3-dioxo-2H-benz[f]isoindol-2-yl)-2-(R)-[[3-methyl-1-(S)-[[(1-aza-bicyclo[2.2.2]oct-3-(S)-yl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(1-aza-bicyclo[2.2.2]oct-3-yl)amino]carbonyl]butyl]amino]-butanoic acid-1,1-dimethylethyl ester Prepared as described in Example 1, Part (a) using (1-aza-bicyclo[2.2.2]oct-3-yl)amine as HNR$^2$R$^3$ to afford the title compound as a solid; 270 mg.

(b) 4-(1,3-Dihydro-1,3-dioxo-2H-benz[f]isoindol-2-yl)-2-(R)-[[3-methyl-1-(S)-[[(1-aza-bicyclo[2.2.2]oct-3-yl)amino]carbonyl]butyl]amino]-butanoic acid Prepared as described for Example 1, Part (b) by hydrolysis of the product of Part (a) above to give the title compound as a solid; 154 mg. The R and S stereoisomers were separated by RP-HPLC on a C-18 column using a 15–80% CH$_3$CN in H$_2$O with .1% T.F.A. gradient over 30 minutes to give two peaks eluting at 10.11 and 10.86 minutes.

MS; MH$^+$ = 521

[10.86 minute peak] $^1$H-NMR (CD$_3$OD) δ 8.38 (2H, s), 8.14 (2H, m), 7.74 (2H, m), 4.30 (1H, m), 3.86–4.03 (4H, m), 3.76 (1H, ddd, J=13,10,2 Hz), 3.22–3.44 (4H, m), 3.11 (1H, ddd, J=14, 5.5, 2 Hz), 1.60–2.40 (10H, m), 0.98 (6H, m).

[10.11 minute peak] $^1$H-NMR (CD$_3$OD) δ8.39 (2H, s), 8.15 (2H, m), 7.75 (2H, m), 4.32 (1H, m), 3.75–4.05 and 3.20–3.50 (10H,m), 1.60–2.38 (10H, m), 0.98 (6H, m).

EXAMPLE 43

4-(1,3-Dihydro-1,3-dioxo-2H-benz[f]isoindol-2-yl)-2-(R)-[[3-methyl-1-(S)-[[(3-(R)-4-(S)-5-(R)-6-tetrahydroxy-tetrahydro-pyran-2-(R)-ylmethyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(3-(R)-4-(S)-5-(R)-6-tetrahydroxytetrahydro-pyran-2-(R)-ylmethyl)amino]carbonyl]butyl]amino]-butanoic acid-1,1-dimethylethyl ester Prepared as described in Example 1, Part (a) using 6-amino-6-deoxy-D-glucose as HNR$^2$R$^3$ to give the title compound.

(b) 4-(1,3-Dihydro-1,3-dioxo-2H-benz[f]isoindol-2-yl)-2-(R)-[[3-methyl-1-(S)-[[(3-(R)-4-(S)-5-(R)-6-tetrahydroxytetrahydro-pyran-2-(R)-ylmethyl)amino]carbonyl]butyl]amino]-butanoic acid Prepared as described for Example 1, Part (b) by hydrolysis of the product of Part (a) above to give the title compound as a solid; 65 mg.

MS; MH$^+$ = 574

$^1$H-NMR (CD$_3$OD) δ 8.30 (2H, s), 8.05 (2H, m), 7.69 (2H, m), 5.10 (0.5H, d, J =4 Hz), 4.50 (0.5H, d, J=8 Hz), 3.83 (5H, m), 3.10–4.05 (6H, m), 2.35 (2H, m), 1.65–1.95 (3H, m), 0.96 (6H, m).

EXAMPLE 44

4-(1,3-Dihydro-1,3-dioxo-2H-benz[f]isoindol-2-yl)-2-(R)-[[3-methyl-1-(S)-[(N,N'-dimethyl-hydrazino)carbonyl]butyl]amino]-butanoic acid (a) 4-(1,3-Dihydro-1,3-dioxo-2H-benz[f]isoindol-2-yl)-2-(R)-[[3-methyl-1-(S)-[N,N'-dimethyl-hydrazino)-carbonyl]butyl]amino]-butanoic acid-1,1-dimethylethyl ester Prepared as described in Example 1, Part (a) using N,N'-dimethylhydrazine as HNR$^2$R$^3$ to afford the title compound as a yellow solid; 229 mg.

(b) 4-(1,3-Dihydro-1,3-dioxo-2H-benz[f]isoindol-2-yl)-2-(R)-[[3-methyl-(S)-1-[(N,N'-dimethyl-hydrazino)-carbonyl]butyl]amino]-butanoic acid Prepared as described for Example 1, Part (b) by hydrolysis of the product of Part (a) above to give the title compound as a white solid; 43 mg.

MS; MH$^+$ = 455

$^1$H NMR (CD$_3$OD) δ 8.31 (2H, s), 8.05–8.08 (2H, m), 7.64–7.68 (2H, m), 3.69–3.93 (4H, m), 3.03 (3H, s), 2.51 (3H, s), 2.13–2.24 (2H, m), 1.66–1.67 (3H, m), 0.90–0.92 (6H, m).

EXAMPLE 45

4-(1,3-Dihydro-1,3-dioxo-2H-benz[f]isoindol-2-yl)-2-(R)-[[3-methyl-1-(S)-[[(methyl-methoxy)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(methyl-methoxy)amino]carbonyl]butyl]amino]-butanoic acid-1,1-dimethylethyl ester Prepared as described in Example 1, Part (a) using N,O-dimethylhydroxylamine as $HNR^2R^3$ to give the title compound as a whtie solid; 236 mg.

(b) 4-(1,3-Dihydro-1,3-dioxo-2H-benz[f]isoindol-2-yl)-2-(R)-[[3-methyl-1-(S)-[[(methyl-methoxy)amino]carbonyl]butyl]amino]-butanoic acid Prepared as described for Example 1, Part (b) by hydrolysis of the product of Part (a) above to give the title compound as a white solid; 128 mg.

MS; $MH^+ = 456$ $^1$H-NMR (CD$_3$OD) δ 8.31 (2H, s), 8.05–8.09 (2H, m), 7.62–7.68 (2H, m), 4.30–4.34 (1H, m), 3.81–3.93 (3H, s), 3.13 (3H, s), 2.16–2.25 (2H, m), 1.61–1.70 (3H, m), 0.88 (6H, d, J=6 Hz).

EXAMPLE 46

4-(1,3-Dihydro-1,3-dioxo-2H-benz[f]isoindol-2-yl)-2-(R)-[[3-methyl-1-(S)-[[(dimethyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(dimethyl)amino]carbonyl]butyl]amino]-butanoic acid-1,1-dimethylethyl ester Prepared as described in Example 1, Part (a) using dimethylamine-HCl as $HNR^2R^3$ to give the title compound as a white solid; 61 mg.

(b) 4-(1,3-Dihydro-1,3-dioxo-2H-benz[f]isoindol-2-yl)-2-(R)-[[3-methyl-1-(S)-[[(dimethyl)amino]carbonyl]butyl]amino]-butanoic acid Prepared as described for Example 1, Part (b) by hydrolysis of the product of Part (a) above to give the title compound as a white solid; 35 mg.

MS; $MH^+ = 440$ $^1$H-NMR (CD$_3$OD) δ 8.31 (2H, s), 8.04–8.08 (2H, m), 7.63–7.68 (2H, m), 4.38 (1H, t, J=6 Hz), 3.82–3.89 (3H, m), 3.03 (3H, s), 2.88 (3H, s), 2.15–2.23 92H, m), 1.64–1.73 (3H, m), 0.90–0.94 (6H, m).

EXAMPLE 47

4-(1,3-Dihydro-1,3-dioxo-2H-benz[f]isoindol-2-yl)-2-(R)-[[3-methyl-1-(S)-[[(2-oxo-tetrahydro-thiophen-3-(R)-yl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(2-oxo-tetrahydro-thiophen-3-(R)-yl)amino]carbonyl]butyl]amino]-butanoic acid-1,1-dimethylethyl ester Prepared as described in Example 1, Part (a) using 3-(R)-amino-dihydrothiophen-2-one as $HNR^2R^3$ to afford the title compound as a white solid; 125 mg.

(b) 4-(1,3-Dihydro-1,3-dioxo-2H-benz[f]isoindol-2-yl)-2-(R)-[[3-methyl-1-(S)-[[(2-oxo-tetrahydro-thiophen-3-(R)-yl)amino]carbonyl]butyl]amino]-butanoic acid Prepared as described for Example 1, Part (b) by hydrolysis of the product of Part (a) above to give the title compound as a white solid; 65 mg.

MS; $MH^+ = 512$ $^1$H-NMR (CD$_3$OD) δ 8.33 (2H, s), 8.06–8.10 (2H, m), 7.65–7.68 (2H, m), 4.55 (1H, q, J=9, 15 Hz), 3.78–3.97 (4H, m), 3.20–3.33 (2H, m) 3.45–3.59 (1H, m), 2.05–2.24 (3H, m), 1.55–1.85 (3H, m) 0.90–0.95 (6H, m).

EXAMPLE 48

4-(1,3-Dihydro-1,3-dioxo-2H-benz[f]isoindol-2-yl)-2-(R)-[[3-methyl-1-(S)-[[(2-oxo-tetrahydro-thiophen-3-(S)-yl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(2-oxo-tetrahydro-thiophen-3-(S)-yl)amino]carbonyl]butyl]amino]-butanoic acid-1,1-dimethylethyl ester Prepared as described in Example 1, Part (a) using 3-(S)-aminodihydro-thiophen-2-one as $HNR^2R^3$ to afford the title compound as a white solid; 125 mg.

(b) 4-(1,3-Dihydro-1,3-dioxo-2H-benz[f]isoindol-2-yl)-2-(R)-[[3-methyl-(S)-1-[[(2-oxo-tetrahydro-thiophen-3-(S)-yl)amino]carbonyl]butyl]amino]-butanoic acid Prepared as described for Example 1, Part (b) by hydrolysis of the product of Part (a) above to give the title compound as a white solid; 96 mg.

MS; $MH^+ = 512$ $^1$H-NMR (CD$_3$OD) δ 8.32 (2H, s), 8.06–8.09 (2H, m), 7.64–7.68 (2H, m), 4.59 (1H, q, J=9,15 Hz), 3.98 (1H, t, J=6 Hz), 3.82–3.93 (3H, m) 3.19–3.33 (2H, m), 2.40–2.58 (1H, m), 2.10–2.30 (3H, m), 1.60–1.76 (3H, m), 0.89–0.94 (6H, m).

EXAMPLE 49

4-(1,3-Dihydro-1,3-dioxo-2H-benz[f]isoindol-2-yl)-2-(R)-[[3-methyl-1-(S)-[[(3-(R)-acetylamino-4-(S)-5-(S)-dihydroxy-6-(R)-hydroxymethyl-tetrahydro-pyran-2-yl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(3-(R)-acetylamino-4-(S)-5-(S)-dihydroxy-6-(R)-hydroxymethyl-tetrahydro-pyran-2-yl)amino]carbonyl]butyl]amino]-butanoic acid-1,1-dimethylethyl ester 200 mg of N-[(R)-1-[(1,1-dimethylethoxy)carbonyl]-3-(1,3-dihydro-1,3-dioxo-2H-benz[f]isoindol-2-yl)propyl]-L-leucine, prepared as in Example L, was added to 58 mg of 2-acetamido-1-amino-1,2-dideoxy-B-D-glucopyranose, 1.5 mL DMF, 0.5 mL DMSO. 0.5 mL of 0.45M hydroxybenzotriazolbenzotriazoltetramethyluronium hexafluorophosphate in DMF was added to the mixture followed by 0.66 mL of diisopropylethylamine. The mixture was stirred for 2.5 h, diluted with 30 mL ethyl acetate, washed two times with 20 mL of 10% sodium carbonate, washed with 20 mL brine, and dried with sodium sulfate. The solvents were removed by evaporation to give the title compound as a white solid; 61 mg.

(b) 4-(1,3-Dihydro-1,3-dioxo-2H-benz[f]isoindol-2-yl)-2-(R)-[[3-methyl-1-(S)-[[(3-(R)-acetylamino-4-(S)-5-(S)-dihydroxy-6-(R)-hydroxymethyl-tetrahydro-pyran-2-yl)amino]carbonyl]butyl]amino]-butanoic acid Prepared as described for Example 1, Part (b) by hydrolysis of the product of Part (a) above to give the title compound as a white solid; 21 mg.

MS; $MH^+ = 615$ $^1$H-NMR (CD$_3$OD) δ 8.40 (2H, s), 8.11–8.18 (2H, m), 7.70–7.78 (2H, m), 4.97 (1H, d, J=12 Hz), 3.36–3.99 (8H, m), 2.09–2.24 (2H, m), 1.95 (3H, s), 1.70–1.85 (1H, m), 1.50–1.65 (2H, m), 0.85–0.99 (6H, m).

EXAMPLE 50

4-(1,3-Dihydro-1,3-dioxo-2H-benz[f]isoindol-2-yl)-2-(R)-[[3-methyl-1-(S)-[[[benzyl-(2-hydroxyethyl)-]amino]carbonyl]butyl]amino]-butanoic acid (a) 4-(1,3-Dihydro-1,3-dioxo-2H-benz[f]isoindol-2-yl)-2-(R)-[[3-methyl-(S)-1-[[[benzyl-(2-hydroxyethyl)-]amino]carbonyl]butyl]amino]-butanoic acid-1,1-dimethylethyl ester Prepared as described in Example 1, Part (a) using 2-benzylaminoethanol as HNR²R³ to give the title compound as a white solid; 76 mg.

(b) 4-(1,3-Dihydro-1,3-dioxo-2H-benz[f]isoindol-2-yl)-2-(R)-[[3-methyl-(S)-1-[[[benzyl-(2-hydroxyethyl)-]amino]carbonyl]butyl]amino]-butanoic acid Prepared as described for Example 1, Part (b) by hydrolysis of the product of Part (a) above to give the title compound as a white solid; 26 mg.

$^1$H-NMR (CD$_3$OD) δ 8.38–8.41 (2H, m), 8.10–8.20 (2H, m), 7.69–7.90 (2H, m), 7.15–7.36 (5H, m), 4.80–5.10 (2H, m), 3.80–4.05 (3H, m), 3.40–3.75 (5H, m), 2.20–2.42 (2H, m), 1.60–1.90 (3H, m), 0.80–1.00 (6H, m).

EXAMPLE 51

4-(1,3-Dihydro-1,3-dioxo-2H-benz[f]isoindol-2-yl)-2-(R)-[[3-methyl-1-(S)-[3,4-dihydro-1H-isoquinoline-2-carbonyl]butyl]amino]-butanoic acid (a) 4-(1,3-Dihydro-1,3-dioxo-2H-benz[f]isoindol-2-yl)-2-(R)-[[3-methyl-1-(S)-[3,4-dihydro-1H-isoquinoline-2-carbonyl]butyl]amino]-butanoic acid-1,1-dimethylethyl ester Prepared as described in Example 1, Part (a) using 1,2,3,4-tetrahydroisoquinoline as HNR2R3 to give the title compound as a white solid; 274 mg.

(b) 4-(1,3-Dihydro-1,3-dioxo-2H-benz[f]isoindol-2-yl)-2-(R)-[[3-methyl-(S)-1-[3,4-dihydro-1H-isoquinoline-2-carbonyl]butyl]amino]-butanoic acid Prepared as described for Example 1, Part (b) by hydrolysis of the product of Part (a) above to give the title compound as a colorless oil; 51 mg.

MS; MH+ =527

$^1$H-NMR (CD$_3$OD) δ 8.33 (2H, s), 8.11 (2H, m), 7.72 (2H, m) 7.13 (4H, m), 4.56–4.84 (4H, m), 3.60–4.24 (6H, m), 2.78–3.08 (2H, m), 2.16–2.42 (2H, m), 1.64–1.96 (3H, m), 1.00 (6H, m).

EXAMPLE 52

4-(1,3-Dihydro-1,3-dioxo-2H-benz[f]isoindol-2-yl)-2-(R)-[[3-methyl-1-(S)-[4-methyl-piperazine-1-carbonyl]-butyl]amino]-butanoic acid (a) 4-(1,3-Dihydro-1,3-dioxo-2H-benz[f]isoindol-2-yl)-2-(R)-[[3[methyl-1-(S)-[4-methyl-piperazine-1-carbonyl]butyl]amino]-butanoic acid-1,1-dimethylethyl ester Prepared as described in Example 1, Part (a) using 4-methyl-piperazine as HNR²R³ to give the title compound as a white solid; 244 mg.

(b) 4-(1,3-Dihydro-1,3-dioxo-2H-benz[f]isoindol-2-yl)-2-(R)-[[3[methyl-1-(S)-[4-methyl-piperazine-1-carbonyl]butyl]amino]-butanoic acid Prepared as described for Example 1, Part (b) by hydrolysis of the product of Part (a) above to give the title compound; 175 mg.

MS; MH+ =495

1H-NMR (CD$_3$OD) δ 8.36 (2H, s), 8.13 (2H, m), 7.73 (2H, m), 4.52 (1H, m), 3.20–4.25 (11H, broad m), 2.97 (3H, s), 2.30 (2H, m), 1.80 (3H, m), 1.02 (6H, m).

EXAMPLE 53

4-(1,3-Dihydro-1,3-dioxo-2H-benz[f]isoindol-2-yl)-2-(R)-[[3-methyl-1-(S)-[1-oxo-[1,4]thiazinone-4-carbonyl]butyl]amino]-butanoic acid (a) 4-(1,3-Dihydro-1,3-dioxo-2H-benz[f]isoindol-2-yl)-2-(R)-[[3-methyl-1-(S)-[1-oxo-[1,4]thiazinone-4-carbonyl]butyl]amino]butanoic acid-1,1-dimethylethyl ester Prepared as described in Example 1, Part (a) using [1,4]thiazinane as HNR²R³ to afford the title compound as a white solid; 480 mg.

(b) 4-(1,3-Dihydro-1,3-dioxo-2H-benz[f]isoindol-2-yl)-2-(R)-[[3[methyl-1-(S)-[1-oxo-[1,4]thiazinone-4-carbonyl]butyl]amino]butanoic acid Prepared as described for Example 1, Part (b) by hydrolysis of the product of Part (a) above to give the title compound as a white solid; 86 mg.

MS; MH+ =514

1H-NMR (CD$_3$OD) δ 8.42 (2H, s), 8.14 (2H, m), 7.74 (2H, m), 3.50–4.62 (10H, m), 2.90–3.15 (4H, m), 2.31 (2H, m), 1.80 (3H, m), 1.02 (6H, m).

EXAMPLE 54

4-(1,3-Dihydro-1,3-dioxo-2H-benz[f]isoindol-2-yl)-2-(R)-[[3-methyl-1-(S)-[morpholine-4-carbonyl]butyl]amino]-butanoic acid (a) 4-(1,3-Dihydro-1,3-dioxo-2H-benz[f]isoindol-2-yl)-2-(R)-[[3-methyl-1-(S)-[morpholine-4-carbonyl]-butyl]amino]-butanoic acid -1,1-dimethylethyl ester Prepared as described in Example 1, Part (a) using morpholine as HNR²R³ to give the title compound an oil; 240 mg.

(b) 4-(1,3-dihydro-1,3-dioxo-2H-benz[f]isoindol-2-yl)-2-(R)-[[3-methyl-1-(S)-[morpholine-4-carbonyl]butyl]amino]-butanoic acid Prepared as described for Example 1, Part (b) by hydrolysis of the product of Part (a) above to give the title compound as a white solid; 145 mg.

MS; MH+ =482

1H-NMR (CD$_3$OD) δ 8.36 (2H, s), 8.12 (2H, m), 7.72 (2H, m), 4.47 (1H, m), 4.13 (1H, m), 3.43–4.06 (10H, m), 2.29 (2H, m) 1.80 (3H, M), 1.02 (6H, m).

EXAMPLE 55

4-(1,3-Dihydro-1,3-dioxo-2H-benz[f]isoindol-2-yl)-2-(R)-[[3-methyl-1-(S)-[4-(2-3-dihydroxy-propyl)-piperazine-1-carbonyl]butyl]amino]-butanoic acid (a) 4-(1,3-Dihydro-1,3-dioxo-2H-benz[f]isoindol-2-yl)-2-(R)-[[3-methyl-1-(S)-[4-(2-3-dihydroxy-propyl)-piperazine-1-carbonyl]butyl]amino]-butanoic acid-1,1-dimethylethyl ester Prepared as described in Example 1, Part (a) using 3-piperazin-1-yl-propane-1,2-diol as HNR²R³ to afford the title compound as a white solid; 134 mg.

(b) 4-(1,3-Dihydro-1,3-dioxo-2H-benz[f]isoindol-2-yl)-2-(R)-[[3-methyl-1-(S)-[4-(2-3-dihydroxy-propyl)-piperazine-1-carbonyl]butyl]amino]-butanoic acid Prepared as described for Example 1, Part (b) by hydrolysis of the product of Part (a) above to give the title compound as a white solid; 96 mg.

MS; MH+ =555

¹H-NMR (CD₃OD) δ 8.33 (2H, s), 8.06–8.10 (2H, m) 7.64–7.68 (2H, m), 4.25–4.38 (1H, m), 3.95–4.10 (2H, m), 3.60–3.90 (4H, m), 3.25–3.59 (10H, m), 2.10–2.25 (2H, m), 1.60–1.78 (3H, m), 0.90–0.99 (6H, m).

EXAMPLE 56

4-(1,3-Dihydro-1,3-dioxo-2H-benz[f]isoindol-2-yl)-2-(R)-[[3-methyl-1-(S)-[3,4,5,6-tetrahydro-H-[2,3]bipyridinyl-1-carbonyl]butyl]amino]-butanoic acid (a) 4-(1,3-Dihydro-1,3-dioxo-2H-benz[f]isoindol-2-yl)-2-(R)-[[3-methyl-1-(S)-[3,4,5,6-tetrahydro-H-[2,3]bipyridinyl-1-carbonyl]butyl]amino]-butanoic acid-1,1-dimethylethyl ester Prepared as described in Example 1, Part (a) using 1,2,3,4,5,6-hexahydro-[2,3′]-bipyridinyl as HNR²R³ to give the title compound as a tan solid; 135 mg.

(b) 4-(1,3-Dihydro-1,3-dioxo-2H-benz[f]isoindol-2-yl)-2-(R)-[[3-methyl-1-(S)-[3,4,5,6-tetrahydro-H-[2,3]bipyridinyl-1-carbonyl]butyl]amino]-butanoic acid Prepared as described for Example 1, Part (b) by hydrolysis of the product of Part (a) above to give the title compound as a white solid; 50 mg.

MS; MH⁺ = 557

¹H-NMR (CD₃OD) δ 8.50–8.70 (1H, m), 8.42 (2H, s), 8.10–8.20 (3H, m), 7.70–7.85 (4H, m), 5.95–5.96 (1H, m), 4.50–4.65 (1H, m), 3.75–4.15 (4H, m), 3.10–3.25 (1H, m), 2.30–2.50 (2H, m), 2.00–2.19 (1H, m), 1.60–1.95 (7H, m), 0.95–1.10 (6H, m).

EXAMPLE 57

4-(1,3-Dihydro-1,3-dioxo-2H-benz[f]isoindol-2-yl)-2-(R)-[[3-methyl-1-(S)-[[(1-methyl-8-oxo-1,7-diaza-cyclotridec-9-(S)-yl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(1-methyl-8-oxo-1,7-diaza-cyclotridec-9-(S)-yl)amino]carbonyl]butyl]amino]-butanoic acid-1,1-dimethylethyl ester Prepared as described in Example 1, Part (a) using 9-(S)-amino-1-methyl-1,7-diaza-8-onecyclotridecane as HNR²R³ to give the title compound.

(b) 4-(1,3-Dihydro-1,3-dioxo-2H-benz[f]isoindol-2-yl)-2-(R)-[[3-methyl-1-(S)-[[(1-methyl-8-oxo-1,7-diaza-cyclotridec-9-(S)-yl)amino]carbonyl]butyl]amino]-butanoic acid Prepared as described for Example 1, Step (b) by hydrolysis of the product of Part (a) above to give the title compound as a white solid; 108 mg.

MS; MH⁺ = 622

¹H-NMR (CD₃OD) δ 8.52 and 8.28 (1H, m), 8.39 (2H, s), 8.15 (2H, m), 7.75 (2H, m), 4.47 and 4.27 (1H, m), 3.84–4.10 (4H, m), 3.66 (1H, m), 2.80–3.25 (5H, m), 2.84 (3H, s), 2.20–2.42 (2H, m), 1.20–2.20 (15H, m), 0.96 (6H, m).

EXAMPLE 58

4-(1,3-Dihydro-1,3-dioxo-2H-benz[f]isoindol-2-yl)-2-(R)-[[3-methyl-1-(S)-[[methyl-1-methyl-piperidin-4-yl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[methyl-(1-methyl-piperidin-4-yl)amino]carbonyl]butyl]amino]-butanoic acid-1,1-dimethylethyl ester Prepared as described in Example 1, Part (a) using methyl-(1-methyl-piperidin-4-yl)amine as HNR²R³ to afford the title compound as a tan solid; 136 mg.

(b) 4-(1,3-Dihydro-1,3-dioxo-2H-benz[f]isoindol-2-yl)-2-(R)-[[3-methyl-1-(S)-[[methyl-(1-methyl-piperidin-4-yl)amino]carbonyl]butyl]amino]-butanoic acid Prepared as described for Example 1, Part (b) by hydrolysis of the product of Part (a) above to give the title compound as a white solid; 65 mg.

MS; MH⁺ = 523

¹H-NMR (CD₃OD) δ 8.41 (2H, s), 8.14–8.18 (2H, m), 7.73–7.78 (2H, m), 4.57–4.61 (1H, m), 4.39–4.56 (1H, m), 3.87–4.01 (3H, m), 3.50–3.67 (2H, m), 3.06–3.22 (2H, m), 3.03 (3H, s), 2.06–2.35 (4H, m) 1.67–2.02 (5H, m), 0.97–1.04 (6H, m).

EXAMPLE 59

4-(1,3-Dihyro-1,3-dioxo-2H-benz[f]isoindol-2-yl)-2-(R)-[[3-methyl-1-(S)-{[(4-hydroxy-1,1dioxo-tetrahydro-thiophen-3-yl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(4-hydroxy-1,1-dioxo-tetrahydro-thiophen-3-yl)amino]carbonyl]butyl]amino]-butanoic acid-1,1-dimethylethyl ester Prepared as described in Example 1, Part (a) using 4-(R)-amino-1,1-dioxo-tetrahydro-thiophen-3-(R)-ol as HNR²R³ to give the title compound as a white solid; 132 mg.

(b) 4-(1,3-Dihydro-1,3-dioxo-2H-benz[f]isoindol-2-yl)-2-(R)-[[3-methyl-1-(S)-[[(4-hydroxy-1,1-dioxo-tetrahydro-thiophen-3-yl)amino]carbonyl]butyl]amino]-butanoic acid Prepared as described for Example 1, Part (b) by hydrolysis of the product of Part (a) above to give the title compound as a white solid; 27 mg.

MS; MH⁺ = 546

¹H-NMR (CD₃OD) δ 8.41 (2H, s), 8.14–8.17 (2H, m), 7.72–7.76 (2H, m), 4.66–4.74 (2H, m), 4.53–4.56 (1H, m), 3.79–4.00 (4H, m), 3.34–3.47 (3H, m), 2.20–2.35 (2H, m), 1.67–1.85 (3H, m), 0.94–1.02 (6H, m).

EXAMPLE 60

4-(1,3-Dihydro-1,3-dioxo-2H-benz[f]isoindol-2-yl)-2-(R)-[[3-methyl-1-(S)-(4-ethoxycarbonylmethyl-piperazine-1-carbonyl)butyl]amino]-butanoic acid (a) 4-(1,3-Dihydro-1,3-dioxo-2H-benz[f]isoindol-2-yl)-2-(R)-[[3-methyl-1-(S)-(4-ethoxycarbonylmethyl-piperazine-1-carbonyl)butyl]amino]-butanoic acid-1,1-dimethylethyl ester Prepared as described in Example 1, Part (a) using piperazin-1-yl-acetic acid ethyl ester as HNR²R³ to afford the title compound as a tan solid; 132 mg.

(b) 4-(1,3-Dihydro-1,3-dioxo-2H-benz[f]isoindol-2-yl)-2-(R)-[[3-methyl-1-(S)-(4-ethoxycarbonylmethyl-piperazine-1-carbonyl)butyl]amino]-butanoic Prepared as described for Example 1, Part (b) by hydrolysis of the product of Part (a) above to give the title compound as a white solid; 28 mg.

MS; MH⁺ = 567

¹H-NMR (CD₃OD) δ 8.41 (2H, s), 8.14–8.18 (2H, m), 7.71–7.78 (2h, m), 4.39–4.43 (1H, m), 4.19 (2H, q, J = 6,9 Hz), 3.80–4.09 (4H, m), 3.53–3.70 (1H, m), 2.96–3.12 (4H, m), 2.19–2.33 (2H, m), 1.69–1.81 (3H, m), 1.25 (2H, t, J = 6,9 Hz), 0.94–0.99 (6H, m).

EXAMPLE 61

4-(1,3-Dihydro-1,3-dioxo-2H-benz[f]isoindol-2-yl)-2-(R)-[[3-methyl-1-(S)-[[(1,1-dioxo-tetrahydro-thiophen-3-yl)-methyl-amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(1,1-dioxo-tetrahydro-thiophen-3-yl)-methyl-amino]carbonyl]butyl]amino]-butanoic acid-1,1-dimethylethyl ester Prepared as described in Example 1, Part (a) using (1,1-dioxo-tetrahydro-thiophen-3-yl)-methyl-amine as HNR²R³ to give the title compound as a tan solid; 199 mg.

(b) 4-(1,3-Dihydro-1,3-dioxo-2H-benz[f]isoindol-2-yl)-2-(R)-[[3-methyl-1-(S)-[[(1,1-dioxo-tetrahydro-thiophen-3-yl)-methyl-amino]carbonyl]butyl]amino]-butanoic acid Prepared as described for Example 1, Part (b) by hydrolysis of the product of Part (a) above to give the title compound as a white solid; 89 mg.

MS; MH+ = 544

$^1$H-NMR (CD$_3$OD) δ 8.41 (2H, s), 8.15–8.18 (2H, m), 7.74–7.77 (2H, m), 5.15–5.20 (1H, m), 4.42–4.43 (1H, m), 3.92–4.05 (3H, m), 3.06–3.40 (3H, m), 3.11 (3H, m), 2.96–2.98 (1H, m), 2.26–2.42 (4H, m), 1.74–1.86 (3H, m), 1.01–1.04 (6H, m).

EXAMPLE 62 and EXAMPLE 63

4-(1,3-Dihydro-1,3-dioxo-2H-benz[f]isoindol-2-yl)-2-(R)-[[3-methyl-1-(S)-[2-(R)-(pyridin-3-yl)-pyrrolidinecarbonyl]butyl]amino]-butanoic acid and 4-(1,3-Dihydro-1,3-dioxo-2H-benz[f]isoindol-2-yl)-2-(R)-[[3-methyl-1-(S)-[2-(S)-(pyridin-3-yl)-pyrrolidinecarbonyl]butyl]amino]-butanoic acid (a) 4-(1,3-Dihydro-1,3-dioxo-2H-benz[f]isoindol-2-yl)-2-(R)-[[3-methyl-1-(S)-(pyridin-3-yl)-pyrrolidinecarbonyl]butyl]amino]-butanoic acid 1,1-dimethylethyl ester Prepared as described in Example 1, Part (a) using 3-pyrrolidin-2-yl-pyridine as HNR²R³ to afford the title compound as a dark solid; 145 mg.

(b) 4-(1,3-Dihydro-1,3-dioxo-2H-benz[f]isoindol-2-yl)-2-(R)-[[3-methyl-1-(S)-[2-(pyridin-3-yl)pyrrolidinecarbonyl]butyl]amino]-butanoic acid Prepared as described for Example 1, Part (b) by hydrolysis of the product of Part (a) above to give the title compound as a white solid; 52 mg. The R and S stereoisomers were separated by RP-HPLC on a C-18 column using a 15–80% CH$_3$CN in H$_2$O with .1% T.F.A. gradient over 30 minutes to give two peaks eluting at 11.78 minutes and 12.03 minutes.

MS; MH+ = 543

[11.78 minute peak] $^1$H-NMR (CD$_3$OD) δ 8.77–8.78 (1H, m), 8.62–8.63 (1H, m), 8.41 (2H, s), 8.15–8.19 (2H, m), 7.82–7.86 (1H, m), 7.74–7.77 (2H, m), 5.21–5.24 (1H, m), 4.21–4.26 (1H, m), 3.69–4.04 (5H, m), 2.47–2.54 (1H, m), 1.74–2.30 (8H, m), 1.02–1.07 (6H, m). [12.03 minute peak] $^1$H-NMR (CD$_3$OD) δ 8.65–8.70 (2H, m), 8.39 (2H, s), 8.29–8.37 (1H, m), 8.13–8.17 (2H, m) 7.73–7.88 (2H, m), 5.24 (1H, t, J=6 Hz), 4.32 (1H, t, J=6 Hz), 3.82–4.05 (5H, m), 2.51–2.57 (1H, m), 2.26–2.35 (2H, m), 2.13–2.22 (2H, m), 1.95–2.04 (3H, m), 1.76–1.81 (3H, m), 1.01–1.06 (6H, m).

EXAMPLE 64 and EXAMPLE 65

4-(1,3-Dihydro-1,3-dioxo-2H-benz[f]isoindol-2-yl)-2-(R)-[[3-methyl-1-(S)-[3-oxo-2-(R)-phenyl-piperazine-1-carbonyl]butyl]amino]-butanoic acid and 4-(1,3-Dihydro-1,3-dioxo-2H-benz[f]isoindol-2-yl)-2-(R)-[[3-methyl-1-(S)-[3-oxo-2-(S)-phenyl-piperazine-1-carbonyl]butyl]amino]-butanoic acid (a) 4-(1,3-Dihydro-1,3-dioxo-2H-benz[f]isoindol-2-yl)-2-(R)-[[3-methyl-1-(S)-[3-oxo-2-phenyl-piperazine-1-carbonyl]butyl]amino]-butanoic acid-1,1-dimethylethyl ester Prepared as described in Example 1, Part (a) using 3-oxo-2-phenyl-piperazine as HNR²R³ to give the title compound as a tan solid; 137 mg.

(b) 4-(1,3-Dihydro-1,3-dioxo-2H-benz[f]isoindol-2-yl)-2-(R)-[[3-methyl-1-(S)-[3-oxo-2-phenyl-piperazine-1-carbonyl]butyl]amino]-butanoic acid Prepared as described for Example 1, Part (b) by hydrolysis of the product of Part (a) above to give the title compound as a white solid; 38 mg. The R and S stereoisomers were separated by RP-HPLC on a C-18 column using a 15–80% CH$_3$CN in H$_2$O with 0.1% T.F.A. gradient over 30 minutes to give two peaks eluting at 14.64 minutes and 15.28 minutes.

MS; MH+ = 571

[14.64 minute peak] $^1$H-NMR (CD$_3$OD) δ 8.51 (2H, s), 8.25–8.35 (2H, m), 7.76–7.80 (2H, m), 7.16–7.45 (5H, m), 5.67 (1H, s), 4.20–4.23 (1H, m), 3.12–3.87 (7H, m), 2.03–2.12 (2H, m), 1.40–1.60 (2H, m), 1.05–1.39 (1H, m), 0.93 (3H, d, J=6 Hz), 0.84 (3H, J=6 Hz).

[15.28 minute peak] $^1$H-NMR (CD$_3$OD) δ 8.51 (2H, s), 8.24–8.31 (2H, m), 7.76–7.78 (2H, M), 7.26–7.38 (5H, m), 5.80 (1H, s), 3.70–4.15 (4H, m), 3.20–3.50 (4H, m), 1.95–2.15 (2H, m), 1.60–1.80 (1H, m), 1.20–1.45 (2H, m), 0.86 (3H, d, J=6 Hz), 0.79 (3H, d, J=6 Hz).

EXAMPLE 66

4-(1,3-Dihydro-1,3-dioxo-2H-benz[f]isoindol-2-yl)-2-(R)-[[3-methyl-1-(S)-[(pyridine-3-carbonyl-hydrazino)-carbonyl]butyl]amino]-butanoic acid (a) 4-(1,3-Dihydro-1,3-dioxo-2H-benz[f]isoindol-2-yl)-2-(R)-[[3-methyl-1-(S)-[(pyridine-3-carbonylhydrazino)carbonyl]butyl]amino]-butanoic acid-1,1-dimethylethyl ester Prepared as described in Example 1, Part (a) using nicotinic acid hydrazide as HNR²R³ to afford the title compound as a white solid; 114 mg.

(b) 4-(1,3-Dihydro-1,3-dioxo-2H-benz[f]isoindol-2-yl)-2-(R)-[[3-methyl-1-(S)-[(pyridine-3-carbonylhydrazino)carbonyl]butyl]amino]-butanoic acid Prepared as described for Example 1, Part (b) by hydrolysis of the product of Part (a) above to give the title compound as a white solid; 90 mg.

MS; MH+ = 532

$^1$H-NMR (CD$_3$OD) δ 8.91 (1H, s), 8.65–8.67 (1H, m), 8.38 (2H, s), 8.11–8.16 (2H, m), 8.02–8.06 (1H, m), 7.72–7.77 (2H, m), 7.37–7.42 (1H, m), 4.20 (1H, t, J=6 Hz), 3.93–4.10 (3H, m), 2.41 2.48 (2H, m), 1.73–1.99 (3H, m), 1.06 (3H, d, J=6 Hz), 1.03 (3H, d, J=6 Hz).

EXAMPLE 67

4-(1,3-Dihydro-1,3-dioxo-2H-benz[f]isoindol-2-yl)-2-(R)-[[3-methyl-1-(S)-[[(benzenesulfonyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(benzenesulfonyl)amino]carbonyl]butyl]amino]-butanoic acid-1,1 dimethylethyl ester Prepared as described in Example 1, Part (a) using benzenesulfonamide as $HNR^2R^3$ to give the title compound as a white solid; 94 mg.

(b) 4-(1,3-Dihydro-1,3-dioxo-2H-benz[f]isoindol-2-yl)-2-(R)-[[3-methyl-1-(S)-[[(benzenesulfonyl)amino]carbonyl]butyl]amino]-butanoic acid Prepared as described for Example 1, Part (b) by hydrolysis of the product of P art (a) above to give the title compound as a white solid; 55 mg.

MS; $MH^+ = 552$ $^1$H-NMR (CD$_3$OD) δ 8.32 (2H, s), 8.07–8.10 (2H, m), 7.91–7.94 (2H, m), 7.65–7.68 (2H, m), 7.43–7.54 (3H, m), 3.71–3.80 (2H, m), 3.64–3.68 (1H, m), 3.54–3.59 (1H, m), 2.02–2.10 (2H, m), 1.45–156 (3H, d, J=6 Hz), 0.77 (3H, d, J=6 Hz).

EXAMPLE 68

4-(1,3-Dihydro-1,3-dioxo-2H-benz[f]isoindol-2-yl)-2-(R)-[[3-methyl-1-(S) -[[(3-aminobenzyl)amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(3-aminobenzyl)amino]carbonyl]butyl]amino]-butanoic acid-1,1-dimethylethyl ester 200 mg of 4-(1,3-dihydro-1,3-dioxo-2H-benz[f]isoindol-2-yl)-2-(R)-[[3-methyl-1-(S)-[[(3-nitrobenzyl)amino]carbonyl]butyl]amino]-butanoic acid-1,1-dimethylethyl ester, prepared as in Example 30 where the protecting group R$^p$, 1,1-dimethylethyl was not removed following the condensation reaction seen in Scheme 1, was added to ethanol:H2O (20:1). 10 mL of ethyl acetate was added and the mixture was stirred with heating until the solid dissolved. The mixture was cooled to RT and 20 mg of 10% palladium over activated carbon was added. The mixture was purged with nitrogen. The mixture was purged with hydrogen, and stirred under hydrogen for 3 h. The mixture was filtered and washed with ethyl acetate. The solvents were removed by evaporation and the residue was purified by reverse phase H.P.L.C. to give a white solid; 83 mg (b) 4-(1,3-Dihydro-1,3-dioxo-2H-benz[f]isoindol-2-yl)-2-(R)-[[3-methyl-1-(S)-[[(3-aminobenzyl)amino]carbonyl]butyl]amino]-butanoic acid Prepared as described for Example 1, Part (b) by hydrolysis of the product of Part (a) above to give the title compound as a solid; 64 mg.

MS; $MH^+ = 517$ $^1$H-NMR (CD$_3$OD) δ 8.31 (2H, m), 8.06–8.08 (2H, m), 7.64–7.68 (2H, m), 7.26 (1H, m), 7.08 (2H, m), 6.97 (1H, d, J=9 Hz), 4.25 (2H, ABq, Jab=15 Hz), 3.70–3.85 (4H, m), 2.14–2.20 (2H, m), 1.56–1.73 (3H, m), 0.87 (3H, d, J=6 Hz), 0.85 (3H, d, J=6 Hz).

EXAMPLE 69

4-(1,3-Dihydro-1,3-dioxo-2H-benz[f]isoindol-2-yl)-2-(R)-[[3-methyl-1-(S)-[[[4-(trifluoro-methansulfonylamino)benzyl]amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[[4-(trifluoromethansulfonylamino)benzyl]amino]carbonyl]butyl]amino]-butanoic acid-1,1-dimethylethyl ester 172 mg of 4-(1,3-dihydro-1,3-dioxo-2H-benz[f]isoindol-2-yl)-2-(R)-[[3-methyl-1-(S)-[[4-nitrobenzyl)amino]carbonyl]butyl]amino]-butanoic acid-1,1-dimethylethyl ester, prepared as in Example 31 where the protecting group Rp, 1,1-dimethylethyl was not removed following the condensation reaction seen in Scheme 1, was added to 3 mL dichloromethane under nitrogen. 0.042 mL triethylamine was added to the mixture and stirred for 5 min. The mixture was cooled to −78° C. and stirred for 5 min. 0.054 mL trifluoromethan esulfonic anhydride was added to the mixture and stirred for 30 min. The solvents were removed by evaporation and the tan solid was dissolved in MeOH:acetonitrile (1:1), filtered, and purified by reverse phase H.P.L.C. to give a white solid; 115 mg.

(b) 4-(1,3-Dihydro-1,3-dioxo-2H-benz[f]isoindol-2-yl)-2-(R)-[[3-methyl-1-(S)-[[[4-(trifluoromethansulfonylamino)benzyl]amino]carbonyl]butyl]amino]-butanoic acid Prepared as described for Example 1, Part (b) by hydrolysis of the product of Part (a) above to give the title compound as a solid; 63 mg.

MS; $MH^+ = 649$ $^1$H-NMR (CD$_3$OD) δ 8.32 (2H, s), 8.05–8.08 (2H, m), 7.64–7.67 (2H, m), 7.22–7.25 (2H, m), 7.12–7.15 (2H, m), 4.23–4.36 (2H, m), 3.74–3.90 (4H, m), 2.18–2.20 (2H, m), 1.70–1.77 (1H, m), 1.49–1.65 (2H, m), 0.85–0.87 (6H, m).

EXAMPLE 70 and EXAMPLE 71

4-(1,3-Dihydro-1,3-dioxo-2H-benz[f]isoindol-2-yl)-2-(R)-[[3-methyl-1-(S)-[[[2-hydroxy-(R)-bicyclo[4.3.0-]nona-3,6(1)-diene]amino]carbonyl]butyl]amino]-butanoic acid and 4-(1,3-Dihydro-1,3-dioxo-2H-benz[f]isoindol-2-yl)-2-(R)-[[3-methyl-1-(S)-[[[2-hydroxy-(S)-bicyclo[4.3.0-]nona-3,6(1)-diene]amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[[2-hydroxy-bicyclo[4.3.0-]nona-3,6(1)-diene]amino]carbonyl]butyl]amino]-butanoic acid-1,1-dimethylethyl ester Prepared as described in Example 1, Part (a) using 1-amino-2-hydroxybicyclo[4.3.0]nona-3,6(1)-diene as $HNR^2R^3$ to give the title compounds. The R and S stereoisomers were separated by RP-HPLC on a C-18 column using a 15–80% CH$_3$CN in H$_2$O with 0.1% T.F.A. gradient over 30 minutes to give two peaks eluting at 20.79 minutes and 21.58 minutes. The 20.79 minute and 21.58 minute eluting peaks were dried separately to yield the title compounds as white solids; 54 mg and 109 mg, respectively.

(b) 4-(1,3-Dihydro-1,3-dioxo-2H-benz[f]isoindol-2-yl)-2-(R)-[[3-methyl-1-(S)-[[[2-hydroxy-(R)-bicyclo[4.3.0]nona-3,6(1)-diene]amino]carbonyl]butyl]amino]-butanoic acid and 4-(1,3-Dihydro-1,3-dioxo-2H-benz[f]isoindol-2-yl)-2-(R)-[[3-methyl-1-(S)-[[[2-hydroxy-(S)-bicyclo[4.3.0-]nona-3,6(1)-diene]amino]carbonyl]butyl]amino]-butanoic acid Prepared as described for Example 1, Part (b) by hydrolysis of the products of Part (a) above to give the title compounds as white solids; 21 mg and 55 mg, respectively.

MS; MH+ = 544

[20.79 minute peak] $^1$H-NMR (CD$_3$OD) δ 8.39 (2H, s), 8.17–8.12 (2H, m), 7.78–7.72 (2H, m), 7.32–7.09 (4H, m), 5.31 (1H, m), 4.56–4.51 (1H, m), 4.12–3.91 (4H, m), 3.15–2.88 (2H, m), 2.41–2.31 (2H, m), 1.94–1.74 (3H, m), 1.01 (6H, m).

[21.58 minute peak] $^1$H-NMR (CD$_3$COCD$_3$) δ 8.36 (2H, s), 8.21–8.18 (2H, m), 8.03–8.00 (1H, m) 7.78–7.74 (2H, m), 7.21–7.16 (4H, m), 5.30–5.25 (1H, m), 4.60–4.55 (1H, m), 4.21–3.95 (4H, m), 3.03 (1H, ABq, J=16.0, 5.0 Hz), 2.81 (1H, ABq, J=16.0, 1.0 Hz), 2.45–2.41 (2H, m), 1.95–1.80 (3H, m), 0.99 (6H, m).

EXAMPLE 72

4-(1,3-Dihydro-1,3-dioxo-2H-benz[f]isoindol-2-yl)-2-(R)-[[3-methyl-1-(S)-[[(N-methyl-pyrrolidine)-methyl-amino]carbonyl]butyl]amino]-butanoic acid (a) 4-(1,3-Dihydro-1,3-dioxo-2H-benz[f]isoindol-2-yl)-2-(R)-[[3-methyl-1-(S)-[[(N-methyl-pyrrolidine)-methyl-amino]carbonyl]butyl]amino]-butanoic acid-1,1-dimethylethyl ester Prepared as described in Example 1, Part (a) using (N-methyl-pyrrolidine)-methyl-amine as HNR$^2$R$^3$ to afford the title compound as a solid; 236 mg.

(b) 4-(1,3-Dihydro-1,3-dioxo-2H-benz[f]isoindol-2-yl)-2-(R)-[[3-methyl-1-(S)-[[(N-methyl-pyrrolidine)-methyl-amino]carbonyl]butyl]amino]-butanoic acid Prepared as described for Example 1, Part (b) by hydrolysis of the product of Part (a) above to give the title compound as a white solid; 158 mg.

MS; MH+ = 509

$^1$H-NMR (CD$_3$OD) δ 8.41 (2H, m), 8.19–8.14 (2H, m), 7.78–7.74 (2H, m), 4.50–4.20 (2H, m), 4.00–3.70 (5H, m), 3.15 (3H, m), 3.10–3.00 (1H, m), 2.95 (3H, m), 2.60–2.10 (5H, m), 1.90–1.60 (3H, m), 1.05–0.97 (6H, m).

EXAMPLE 73

4-(1,3-Dihydro-1,3-dioxo-2H-benz[f]isoindol-2-yl)-2-(R)-[[3-methyl-1-(S)-[(N-ethoxycarbonylmethyl-piperazine)-1-carbonyl]butyl]amino]-butanoic acid (a) 4-(1,3-Dihydro-1,3-dioxo-2H-benz[f]isoindol-2-yl)-2-(R)-[[3-methyl-1-(S)-[N-ethoxycarbonylmethyl-piperazine-1-carbonyl]butyl]amino]-butanoic acid-1,1-dimethylethyl ester Prepared as described in Example 1, Part (a) using N-ethoxycarbonylmethyl-piperazine as HNR$^2$R$^3$ to afford the title compound as a solid; 561 mg.

(b) 4-(1,3-Dihydro-1,3-dioxo-2H-benz[f]isoindol-2-yl)-2-(R)-[[3-methyl-1-(S)-[N-ethoxycarbonylmethyl-piperazine-1-carbonyl]butyl]amino]-butanoic acid Prepared as described for Example 1, Part (b) by hydrolysis of the product of Part (a) above to give the title compound as a white solid; 34 mg.

MS; MH+ = 539

$^1$H-NMR (CD$_3$OD) δ 8.41 (2H, s), 8.19–8.14 (2H, m), 7.77–7.72 (2H, m), 4.40 (1H, m), 4.20 (1H, m), 4.10–3.70 (7H, m), 3.60 (1H, m), 3.40 (4H, m), 2.25 (2H, m), 1.81–1.72 (3H, m), 1.00 (6H, m).

Further examples of compounds of the present invention are those of the formula (I) prepared according to the procedure described in Scheme 2, wherein a compound of the formula (II) is prepared as described for Example N, where:

R$^1$ is isobutyl;
R$^2$ is hydrogen;
n is 0;
R$^6$ is hydrogen;
R$^7$ is phenyl;
R$^8$ is hydroxyl.

EXAMPLE 74

2-(R)-[1-(S)-(Benzylamino)carbonyl-3-methyl-btuylamino]-4-(5-bromo-1,3-dioxo-1,3-dihydro-isoindol-2-yl)-butanoic acid (a) 2-(R)-[1-(S)-(Benzylamino)carbonyl-3-methyl-butylamino]-4-(5-bromo-1,3-dioxo-1,3-dihydro-isoindol-2-yl)-butanoic acid-1,1-dimethylethyl ester 325 mg of 2-(R)-[1-(S)-(benzylamino)carbonyl-3-methyl-butylamino]-4-hydroxy-butanoic acid-1,1-dimethylethyl ester, prepared as described for Example N, was added to 10 mL DMF, followed by 226 mg 5-bromo-1,3-dihydro-1,3-dioxo-2H-isoindole. 231 mg of triphenylphosphine was added and the mixture was cooled to 0° C. 0.14 mL diethyl azodicarboxylate was added and the mixture was warmed to RT with stirring for 16 h. The solvents were removed by evaporation and the resulting residue was purified by reverse phase H.P.L.C. to give the title compound; 53 mg.

(b) 2-(R)-[1-(S)-(Benzylamino)carbonyl-3-methyl-butylamino]-4-(5-bromo-1,3-dioxo-1,3-dihydro-isoindol-2-yl)-butanoic acid Prepared as described for Example 1, Part (b) by hydrolysis of the product of Part (a) above to give the title compound as a solid; 16.3 mg. MS; MH+ = 532.1274

$^1$H-NMR (CD$_3$OD) δ 7.9 (2H, m), 7.6 (1H, d), 7.2 (5H, m), 4.4–4.2 (2H, dd), 3.8–3.6 (4H, m), 2.2 (2H, m), 1.8–1.6 (3H, m), 0.9 (6H, dd).

EXAMPLE 75

2-(R)-[1-(S)-(Benzylamino)carbonyl-3-methyl-butylamino]-4-(5-propoxy-1,3-dioxo-1,3-dihydro-isoindol-2-yl)-butanoic acid (a) 2-(R)-[1-(S)-(Benzylamino)carbonyl-3-methyl-butylamino]-4-(5-propoxy-1,3-dioxo-1,3-dihydro-isoindol-2-yl)-butanoic acid-1,1-dimethylethyl ester Prepared as described for Example 70 using 1,3-dihydro-5-(1-propyl)oxy-1,3-dioxo-2H-isoindole as a compound of Formula (V) to afford the title compound as a solid.

(b) 2-(R)-[1-(S)-(Benzylamino)carbonyl-3-methyl-butylamino]-4-(5-propoxy-1,3-dioxo-1,3-dihydro-isoindol-2-yl)-butanoic acid Prepared as described for Example 1, Part (b) by hydrolysis of the product of Part (a) above to give the title compound as a solid; 54.2 mg. MS; MH+ = 510.2604

$^1$H-NMR (CD$_3$OD) δ 7.7 (1H, d), 7.3 (1H, s), 7.2 (5H, m), 7.1 (1H, d), 4.4–4.2 (2H,dd), 4.0 (2H, t), 3.8 (1H, t), 3.6–3.4 (3H, m), 2.1 (2H, m), 1.8 (m, 4H), 1.6 (1H, m), 1.0 (3H, t), 0.9 (6H, dd).

EXAMPLE 76

2-(R)-[1-(S)-(Benzylamino)carbonyl-3-methyl-butylamino]-4-(5-nitro-1,3-dioxo-1,3-dihydro-isoindol-2-yl)-butanoic acid (a) 2-(R)-[1-(S)-(Benzylamino)carbonyl-3-methyl-butylamino]-4-(5-nitro-1,3-dioxo-1,3-dihydro-isoindol-2-yl)-butanoic acid-1,1-dimethylethyl ester Prepared as described for Example 70 using 1,3-dihydro-5-nitro-1,3-dioxo-2H-isoindole as a compound of Formula (V) to afford the title compound as a white solid; 72 mg.

(b) 2-(R)-[1-(S)-(Benzylamino)carbonyl-3-methyl-butylamino]-4-(5-nitro-1,3-dioxo-1,3-dihydro-isoindol-2-yl)-butanoic acid Prepared as described for Example 1, Part (b) by hydrolysis of the product of Part (a) above to give the title compound as a white solid; 55 mg.

MS; MH+ =497

$^1$H-NMR (CD$_3$OD) δ 8.8 (1H, d), 8.7 (1H, s), 7.2 (5H, m), 4.3 (2H, dd), 3.9–3.7 (4H, m), 2.2 (2H, m), 1.8 (1H, m), 1.6 (2H, m), 0.9 (6H, dd).

EXAMPLE 77

2-(R)-[1-(S)-(Benzylamino)carbonyl-3-methyl-butylamino]-4-(5-amino-1,3-dioxo-1,3-dihydro-isoindol-2-yl)-butanoic acid (a) 2-(R)-[1-(S)-(Benzylamino)carbonyl-3-methyl-butylamino]-4-(5-amino-1,3-dioxo-1,3-dihydro-isoindol-2-yl)-butanoic acid-1,1-dimethylethyl ester 2-[1-(benzylamino)carbonyl-3-methyl-butylamino]-4-(5-nitro-1,3-dioxo-1,3-dihydro-isoindol-2-yl)-butanoic acid-1,1-dimethylethyl ester, prepared as in Example 72 where the protecting group R$^p$, 1,1-dimethylethyl, was not removed following the condensation reaction seen in Scheme 2, was reduced by catalytic hydrogenation to give the title compound; 56 mg.

(b) 2-(R)-[1-(S)-(Benzylamino)carbonyl-3-methyl-butylamino]-4-(5-amino-1,3-dioxo-1,3-dihydro-isoindol-2-yl)-butanoic acid Prepared as described for Example 1, Part (b) by hydrolysis of the product of Part (a) above to give the title compound; 38 mg.

MS; MH+ =467.2294

$^1$H-NMR (CD$_3$OD) δ 7.4 (1H, d), 7.2 (5H, m), 6.9 (1H, s), 6.7 (1H, d), 4.3 (2H, dd), 3.9 (1H, t), 3.8–3.6 (4H, m), 2.1 (2H, m), 1.8–1.5 (3H, m), 0.9 (6H, dd).

EXAMPLE 78

2-(R)-[1-(S)-(Benzylamino)carbonyl-3-methyl-butylamino]-4-(5-methyl-1,3-dioxo-1,3-dihydro-isoindol-2-yl)-butanoic acid (a) 2-(R)-[1-(S)-(Benzylamino)carbonyl-3-methyl-butylamino]-4-(5-methyl-1,3-dioxo-1,3-dihydro-isoindol-2-yl)-butanoic acid-1,1-dimethylethyl ester Prepared as described for Example 70 using 5-methyl-1,3-dihydro-isoindole as a compound of Formula (V) to afford the title compound as a white solid;

(b) 2-(R)-[1-(S)-(Benzylamino)carbonyl-3-methyl-butylamino]-4-(5-methyl-1,3-dioxo-1,3-dihydro-isoindol-2-yl)-butanoic acid Prepared as described for Example 1, Part (b) by hydrolysis of the product of Part (a) above to give the title compound as a white powder

MS; MH+ =466

$^1$H-NMR (CD$_3$OD) δ7.65 (1H, d), 7.60 (1H, s), 7.55 (1H, d), 7.20 (5H, m), 4.33 (2H, m), 3.71 (4H, m), 2.42 (3H, s), 2.12 (2H, m), 1.76 (1H, m), 1.59 (2H, m), 0.86 (6H, dd).

EXAMPLE 79

2-(R)-[1-(S)-(Benzylamino)carbonyl-3-methyl-butylamino]-4-(5-methoxy-1,3-dioxo-1,3-dihydro-isoindol-2-yl)-butanoic acid (a) 2-(R)-[1-(S)-(Benzylamino)carbonyl-3-methyl-butylamino]-4-(5-methoxy-1,3-dioxo-1,3-dihydro-isoindol-2-yl)-butanoic acid-1,1-dimethylethyl ester Prepared as described for Example 70 using 1,3-dihydro-5-methoxy-1,3-dioxo-2H-isoindole as a compound of Formula (V) to afford the title compound as a white solid; 65 mg.

(b) 2-(R)-[1-(S)-(Benzylamino)carbonyl-3-methyl-butylamino]-4-(5-methoxy-1,3-dioxo-1,3-dihydro-isoindol-2-yl)-butanoic acid Prepared as described for Example 1, Part (b) by hydrolysis of the product of Part (a) above to give the title compound as a white powder; 25 mg.

MS; MH+ =482.2291

$^1$H-NMR (CD$_3$OD) δ 7.68 (1H, d), 7.28 (1H, s), 7.19 (6H, m), 4.23 (2H, q), 3.80 (3H, s), 3.70 (4H, m), 2.11 (2H, m), 1.71 (1H, m), 1.57 (2H, m), 0.86 (6H, dd).

EXAMPLE 80

2-(R)-[1-(S)-(Benzylamino)carbonyl-3-methyl-butylamino]-4-(5-benzyloxy-1,3-dioxo-1,3-dihydro-isoindol-2-yl)-butanoic acid (a) 2-(R)-[1-(S)-(Benzylamino)carbonyl-3-methyl-butylamino]-4-(5-benzyloxy-1,3-dioxo-1,3-dihydro-isoindol-2-yl)-butanoic acid-1,1-dimethylethyl ester Prepared as described for Example 70 using 1,3-dihydro-1,3-dioxophenylmethoxy-2H-isoindole as a compound of Formula (V) to afford the title compound as a white solid; 302 mg.

(b) 2-(R)-[1-(S)-(Benzylamino)carbonyl-3-methyl-butylamino]-4-(5-benzyloxy-1,3-dioxo-1,3-dihydro-isoindol-2-yl)-butanoic acid Prepared as described for Example 1, Part (b) by hydrolysis of the product of Part (a) above to give the title compound as a white powder; 18 mg.

MS; MH+ =558

$^1$H-NMR (CD$_3$OD) δ 7.68 (1H, d), 7.05–7.20 (12H, m), 5.18 (2H, s), 4.30 (2H, m), 3.71 (4H, m), 2.10 (2H, m), 1.75 (1H, m), 1.55 (2H, m), 0.93 (6H, dd).

EXAMPLE 81

2-(R)-[1-(S)-(Benzylamino)carbonyl-3-methyl-butylamino]-4-(5-phenyl-1,3-dioxo-1,3-dihydro-isoindol-2-yl)-butanoic acid (a) 2-(R)-[1-(S)-(Benzylamino)carbonyl-3-methyl-butylamino]-4-(5-phenyl-1,3-dioxo-1,3-dihydro-isoindol-2-yl)-butanoic acid-1,1-dimethylethyl ester Prepared as described for Example 70 using 1,3-dihydro-1,3dioxo-5-phenyl-2H-isoindole as a compound of Formula (V) to give the title compound as a white solid; 138 mg.

(b) 2-(R)-[1-(S)-(Benzylamino)carbonyl-3-methyl-butylamino]-4-(5-phenyl-1,3-dioxo-1,3-dihydro-isoindol-2-yl)-butanoic acid Prepared as described for Example 1, Part (b) by hydrolysis of the product of Part (a) above to give the title compound as a white solid; 52 mg.

MS; MH+ =528.2484

$^1$H-NMR (CD$_3$OD) δ 8.02 (2H, m), 7.98 (1H, d), 7.65 (2H, d), 7.44 (3H, m), 7.22 (5H, m), 4.30 (2H, m), 3.86 (2H, m), 3.78 (2H, m), 2,20 (2H, m), 1.77 (1H, m), 1.59 (2H, m), 0.88 (6H, dd).

EXAMPLE 82

2-(R)-[1-(S)-(Benzylamino)carbonyl-3-methylbutylamino]-4-(1,3-dioxo-1,3-dihydro-isoindol-2-yl)-butanoic acid (a) 2-(R)-[1-(S)-(Benzylamino)carbonyl-3-methylbutylamino]-4-(1,3-dioxo-1,3-dihydro-isoindol-2-yl)-butanoic acid-1,1-dimethylethyl ester Prepared as described for Example 70 using 1,3-dihydro-1,3-dioxo-2H-isoindole as a compound of Formula (V) to afford the title compound.

(b) 2-(R)-[1-(S)-(Benzylamino)carbonyl-3-methylbutylamino]-4-(1,3-dioxo-1,3-dihydro-isoindol-2-yl)-butanoic acid Prepared as described for Example 1, Part (b) by hydrolysis of the product of Part (a) above to give the title compound

MS; MH+ =452

$^1$H-NMR (CD$_3$OD) δ 7.8–7.6 (4H, m), 7.2 (5H, m), 4.4–4.2 (2H, dd), 3.8–3.6 (4H, m), 2.2 (2H, m), 1.7–1.6 (1H, m), 1.5 (2H, m), 0.9 (6H, dd).

EXAMPLE 83

2-(R)-[1-(S)-(Benzylamino)carbonyl-3-methylbutylamino]-4-(5-methanesulfonylamino-1,3-dioxo-1,3-dihydro-isoindol-2-yl)-butanoic acid (a) 2-(R)-[1-(S)-(Benzylamino)carbonyl-3-methylbutylamino]-4-(5-methanesulfonylamino-1,3-dioxo-1,3-dihydro-isoindol-2-yl)-butanoic acid-1,1-dimethylethyl ester 100 mg of 2-[1-(benzylamino)carbonyl-3-methylbutylamino]-4-(5-amino-1,3-dioxo-1,3-dihydro-isoindol-2-yl)-butanoic acid-1,1-dimethylethyl ester, prepared as in Example 73 where the protecting group R$^p$, 1,1-dimethylethyl, was not removed following the condensation reaction seen in Scheme 2, was added to 5 mL dichloromethane under nitrogen. The mixture was cooled to 0° C. and 0.1 mL of pyridine was added, followed by 0.014 mL methanesulfonyl chloride. The mixture was allowed to warm to room temperature and was stirred overnight. The solvent was removed by Evaporation and the residue was purified by reverse phase H.P.L.C. The solvent was removed by evaporation to give the title compound; 45 mg (b) 2-(R)-[1-(S)-(Benzylamino)carbonyl-3-methylbutylamino]-4-(5-methanesulfonylamino-1,3-dioxo-1,3-dihydro-isoindol-2-yl)-butanoic acid Prepared as described for Example 1, Part (b) by hydrolysis of the product of Part (a) above to give the title compound; 22 mg.

High Resolution MS; m/e Found: 545.2081

C$_{26}$H$_{32}$N$_4$O$_7$S Requires: 545.2070

$^1$H NMR (CD$_3$OD) δ 7.8 (1H, d), 7.6 (1H, s), 7.4 (1H, d), 7.2 (5H, m), 4.4–4.2 (2H, dd), 3.8–3.6 (3H, m), 3.0 (3H, s), 2.2 (2H, m), 1.7 (1H, m), 1.6–1.4 (2H, m), 0.9 (6H, dd).

EXAMPLE 84

2-(R)-[1-(S)-(Benzylamino)carbonyl-3-methylbutylamino]-4-(5-benzenesulfonylamino-1,3-dioxo-1,3-dihydro-isoindol-2-yl)-butanoic acid (a) 2-(R)-[1-(S)-(Benzylamino)carbonyl-3-methylbutylamino]-4-(5-benzenesulfonylamino-1,3-dihydro-isoindol-2-yl)-butanoic acid-1,1-dimethylethyl ester 58 mg of 2-[1-(benzylamino)carbonyl-3-methylbutylamino]-4-(5-amino-1,3-dioxo-1,3-dihydro-isoindol-2-yl)-butanoic acid-1,1-dimethylethyl ester, prepared as in Example 73 where the protecting group R$^p$, 1,1-dimethylethyl, was not removed following the condensation reaction seen in Scheme 2, was added to 4 mL dichloromethane under nitrogen. The mixture was cooled to 0° C. and 0.015 mL benzenesulfonyl chloride was added immediately followed by 0.1 mL pyridine. The mixture was allowed to warm to room temperature and was stirred for 18 h. The solvent was removed by evaporation and the residue was purified by reverse phase H.P.L.C. The solvent was removed by evaporation to afford the title compound; 31.8 mg (b) 2-(R)-[1-(S)-(Benzylamino)carbonyl-3-methylbutylamino]-4-(5-benzenesulfonylamino-1,3-dioxo-1,3-dihydro-isoindol-2-yl)-butanoic acid Prepared as described for Example 1, Part (b) by hydrolysis of the product of Part (a) above to give the title compound; 20.4 mg.

$^1$H-NMR (CD$_3$OD) δ 7.8 (2H, d), 7.6 (1H, d), 7.5–7.3 (5H, m), 7.2 (5H, m), 4.3 (2H, dd), 3.9 (2H, m), 3.8–3.6 (2H, m), 2.1 (2H, m), 1.8 (1H, m), 1.6–1.4 (2H, m), 0.9 (6H, dd).

EXAMPLE 85

2-(R)-[1-(S)-(Benzylamino)carbonyl-3-methylbutylamino]-4-(5-hydroxy-1,3-dioxo-1,3-dihydro-isoindol-2-yl)-butanoic acid (a) 2-(R)-[1-(S)-(Benzylamino)carbonyl-3-methylbutylamino]-4-(5-hydroxy-1,3-dioxo-1,3-dihydro-isoindol-2-yl)-butanoic acid-1,1-dimethylethyl ester 100 mg of 2-[1-(benzylamino)carbonyl-3-methylbutylamino]-4-(5-benzyloxy-1,3-dioxo-1,3-dihydro-isoindol-2-yl)-butanoic acid-1,1-dimethylethyl ester, prepared as in Example 76 where the protecting group Rp, 1,1-dimethylethyl, was not removed following the condensation reaction seen in Scheme 2, was added to 10 mg of 10% Palladium on carbon in 2.5 mL absolute ethanol under 1 atmosphere of hydrogen. The mixture was stirred for 15 h and filtered through celite. The solvent was removed by evaporation and the residue was w ashed with hexane. The solvent was removed by evaporation yielding 66 mg of a white solid (b) 2-(R)-[1-(S)-(Benzylamino)carbonyl-3-methylbutylamino]-4-(5-hydroxy-1,3-dioxo-1,3-dihydro-isoindol-2-yl)-butanoic acid Prepared as described for Example 1, Part (b) by hydrolysis of the product of Part (a) above to give the title compound; 35 mg.

High Resolution MS; m/e Found: 468.2131

C$_{25}$H$_{29}$N$_3$O$_6$ Requires: 468.2135

$^1$H-NMR (CD$_3$OD) δ 7.59 (IH, d), 7.18 (6H, m), 7.00 (IH, d), 4.31 (2H, m), 3.70 (4H, m), 2.06 (2H, m), 1.74 (IH, m), 1.59 (2H, m), 0.88 (6H, dd).

EXAMPLE 86

2-(R)-[[3-Methyl-1-(S)-[[(pyridin-3-ylmethyl)amino]carbonyl]butyl]amino]-4-(1,3,5,7-tetraoxo-3,5,6-tetrahydro-1H-pyrolo[3,4-f]isoindol-2-yl) butanoic acid a)2-(R)-[[3-Methyl-1-(S)-[[(pyridin-3-ylmethyl)amino]carbonyl]butyl]amino]-4-(1,3,5,7-tetraoxo-3,5,6-tetrahydro-1H-pyrolo[3,4-f]isoindol-2-yl)butanoic acid-1,1-dimethylethyl ester 0.3827 g of triphenylphosphine was added to 0.5034 g of 2-(R)-[1-(S)-[(pyridin-3-ylmethyl)amino]carbonyl-3-methyl-butylamino]-4-hydroxy-butanoic acid-1,1-dimethylethyl ester, prepared as in Example P, in 29 mL of THF at 0° C. 0.3153 g of 1,3,5,7-tetraoxo-2H, 6H-benzo(1,2-c: 4,5-c')dipyrrole was added, followed by 0.2541 g diethylazodicarboxylate. The mixture was allowed to stir overnight at 23° C. The solvent was removed by evaporation and the residue purified by silica gel chromatography to give the title compound as a white solid; 81 mg.

b)2-(R)-[[3-Methyl-1-(S)-[[(pyridin-3-ylmethyl)amino]carbonyl]butyl]amino]-4-(1,3,5,7-tetraoxo-3,5,6-tetrahydro-1H-pyrolo[3,4-f]isoindol-2-yl)butanoic acid Prepared as described for Example 1, Part (b) by hydrolysis of the product of Part (a) above to give the title compound; 40 mg.

[α]D 0.42 (c=0.240, MeOH)
MS; MH+ =522
$^1$H-NMR (CD$_3$OD) δ 8.86 (1H, s0<8.77 (1H, d, J=4 Hz), 8.53 (1H, d, J=7 Hz), 8.20 (2H, s), 7.99–8.63 (1H, m), 4.64 (2H, ABq), 3.85–4.00 (4H, m), 2.31 (2H, q, J=6 Hz), 1.50–1.80 (3H, m), 0.98 (3H, d, J=7 Hz), 0.96 (3H, d, J=7 Hz).

What is claimed is:

1. Aminobutanoic acids of the following formula (I):

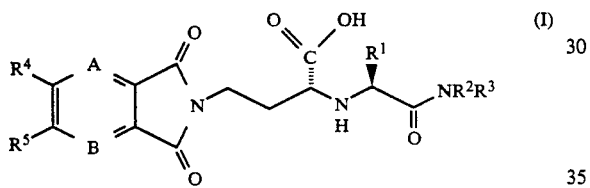

wherein:

A and B are independently CR where
R is hydrogen, halogen, C$_{1-4}$alkyl, C$_{1-4}$alkoxy;
R$^1$ is C$_{3-6}$alkyl or C$_{1-4}$alkylthioC$_{1-4}$alkyl;
R$^2$ is hydrogen, C$_{1-4}$alkyl or hydroxyC$_{1-4}$alkyl;
R$^3$ is C$_{1-4}$alkyl, C$_{1-4}$alkoxy, C$_{1-4}$alkylamino, tris(hydroxymethyl)methyl, aryl, substituted aryl, arylsulfonyl, (substituted aryl)sulfonyl, benzylsulfonyl, heteroarylsulfonyl, (substituted heteroaryl)sulfonyl, heteroarylcarbonyl, (substituted heteroaryl)carbonyl or —(CH$_2$)$_n$CHR$^6$R$^7$ where
n is the integer 0, 1, 2, 3 or 4;
R$^6$ is hydrogen, C$_{1-4}$alkyl, C$_{1-4}$alkoxy, C$_{1-4}$alkylamino;
R$^7$ is hydroxy, mono- or di-(C$_{1-4}$alkyl)amino, aryl, substituted aryl, heteroaryl, substituted heteroaryl, a saturated 5, 6, or 7 membered ring optionally interrupted by 1, 2, 3, or 4N, S, or O heteroatoms, sulfonyl or carbonyl, with the proviso that any two O or S atoms are not bonded to each other, such saturated ring optionally mono-, di-, tri-, or tetrasubstituted independently with C$_{1-4}$alkyl, hydroxy, oxo, nitro, hydroxyC$_{1-4}$alkyl, aryl, substituted aryl, aminocarbonyl or acetylamino substituents; or
CHR$^6$R$^7$ together form a saturated 5 to 13 membered ring optionally interrupted by 1, 2, 3, or 4N, S, or O heteroatoms, sulfonyl or carbonyl, with the proviso that any two O or S atoms are not bonded to each other, such saturated ring optionally mono-, di-, or tri, or tetrasubstituted independently with C$_{1-4}$alkyl, hydroxy, oxo, nitro, hydroxyC$_{1-4}$alkyl, aryl, substituted aryl, aminocarbonyl or acetylamino substituents, a saturated 6, 7 or 8 membered bicyclic ring optionally interrupted by 1, 2, 3, or 4N, S, or O heteroatoms, with the proviso that any two O or S atoms are not bonded to each other, a 9 or 10 membered bicyclic ring which is partially aromatic, such bicyclic ring optionally mono-, di-, or trisubstituted independently with C$_{1-4}$alkyl, halogen, amino, hydroxy, (C$_{1-2}$alkylsulfonyl)amino, nitro, aminosulfonyl, carboxy, COO(C$_{1-4}$alkyl), trifluoromethyl, mono- or disubstituted (C$_{1-2}$alkyl)amino or trifluoromethylsulfonylamino substituents, a 9 or 10 membered heterobicyclic ring which is partially aromatic, interrupted by 1, 2, 3, or 4 N, S, O heteroatoms, carbonyl or sulfonyl, with the proviso that any two O or S atoms are not bonded to each other, such heterobicyclic ring optionally mono-, di-, or trisubstituted independently with C$_{1-4}$alkyl, halogen, amino, hydroxy, (C$_{1-2}$alkylsulfonyl)amino, nitro, aminosulfonyl, carboxy, COO(C$_{1-4}$alkyl), trifluoromethyl, mono- or disubstituted (C$_{1-2}$alkyl)amino or trifluoromethylsulfonylamino substituents; or
NR$^2$R$^3$ together form a saturated 5, 6, or 7 membered ring interrupted by 1, 2, 3, or 4 N, S, or O heteroatoms, sulfonyl or carbonyl, with the proviso that any two O or S atoms are not bonded to each other, such saturated ring optionally mono-, di-, or trisubstituted independently with C$_{1-4}$alkyl, hydroxy, nitro, aryl, substituted aryl, 2,3-dihydroxypropyl, heteroaryl, substituted heteroaryl, —CH$_2$COO(C$_{1-4}$alkyl), COO(C$_{1-4}$alkyl), amino, carboxy, acetylamino, oxo, aminosulfonyl, aminocarbonyl, trifluoromethyl, trifluoromethylsulfonylamino, mono- or di-(C$_{1-4}$alkyl)amino, halogen or (C$_{1-4}$alkylsulfonyl)amino substituents, an 9 or 10 membered heterobicyclic ring which is partially aromatic, interrupted by 1, 2, 3, or 4N heteroatoms, such heterobicyclic ring optionally mono-, di-, or trisubstituted independently with oxo, aryl, substituted aryl, heteroaryl, substituted heteroaryl, C$_{1-4}$alkyl, halogen, amino, hydroxy, acetylamino, (C$_{1-4}$alkylsulfonyl)amino, nitro, aminosulfonyl, aminocarbonyl, carboxy, COO(C$_{1-4}$alkyl), trifluoromethyl, mono- or di-substituted (C$_{1-4}$alkyl)amino, 2,3,-dihydroxypropyl or trifluoromethylsulfonylamino substituents;

R$^4$ is hydrogen, hydroxy, C$_{1-6}$alkyl, C$_{1-6}$alkoxy or halogen;
R$^5$ is hydrogen, C$_{1-6}$alkyl, amino, aminoC$_{1-4}$alkyl, mono-or di-(C$_{1-4}$alkyl)amino, mono- or di-(C$_{1-4}$alkyl)aminoC$_{1-4}$alkyl, acetylamino, aryl, substituted aryl, (aryl)sulfonylamino, nitro, (C$_{1-4}$alkyl)sulfonylamino, hydroxy, C$_{1-6}$alkoxy, halogen, morpholino, piperazinyl, piperidinyl, (aryl)C$_{1-4}$alkoxy, (substituted aryl)C$_{1-4}$alkoxy, aryloxy, (substituted aryl)oxy, (aryl)C$_{1-4}$alkyl, (substituted aryl)C$_{1-4}$alkyl, heteroaryl, substituted heteroaryl, (heteroaryl)C$_{1-4}$alkyl, (substituted heteroaryl)C$_{1-4}$alkyl, (heteroaryl)C$_{1-4}$alkoxy, (substituted heteroaryl)C$_{1-4}$alkoxy, heteroaryloxy or (substituted heteroaryl)oxy; or R⁴R⁵ together form an aryl, substituted aryl or a saturated 5 or 6 membered ring optionally interrupted by 1, 2, or 3N, S, or O heteroatoms, with the proviso that any two O or S atoms are not bonded to each other, such saturated ring optionally mono-, di-, or trisubstituted independently with from $C_{1-4}$alkyl, oxo, nitro or aminosulfonyl substituents;

wherein substituted aryl is defined as an aryl mono-, di-, or trisubstituted independently with $C_{1-4}$alkyl, halogen, amino, hydroxy, acetylamino, ($C_{1-4}$alkylsulfonyl)amino, nitro, aminosulfonyl, aminocarbonyl, carboxy, COO($C_{1-4}$alkyl), trifluoromethyl, mono- or disubstituted ($C_{1-4}$alkyl)amino, aryl, 2,3,-dihydroxypropyl or trifluoromethylsulfonylamino substituents;

wherein heteroaryl is defined as a 5 or 6 membered aromatic ring optionally interrupted by 1, 2, 3 or 4 N, S, or O heteroatoms, with the proviso that any two O or S atoms are not bonded to each other;

wherein substituted heteroaryl is defined as heteroaryl mono-, di-, or trisubstituted independently with $C_{1-4}$alkyl, halogen, amino, hydroxy, acetylamino, ($C_{1-4}$alkylsulfonyl)amino, nitro, aminosulfonyl, aminocarbonyl, carboxy, COO($C_{1-4}$alkyl), trifluoromethyl, mono- or disubstituted ($C_{1-4}$alkyl)amino, aryl, 2,3,-dihydroxypropyl, or trifluoromethylsulfonylamino substituents; or a pharmaceutically acceptable acid-addition or organic base-addition salt thereof.

2. The aminobutanoic acid of claim 1, wherein:

A and B are independently N or CR where

R is hydrogen, halogen, $C_{1-3}$alkyl or $C_{1-3}$alkoxy;

$R^1$ is $C_{3-6}$alkyl;

$R^2$ is hydrogen, methyl, ethyl or hydroxy$C_{1-3}$alkyl;

$R^3$ is $C_{1-3}$alkyl, $C_{1-4}$ alkoxy, $C_{1-3}$alkylamino, tris(hydroxymethyl)methyl, aryl, such aryl optionally mono-, di-, or trisubstituted independently with amino, aminosulfonyl or trifluoromethylsulfonylamino substituents, phenylsulfonyl, benzylsulfonyl, pyridinylsulfonyl, pyridinylcarbonyl, or —(CH₂)$_n$CHR⁶R⁷ where n is the integer 0, 1, 2 or 3;

$R^6$ is hydrogen or $C_{1-3}$alkyl;

$R^7$ is mono- or disubstituted $C_{1-3}$alkylamino, aryl, such aryl optionally mono-, di-, or trisubstituted independently with $C_{1-3}$alkyl, halogen, amino, hydroxy, ($C_{1-2}$alkylsulfonyl)amino, nitro, aminosulfonyl, carboxy, COO(C1-4alkyl), trifluoromethyl, mono- or disubstituted ($C_{1-2}$alkyl)amino, or trifluoromethylsulfonylamino substituents, heteroaryl, such heteroaryl optionally mono-, di-, or trisubstituted independently with $C_{1-3}$alkyl, amino or hydroxy substituents, a saturated 5, 6, or 7 membered ring optionally interrupted by 1 or 2N, S, or O heteroatoms, sulfonyl or carbonyl, with the proviso that any two O or S atoms are not bonded to each other, such saturated ring optionally mono-, di-, tri- or tetrasubstituted independently with $C_{1-3}$alkyl, hydroxy, hyroxy$C_{1-3}$alkyl, aminocarbonyl, acetylamino, oxo, nitro or phenyl substituents; or CHR⁶R⁷ together form a saturated 5, 6, 8, 10, or 13 membered ring optionally interrupted by one to two N, S, O heteroatoms, or sulfonyl, with the proviso that any two O or S atoms are not bonded to each other, such saturated ring optionally mono-, di-, tri- or tetrasubstituted independently with $C_{1-3}$alkyl, hydroxy, hydroxy$C_{1-3}$alkyl, oxo, aminocarbonyl or acetylamino substituents, saturated 6, 7 or 8 membered bicyclic ring optionally interrupted by 1 to 2N heteroatoms, 9 or 10 membered bicyclic ring which is partially aromatic, such bicyclic ring optionally mono-, di, or trisubstituted independently with $C_{1-3}$alkyl, halogen, amino, hydroxy, ($C_{1-2}$alkylsulfonyl)amino, nitro, aminosulfonyl, carboxy, COO(C1-4alkyl), trifluoromethyl, mono- or disubstituted ($C_{1-2}$alkyl)amino or trifluoromethylsulfonylamino substituents; or NR²R³ together form a saturated 5 or 6 membered ring optionally interrupted by one N, S, or O heteroatom, or sulfonyl, such saturated ring optionally mono-, di-, or trisubstituted independently with $C_{1-3}$alkyl, oxo, phenyl, 2,3-dihydroxypropyl, pyridinyl, ethoxycarbonyl or ethoxycarbonylmethyl substituents, 10 membered bicyclic ring which is partially aromatic;

$R^4$ is hydrogen $C_{1-3}$alkyl, $C_{1-3}$alkoxy, halogen or hydroxy;

$R^5$ is amino, nitro, ($C_{1-3}$alkylsulfonyl)amino, hydrogen, $C_{1-3}$alkyl, hydroxy, methoxy, propoxy, benzoxy, bromine, phenyl or (phenyl)sulfonylamino; or R⁴R⁵ together form a benzene ring or a saturated 5 or 6 membered ring optionally interrupted by 1N heteroatom, such saturated ring optionally bearing 1 to 2 oxo substituents.

3. The aminobutanoic acid of claim 1, wherein:

$R^1$ is isobutyl.

4. The aminobutanoic acid of claim 1, wherein:

$R^7$ is phenyl optionally mono-, di-, or trisubstituted independently with $C_{1-3}$alkyl, halogen, amino, hydroxy, ($C_{1-2}$alkylsulfonyl)amino, nitro, aminosulfonyl, carboxy, COO(C1-4alkyl), trifluoromethyl, mono- or disubstituted ($C_{1-2}$alkyl)amino or trifluoromethylsulfonylamino substituents.

5. The aminobutanoic acid of claim 1, wherein:

$R^7$ is a 5 or 6 membered heteroaryl ring interrupted by 1, 2, 3, or 4N, or one O heteroatom, such heteroaryl optionally mono- or disubstituted independently with $C_{1-3}$alkyl, amino or hydroxy substituents.

6. The aminobutanoic acid of claim 1, wherein:

CHR⁶R⁷ together form a 9 or 10 membered bicyclic ring which is partially aromatic, such bicyclic ring optionally mono-, di, or trisubstituted independently with $C_{1-3}$alkyl, halogen, amino, hydroxy, ($C_{1-2}$alkylsulfonyl)amino, nitro, aminosulfonyl, carboxy, COO(C1-4alkyl), trifluoromethyl, mono- or disubstituted ($C_{1-2}$alkyl)amino or trifluoromethylsulfonylamino substituents, a 9 or 10 membered heterobicyclic ring which is partially aromatic, such heterobicyclic ring optionally interrupted by 1 or 2N, S, O heteroatoms, carbonyl, or sulfonyl, such heterobicyclic ring optionally mono-, di-, or trisubstituted independently with $C_{1-3}$alkyl, halogen, amino, hydroxy, ($C_{1-2}$alkylsulfonyl)amino, nitro, aminosulfonyl, carboxy, COO(C1-4alkyl), trifluoromethyl, mono- or disubstituted ($C_{1-2}$alkyl)amino or trifluoromethylsulfonylamino substituents.

7. The aminobutanoic acid of claim 1, wherein:

$R^1$ is isobutyl;

R² is hydrogen;
n is 0;
R⁶ is hydrogen or methyl;
R⁷ is phenyl optionally mono- or disubstituted independently with fluoro, carboxy, COO(C1-4alkyl) or aminosulfonyl substituents;
R⁴R⁵ together form a benzene ring.

8. The aminobutanoic acid of claim 1, wherein:
R¹ is isobutyl;
R² is hydrogen;
n is 0;
R⁶ is hydrogen or methyl;
R⁷ is monofluorophenyl or difluorophenyl;
R⁴R⁵ together form a benzene ring.

9. The aminobutanoic acid of claim 1, wherein:
R¹ is isobutyl;
R² is hydrogen;
R²R³ together form a 6 membered saturated ring optionally interrupted by one N heteroatom, such ring optionally mono- or disubstituted independently with methyl, ethoxycarbonyl, ethoxycarbonylmethyl, 2,3-dihydroxypropyl or pyridinyl substituents;
R⁴R⁵ together form a benzene ring.

10. The aminobutanoic acid of claim 1, wherein:
R¹ is isobutyl;
R² is hydrogen;
n is 1;
R⁶ is hydrogen;
R⁷ is tetrazole optionally mono- or disubstituted independently with C₁-₃alkyl substituents;
R⁴R⁵ together form a benzene ring.

11. The aminobutanoic acid of claim 1, wherein:
R¹ is isobutyl;
R² is hydrogen or methyl;
n is 0 or 1;
R⁶ is hydrogen;
R⁷ is phenyl;
R⁴R⁵ together form a benzene ring.

12. The aminobutanoic acid of claim 1, wherein:
R¹ is isobutyl;
R² is hydrogen;
n is 0;
R⁶R⁷ together form a 13 membered saturated ring interrupted by 1 or 2N heteroatoms, such ring optionally mono-, di-, or trisubstituted independently with oxo or methyl substituents;
R⁴R⁵ together form a benzene ring.

13. The aminobutanoic acid of claim 1, wherein:
R¹ is isobutyl;
R² is hydrogen;
n is 0;
R⁶ is hydrogen;
R⁷ is phenyl;
R⁴ is hydrogen;
R⁵ is hydrogen or C₁-₆ alkoxy.

14. The aminobutanoic acid of claim 1, wherein:
R¹ is isobutyl;
R² is methyl;
n is 0;
R⁶ is hydrogen;
R⁷ is phenyl;
R⁴R⁵ together form a benzene ring.

15. The aminobutanoic acid of claim 1, wherein the aminobutanoic acid is selected from the group consisting of:

4-(1,3-Dihydro-1,3-dioxo-2H-benz[f]isoindol-2-yl)-2-(R)-[[3-methyl-1-(S)-[[(2-morpholin-4-ylethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[methylamino]carbonyl]butyl]amino]-butanoic acid 4-(1,3-Dihydro-1,3-dioxo-2H-benz[f]isoindol-2-yl)-2-(R)-[[3-methyl-1-(S)-[[(1H-imidazol-2-ylmethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(1H-tetrazol-5-ylmethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[[2-(phenyl)ethyl]amino]carbonyl]butyl]amino]-butanoic acid 4-(1,3-Dihydro-1,3-dioxo-2H-benz[f]isoindol-2-yl)-2-(R)-[[3-methyl-1-(S)-[[(pyridin-3-ylmethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(2-methyl-2H-tetrazo-5-ylmethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(4-hydroxy-2-methyl-pyrimidin-5-ylmethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[[2-(2-pyridin-3-yl)ethyl]amino]carbonyl]butyl]amino]-butanoic acid 4-(1,3-Dihydro-1,3-dioxo-2H-benz[f]isoindol-2-yl)-2-(R)-[[3-methyl-1-(S)-[[1-(1H-tetrazol-5-yl)ethyl]amino]carbonyl]butyl]amino]-butanoic acid 4-(1,3-Dihydro-1,3-dioxo-2H-benz[f]isoindol-2-yl)-2-(R)-[[3-methyl-1-(S)-[[(5-amino-4H-[1,2,4]-triazol-3-ylmethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[[1-(6-oxo-1,6-dihydro-pyridazin-3yl)ethyl]amino]carbonyl]butyl]amino]-butanoic acid 4-(1,3-Dihydro-1,3-dioxo-2H-benz[f]isoindol-2-yl)-2-(R)-[[3-methyl-1-(S)-[[(phenyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(benzyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(pyridin-4-ylmethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[[2-(1H-imidazol-4-yl)ethyl]amino]carbonyl]butyl]amino]-butanoic acid 4-(1,3-Dihydro-1,3-dioxo-2H-benz[f]isoindol-2-yl)-2-(R)-[[3-methyl-1-(S)-[[(pyridin-2-ylmethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(4-sulfamoyl-phenyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(3-sulfamoyl-phenyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(4-dimethylamino-benzyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[[1-(S)-phenyl-ethyl]amino]carbonyl]butyl]amino]-butanoic acid 4-(1,3-Dihydro-1,3-dioxo-2H-benz[f]isoindol-2-yl)-2-(R)-[[3-methyl-1-(S)-[[(1,1-dioxo-tetrahydro-thiophen-3-yl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(4-sulfamoyl-benzyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[[1-(R)-phenyl-ethyl]amino]carbonyl]butyl]amino]-butanoic acid 4-(1,3-Dihydro-1,3-dioxo-2H-benz[f]isoindol-2-yl)-2-(R)-[[3-methyl-1-(S)-[[(3-fluorobenzyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(furan-2-ylmethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(1-methyl-1H-tetrazol-5-ylmethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(1,2,3,4-tetrahydro-naphthalen-1-yl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(2,4-difluoro-benzyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(3-nitrobenzyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(4-nitrobenzyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(4-methanesulfonylamino-benzyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(3-methanesulfonylamino-benzyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(3,4-difluoro-benzyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(3-trifluoromethyl-benzyl)amino]carbonyl]butyl]amino]-butanoic acid 4-[2-(S)-[1-(R)-Carboxy-3-(1,3-dioxo1,3-dihydro-benzo[f]isoindol-2-yl)-propylamino]-4-methyl-pentanoylamino-methyl)-benzoic acid 4-(1,3-Dihydro-1,3-dioxo-2H-benz[f]isoindol-2-yl)-2-(R)-[[3-methyl-1-(S)-[[(2-hydroxy-1,1-bis-hydroxymethyl-ethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(3,5-difluoro-benzyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[benzylmethyl-amino]carbonyl]butyl]amino]-butanoic acid 4-(1,3-Dihydro-1,3-dioxo-2H-benz[f]isoindol-2-yl)-2-(R)-[[3-methyl-1-(S)-[[(2-dimethylaminoethyl)-methyl-amino]carbonyl]butyl]amino]-butanoic acid 4-(1,3-Dihydro-1,3-dioxo-2H-benz[f]isoindol-2-yl)-2-(R)-[[3-methyl-1-(S)-[[(1-azabicyclo[2.2.2]-oct-3(R)-amino]carbonyl]butyl]-butanoic acid 4-(1,3-Dihydro-1,3-dioxo-2H-benz[f]isoindol-2-yl)-2-(R)-[[3-methyl-1-(S)-[[(1-azabicyclo[2.2.2]oct-3-(S)-yl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(3-(R)-4-(S)-5-(R)-6-tetrahydrox-tetrahydra-pyran-2-(R)-ylmethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(N,N'-dimethyl-hydrazino)-carbonyl]butyl]amino]-butanoic acid 4-(1,3-Dihydro-1,3-dioxo-2H-benz[f]isoindol-2-yl)-2-(R)-[[3-methyl-1-(S)-[[(methylmethoxy)amino]carbonyl]butyl]amino]-butanoic acid 4-(1,3-Dihydro-1,3-dioxo-2H-benz[f]isoindol-2-yl)-2-(R)-[[3-methyl-1-(S)-[[(dimethyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(2-oxo-tetrahydro-thiophen-3-(R)-yl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(2-oxotetrahydro-thiophen-3-(S)-yl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(3-(R)-acetylamino-4-(S)-5-(S)-dihydroxy-6-(R)-hydroxymethyl-tetrahydro-pyran-2-yl)amino]carbonyl]butyl]amino]-butanoic acid 4-(1,3-Dihydro-1,3-dioxo-2H-benz[f]isoindol-2-yl)-2-(R)-[[3-methyl-1-(S)-[[[benzyl(2-hydroxyethyl)-]amino]carbonyl]butyl]amino]-butanoic acid 4-(1,3-Dihydro-1,3-dioxo-2H-benz[f]isoindol-2-yl)-2-(R)-[[3-methyl-1-(S)-[3,4-dihydro-1H-isoquinoline-2-carbonyl]butyl]amino]-butanoic acid 4-(1,3-Dihydro-1,3-dioxo-2H-benz[f]isoindol-2-yl)-2-(R)-[[3-methyl-1-(S)-[4-methylpiperazine-1-carbonyl]butyl]amino]-butanoic acid 4-(1,3-Dihydro-1,3-dioxo-2H-benz[f]isoindol-2-yl)-2-(R)-[[3-methyl-1-(S)-[1-oxo-[1,4]thiazinane-4-carbonyl]butyl]amino]-butanoic acid 4-(1,3-Dihydro-1,3-dioxo-2H-benz[f]isoindol-2-yl)-2-(R)-[[3-methyl-1-(S)-[morpholine-4-carbonyl]butyl]amino]-butanoic acid 4-(1,3-Dihydro-1,3-dioxo-2H-benz[f]isoindol-2-yl)-2-(R)-[[3-methyl-1-(S)-[4-(2-3-dihydroxy-propyl)-piperazine-1-carbonyl]butyl]amino]-butanoic acid 4-(1,3-Dihydro-1,3-dioxo-2H-benz[f]isoindol-2-yl)-2-(R)-[[3-methyl-1-(S)-[3,4,5,6-tetrahydro-H-[2,3]bipyridinyl-1]carbonyl]butyl]amino]-butanoic acid 4-(1,3-Dihydro-1,3-dioxo-2H-benz[f]isoindol-2-yl)-2-(R)-[[3-methyl-1-(S)-[[(1-methyl-8-oxo-1,7-diazacyclotridec-9-yl)amino]carbonyl]butyl]amino]-butanoic acid 4-(1,3-Dihydro-1,3-dioxo-2H-benz[f]isoindol-2-yl)-2-(R)-[[3-methyl-1-(S)-[[methyl-1-methyl-piperidin-4-yl)amino]carbonyl]butyl]amino]-butanoic acid 4-(1,3-Dihydro-1,3-dioxo-2H-benz[f]isoindol-2-yl)-2-(R)-[[3-methyl-1-(S)-[[(4-hydroxy-1,1-dioxo-tetrahydro-thiophen-3-yl)amino]carbonyl]butyl]amino]-butanoic acid 4-(1,3-Dihydro-1,3-dioxo-2H-benz[f]isoindol-2-yl)-2-(R)-[[3-methyl-1-(S)-(4-ethoxycarbonylmethyl-piperazine-1-carbonyl)butyl]amino]-butanoic acid 4-(1,3-Dihydro-1,3-dioxo-2H-benz[f]isoindol-2-yl)-2-(R)-[[3-methyl-1-(S)-[[(1,1-dioxo-tetrahydro-thiophen-3-yl)-methyl-amino]carbonyl]butyl]amino]-butanoic acid 4-(1,3-Dihydro-1,3-dioxo-2H-benz[f]isoindol-2-yl)-2-(R)-[[3-methyl-1-(S)-[2-(R)-(pyridin-3-yl)-pyrrolidinecarbonyl]butyl]amino]-butanoic acid 4-(1,3-Dihydro-1,3-dioxo-2H-benz[f]isoindol-2-yl)-2-(R)-[[3-methyl-1-(S)-[2-(S)-(pyridin-3-yl)-pyrrolidinecarbonyl]butyl]amino]-butanoic acid 4-(1,3-Dihydro-1,3-dioxo-2H-benz[f]isoindol-2-yl)-2-(R)-[[3-methyl-1-(S)-[3-oxo-2-(R)-phenyl-piperazine-1-carbonyl]butyl]amino]-butanoic acid 4-(1,3-Dihydro-1,3-dioxo-2H-benz[f]isoindol-2-yl)-2-(R)-[[3-methyl-1-(S)-[3oxo-2-(S)-phenyl-piperazine-1-carbonyl]butyl]amino]-butanoic acid 4-(1,3-Dihydro-1,3-dioxo-2H-benz[f]isoindol-2-yl)-2-(R)-[[3-methyl-1-(S)-[(pyridine-3-carbonyl-hydrazino)carbonyl]butyl]amino]-butanoic acid 4-(1,3-Dihydro-1,3-dioxo-2H-benz[f]isoindol-2-yl)2-(R)-[[3-methyl-1-(S)-[[(benzenesulfonyl)amino]carbonyl]butyl]amino]-butanoic acid 4-(1,3-Dihydro-1,3-dioxo-2H-benz[f]isoindol-2-(R)-[[3-methyl-1-(S)-[[(3-aminobenzyl)amino]carbonyl]butyl]amino]-butanoic acid 4-(1,3-Dihydro-1,3-dioxo-2H-benz[f]isoindol-2-yl)-2-(R)-[[3-methyl-1-(S)-[[[4(trifluoro-methanesulfonylamino)benzyl]amino]carbonyl]butyl]amino]-butanoic acid 4-(1,3-Dihydro-1,3-dioxo-2H-benz[f]isoindol-2-yl)-2-(R)-[[3-methyl-1-(S)-[[[2-hydroxy-(R)-bicyclo[4.3.0-]nona-3,6(1)-diene]amino]carbonyl]butyl]amino]-butanoic acid 4-(1,3-Dihydro-1,3-dioxo-2H-benz[f]isoindol-2-yl)-2-(R)-[[3-methyl-1-(S)-[[[2-hydroxy-(S)-bicyclo[4.3.0-]nona-3.6(1)-diene]amino]carbonyl]butyl]amino]-butanoic acid 4-(1,3-Dihydro-1,3-dioxo-2H-benz[f]isoindol-2-yl)-2-(R)-[[3-methyl-1-(S)-[(N-methyl-pyrrolidine)-methyl-amino]carbonyl]butyl]amino]-butanoic acid 4-(1,3-Dihydro-1,3-dioxo-2H-benz[f]isoindol-2-yl)-2-(R)-[[3-methyl-1-(S)-[(N-ethoxycarbonylmethyl-piperazine)-1-carbonyl]butyl]amino]-butanoic acid 2-(R)-[1-(S)-(Benzylamino)carbonyl-3-methyl-butylamino]-4-(5-bromo-1,3-dioxo-1,3-dihydro-isoindol-2-yl)-butanoic acid 2-(R)-[1-(S)-(Benzylamino)carbonyl-3-methyl-butylamino]-4-(5-propoxy-1,3-dioxo-1,3-dihydro-isoindol-2-yl)-butanoic acid 2-(R)-[1-(S)-(Benzylamino)carbonyl-3-methyl-butylamino]-4-(5-nitro-1,3-dioxo-1,3-dihydro-isoindol-2-yl)-butanoic acid 2-(R)-[1-(S)-(Benzylamino)carbonyl-3-methyl-butylamino]-4-(5-amino-1,3-dioxo-1,3-dihydro-isoindol-2-yl)-butanoic acid 2-(R)-[1-(S)-(Benzylamino)carbonyl-3-methyl-butylamino]-4-(5-methyl-1,3-dioxo-1,3-dihydro-isoindol-2-yl)-butanoic acid 2-(R)-[1-(S)-(Benzylamino)carbonyl-3-methyl-butylamino]-4-(5-methoxy-1,3-dioxo-1,3-dihydro-isoindol-2-yl)-butanoic acid 2-(R)-[1-(S)-(Benzylamino)carbonyl-3-methyl-butylamino]-4-(5-benzyloxy-1,3-dioxo-1,3-dihydro-isoindol-2-yl)-butanoic acid 2-(R)-[1-(S)-(Benzylamino)carbonyl-3-methyl-butylamino]-4-(5-phenyl-1,3-dioxo-1,3-dihydro-isoindol-2-yl)-butanoic acid 2-(R)-[1-(S)-(Benzylamino)carbonyl-3-methyl-butylamino]-4-(1,3-dioxo-1,3-dihydro-isoindol-2-yl)-butanoic acid 2-(R)-[1-(S)-(Benzylamino)carbonyl-3-methyl-butylamino]-4-(5-methanesulfonylamino-1,3-dioxo-1,3-dihydro-isoindol-2-yl)-butanoic acid 2-(R)-[1-(S)-(Benzylamino)carbonyl-3-methyl-butylamino]-4-(5-benzenesulfonylamino-1,3-dioxo-1,3-dihydro-isoindol-2-yl)-butanoic acid 2-(R)-[1-(S)-(benzylamino)carbonyl-3-methyl-butylamino]-4-(5-hydroxy-1,3-dioxo-1,3-dihydro-isoindol-2-yl)-butanoic acid 2-(R)-[[3-Methyl-1-(S)-[[(pyridin-3-ylmethyl)amino]-carbonyl]butyl]amino]-4-(1,3,5,7-tetraoxo-3,5,6-tetrahydro-1H-pyrolo[3,4-f]isoindol-2-yl)butanoic acid.

16. A pharmaceutical composition comprising an appropriate dosage of the aminobutanoic acid of claim 1 and a pharmaceutically acceptable diluent or carrier.

17. A method for the treatment of rheumatoid arthritis which comprises administering to a patient in need of such an appropriate dosage of the pharmaceutical composition of claim 16.

18. A method for the treatment of tumour metastasis and angiogenesis which comprises administering to a patient in need of such an appropriate dosage of the pharmaceutical composition of claim 16.

19. A method for the treatment of demyelinating diseases of the nervous system which comprises administering to a patient in need of such an appropriate dosage of the pharmaceutical composition of claim 16.

20. Aminobutanoic acids of the following formula (I):

wherein:

A and B are independently CR where

R is hydrogen, halogen, $C_{1-3}$alkyl or $C_{1-3}$alkoxy;

$R^1$ is $C_{3-6}$alkyl or $C_{1-3}$alkylthio$C_{1-3}$alkyl;

$R^2$ is hydrogen, $C_{1-4}$alkyl or hydroxy$C_{1-3}$alkyl;

$R^3$ is $C_{1-3}$alkyl, $C_{1-4}$alkoxy, $C_{1-3}$alkylamino, tris(hydroxymethyl)methyl, aryl, substituted aryl, phenylsulfonyl, benzylsulfonyl, pyridinylsulfonyl, pyridinylcarbonyl or —$(CH_2)_n CHR^6 R^7$ where n is the integer 0, 1, 2, 3 or 4;

$R^6$ is hydrogen, $C_{1-3}$alkyl, $C_{1-4}$alkoxy, $C_{1-3}$alkylamino;

$R^7$ is hydroxy, mono- or di-($C_{1-3}$alkyl)amino, aryl, substituted aryl, heteroaryl, substituted heteroaryl, a saturated 5, 6, or 7 membered ring optionally interrupted by 1, 2, 3, or 4 N, S, or O heteroatoms, with the proviso that any two O or S atoms are not bonded to each other, such saturated ring optionally mono-, di-, tri-, or tetrasubstituted independently with $C_{1-3}$alkyl, hydroxy, oxo, phenyl or aminocarbonyl substituents; or $CHR^6 R^7$ together form a saturated 5 to 13 membered ring optionally interrupted by 1, 2, 3, or 4 N, S, or O heteroatoms, sulfonyl or carbonyl, with the proviso that any two O or S atoms are not bonded to each other, such saturated ring optionally mono-, di-, or tri, or tetrasubstituted independently with $C_{1-3}$alkyl, hydroxy, nitro, hydroxy$C_{1-3}$alkyl, phenyl, aminocarbonyl or acetylamino substituents, a saturated 6, 7 or 8 membered bicyclic ring optionally interrupted by 1, 2, 3, or 4 N, S, or O heteroatoms, with the proviso that any two O or S atoms are not bonded to each other, a 9 or 10 membered bicyclic ring which is partially aromatic, such bicyclic ring optionally mono- or disubstituted independently with $C_{1-3}$alkyl, halogen, amino, hydroxy, ($C_{1-2}$alkylsulfonyl)amino, nitro, aminosulfonyl, carboxy, trifluoromethyl, mono-or disubstituted ($C_{1-2}$alkyl)amino or trifluoromethylsulfonylamino substituents, a 9 or 10 membered heterobicyclic ring which is partially aromatic, interrupted by 1 or 2 N, S, O heteroatoms, carbonyl or sulfonyl, with the proviso that any two O or S atoms are not bonded to each other, such heterobicyclic ring optionally mono- or disubstituted independently with $C_{1-3}$alkyl, halogen, amino, hydroxy, ($C_{1-2}$alkylsulfonyl)amino, nitro, aminosulfonyl, carboxy, trifluoromethyl, mono- or disubstituted ($C_{1-2}$alkyl)amino or trifluoromethylsulfonylamino substituents; or $NR^2R^3$ together form a saturated 5, 6, or 7 membered ring optionally interrupted by 1, 2, 3, or 4 N, S, or O heteroatoms, carbonyl or sulfonyl, with the proviso that any two O or S atoms are not bonded to each other, such saturated ring optionally mono-, di-, or trisubstituted independently with $C_{1-3}$alkyl, hydroxy, nitro, phenyl, 2,3-dihydroxypropyl, pyridinyl, ethoxycarbonyl, amino, carboxy, acetylamino, aminosulfonyl, aminocarbonyl, trifluoromethyl, trifluoromethylsulfonylamino, mono- or di-($C_{1-3}$alkyl)amino, halogen or ($C_{1-3}$alkylsulfonyl)amino substituents, an 9 or 10 membered heterobicyclic ring which is partially aromatic, such heterobicyclic ring interrupted by 1, 2, 3, or 4N heteroatoms, such heterobicyclic ring optionally mono-, di-, or trisubstituted independently with $C_{1-3}$alkyl, halogen, amino, ($C_{1-2}$alkylsulfonyl)amino, nitro, aminosulfonyl, carboxy, trifluoromethyl, mono- or disubstituted ($C_{1-2}$alkyl)amino or trifluoromethylsulfonylamino substituents;

$R^4$ is hydrogen, hydroxy, $C_{1-3}$alkyl, $C_{1-3}$alkoxy or halogen;

$R^5$ is hydrogen, $C_{1-6}$alkyl, amino, amino$C_{1-3}$alkyl, mono-or di-($C_{1-3}$alkyl)amino, mono- or di-($C_{1-3}$alkyl)amino$C_{1-3}$alkyl, acetylamino, aryl, substituted aryl, (phenyl)sulfonylamino, nitro, ($C_{1-3}$alkyl)sulfonylamino, hydroxy, $C_{1-6}$alkoxy, halogen, morpholinyl, piperazinyl, piperidinyl, (aryl)$C_{1-4}$alkoxy, (substituted aryl)$C_{1-4}$alkoxy, aryloxy, (substituted aryl)oxy, (aryl)$C_{1-4}$alkyl, (substituted aryl)$C_{1-4}$alkyl, heteroaryl, substituted heteroaryl, (heteroaryl)$C_{1-4}$alkyl, (substituted heteroaryl)$C_{1-4}$alkyl, (heteroaryl)$C_{1-4}$alkoxy, (substituted heteroaryl)$C_{1-4}$alkoxy, heteroaryloxy or (substituted heteroaryl)oxy; or $R^4R^5$ together form an aryl, subsituted aryl or a saturated 5 or 6 membered ring optionally interrupted by 1, 2, or 3N, S, or O heteroatoms, with the proviso that any two O or S atoms are not bonded to each other, such saturated ring optionally mono-, di-, or trisubstituted independently with from $C_{1-3}$alkyl, oxo, nitro or aminosulfonyl substituents;

wherein substituted aryl is defined as an aryl mono-, di-, or trisubstituted independently with $C_{1-4}$alkyl, halogen, amino, hydroxy, acetylamino, ($C_{1-3}$alkylsulfonyl)amino, nitro, aminosulfonyl, aminocarbonyl, carboxy, trifluoromethyl, mono- or disubstituted ($C_{1-4}$alkyl)amino or trifluoromethylsulfonylamino substituents;

wherein heteroaryl is defined as a 5 or 6 membered aromatic ring optionally interrupted by 1, 2, 3 or 4N, S, or O heteroatoms, with the proviso that any two O or S atoms are not bonded to each other;

wherein substituted heteroaryl is defined as heteroaryl mono-, di-, or trisubstituted independently with $C_{1-4}$alkyl, halogen, amino, hydroxy, acetylamino, ($C_{1-3}$alkylsulfonyl)amino, nitro, aminosulfonyl, aminocarbonyl, carboxy, trifluoromethyl, mono- or disubstituted ($C_{1-4}$alkyl)amino, or trifluoromethylsulfonylamino substituents; or a pharmaceutically acceptable acid-addition or organic base-addition salt thereof.

* * * * *